United States Patent
Hazen et al.

(10) Patent No.: US 10,323,252 B2
(45) Date of Patent: Jun. 18, 2019

(54) PLANT BIOMASS YIELD INCREASE BY MODIFIED SWAM1 GENE EXPRESSION

(71) Applicant: University of Massachusetts, Boston, MA (US)

(72) Inventors: Samuel P. Hazen, Amherst, MA (US); Pubudu Handakumbura, Worcester, MA (US)

(73) Assignee: University of Massachusetts, Boston, MA (US)

( * ) Notice: Subject to any disclaimer, the term of this patent is extended or adjusted under 35 U.S.C. 154(b) by 327 days.

(21) Appl. No.: 15/199,714

(22) Filed: Jun. 30, 2016

(65) Prior Publication Data

US 2017/0029838 A1    Feb. 2, 2017

Related U.S. Application Data

(60) Provisional application No. 62/186,801, filed on Jun. 30, 2015.

(51) Int. Cl.
*C12N 15/82* (2006.01)
*C07K 14/415* (2006.01)

(52) U.S. Cl.
CPC ........ *C12N 15/8261* (2013.01); *C07K 14/415* (2013.01); *Y02A 40/146* (2018.01)

(58) Field of Classification Search
None
See application file for complete search history.

(56) References Cited

PUBLICATIONS

Nishimura et al. (Plant Cell Physiol., 41(5):583-590, 2000).*
Yang et al. (PNAS, 98:11438-11443, 2001).*
Yoon et al., Journal of Integrative Plant Biology, 57:902-912; 2015.*
Zhou et al. (Plant Cell, 21:248-266; Published Jan. 2009).*
Zhong et al. (Plant and Cell Physiology, 52:1856-1871; Published Jan. 2011).*
NCBI (GenBank Sequence Accession No. XM_003569586.1; Published Nov. 15, 2011).*

* cited by examiner

*Primary Examiner* — Vinod Kumar
(74) *Attorney, Agent, or Firm* — Schwegman Lundberg & Woessner, P.A.

(57) ABSTRACT

Provided herein are plants and methods to increase plant biomass, for example, a transgenic plant, plant cell, plant part or seed, wherein the transgenic plant, plant cell, plant part or seed comprises a heterologous promoter which increases expression of SWAM1, other genes related to SWAM1, or GNRF, as compared to a non-transgenic plant.

4 Claims, 33 Drawing Sheets

Specification includes a Sequence Listing.

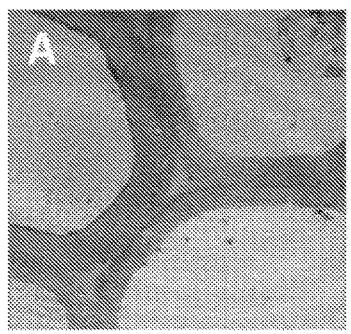 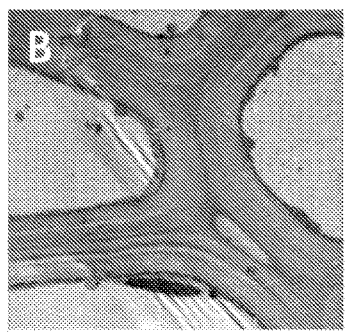 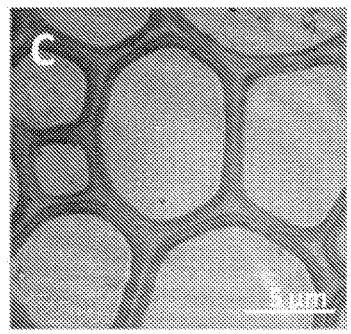
Cont / SWAM1-OE / SWAM1-DR
FIG. 5A  FIG. 5B  FIG. 5C
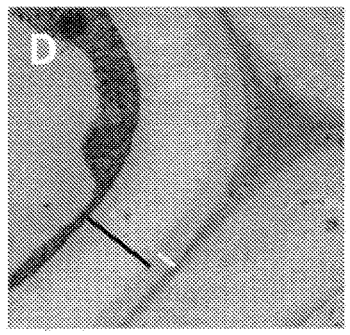 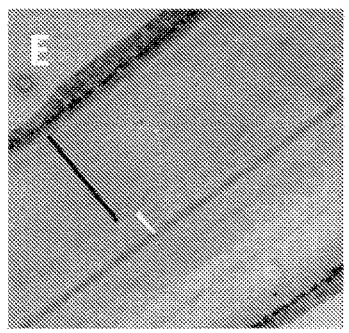 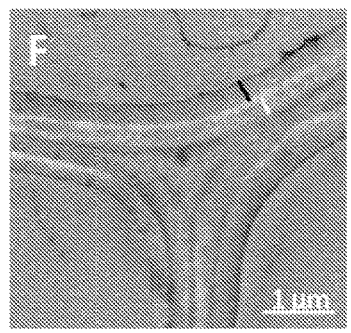
Cont / SWAM1-OE / SWAM1-DR
FIG. 5D  FIG. 5E  FIG. 5F

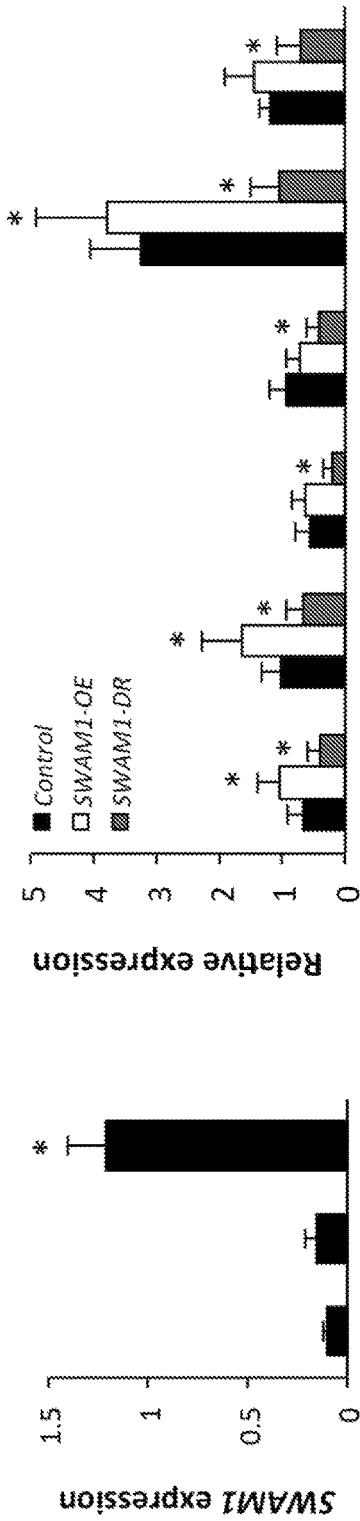
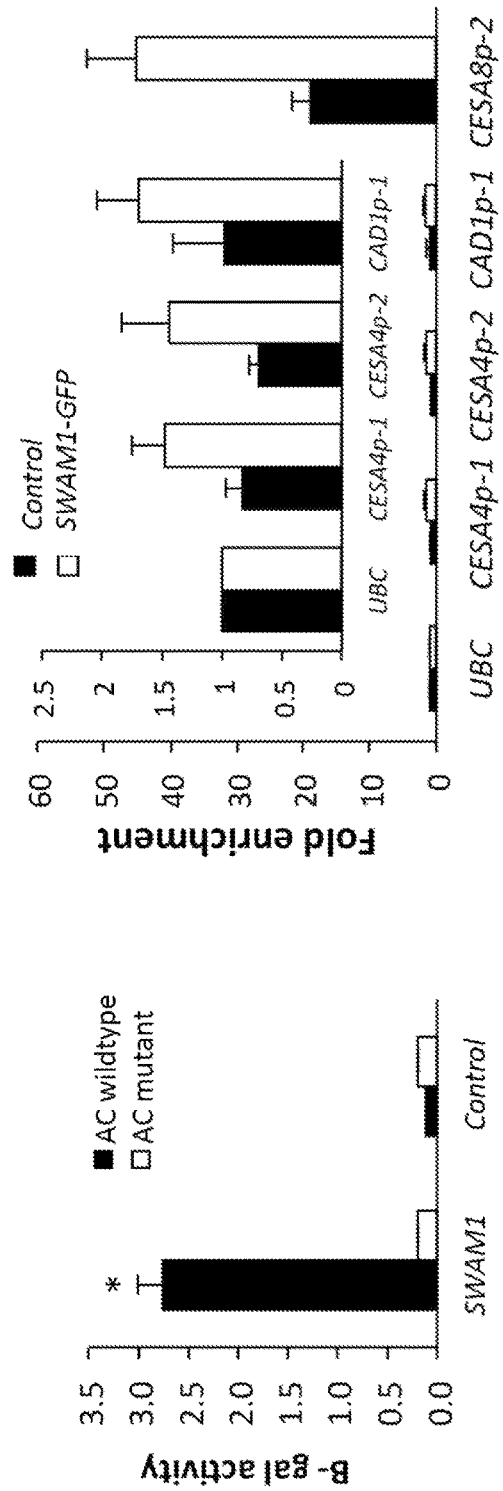
FIG. 6A
FIG. 6B
FIG. 6C
FIG. 6D

| Figure 7B Species | Phylogenetic Tree ID | Locus ID | Protein Sequences |
|---|---|---|---|
| *Brachypodium distachyon* | SWAM2 | Bradi2g17982.1 | MGRLSCGGGGGQAKLRKGLWSPEEDEKLYNHIIRHGVG CWSSVPKLAGLHRCGKSCRLRWINYLRPDLKRGSFSLQEED LIVALHEILGNRWSQIASHLPGRTDNEIKNFWNSCLKKKLR QQGIDPATHKPITAMPDALPTDAQEDEDQKPPTGAGALA PNPKQQAVFDPFPAATDFGGVFDHDGLAAVPALFEGVTG DYSSVLDLDSYGESSSNSSNNNWNGCGAEMSNVLDGEAL HWAPIKDDDDAALGEHKFLLQMPCQEQMSLPHFDFNLEY F |
| | SWAM3 | Bradi2g40620.1 | MGREGAACSSKPKLRRGLWSPEEDEKLYNHIIRYGVGCWS SVPKLAGLERCGKSCRLRWINYLRPDLKRGSFSQDEEDLIVS LHKILGNRWSQIASQLPGRTDNEIKNFWNSCIKKKLRQLGI DPATHKPLNDVDDPATTTLADSCNKQQQLIPDQDDDGSP CFNGSDVDLLLAAAPHSPVCSFDPLSVTNVPATMHSSGFRS DGSLCEYGNSAYTTGGDSSSNSNSAWSNVVEPLPHMDIFI RDSEPYNHPFDPAKFISSWNHQQPHQQQHPADQDVGGG SASFPIRSLSRDVLPESCFQLARGALEDEFDFL |
| | SWAM1 | Bradi2g47590.1 | MGRHAGTGGVQQKLRKGLWSPEEDEKLYNHIIRYGVGCW SSVPKLAGLQRCGKSCRLRWINYLRPDLKRGSFSQQEEDAI VGLHEILGNRWSQIASHLPGRTDNEIKNFWNSCLKKKLRQ RGIDPSTHKPISSAAAAVETDQAPKDQKPQTAVEGFSTLKQ QQVFDPFPVTDTFNGGFDGVGMTLYDNLGGKDASGFVD YSSVLDVSENLGYGESSSNSSNWNCAPEVNNVLEGHWAS ESKAEPFAGYGGGEQDEALEHKFVLPCQGGQEHSMAHFD FNLEYF |

FIG. 7B

| Carica papaya | Cpapaya110.11 evm.model.super contig_110.11 | MGRHSCCLKQKLRKGLWSPEEDEKLFNYITRFGVGCWSSV PKLAGLQRCGKSCRLRWINYLRPDLKRGMFSQQEEDLIISL HEVLGNRWAQIAAQLPGRTDNEIKNFWNSCLKKKLMKQG IDPTTHKPLINNYNNIQVKQEKDCTDQTSHSTLIKPFTNSHE PAFLVNNDSTTSNYQQDALRQDQQFLMNKPVVAYDPLSY FDLPDVPITGYTTISSYVPQNQPTILRSVAFDHTQFETSSNFT FSSMPSLVNFHDYGNMSGTEFSDNSFLLNEAKESSSNSSNI TTTTTALTSNMVENNGAFSWENDNKLDCMFQPSNSWR DQDEQLQSQTCVDLSSFPLASLSEDLTGPNFDRVFHHI |
|---|---|---|
| Eucalyptus gradis | EgrMYB14 Eucgr.K02806.1 | PKLAGLQRCGKSCRLRWINYLRPDLKRGMFSQEEEDLIVSL HKVLGNRWAQIAAQLPGRTDNEIKNFWNSCLKKKLMKQG IDPATHQPISEVQLIKEEKCAENKSLQVPQLKGLTPAVSSSR AHEPAFLISDTCYEGGALIEPSRESADNNNYMSRPVFDSLPY FEFQSGVDMVGFNSNLLSQYHDPPRTIDQSHLDISSNFEFS SMPSLTNFDHPGATMSGSEFSNNSTSRMSPFFFHEAKDQ CSTNNSSSIGNYTGFQVNSSVENAAFSWCSSENKLDCLFQY QANGTSKSEELKPQGSWQEDQLHIGPVNSSSEDFGSFQLT SLSDDLTAANFDIFQQM |
| Medicago truncatula | Medtr1g112760 Medtr1g112760. 1 | MSRRHSCCLKQKLRKGLWSPEEDDKLFNYITMFGVGCWSS VPKLAGLQRCGKSCRLRWINYLRPDLKRGMFSKQEEDLIIN LHEALGNRWAQIASQLPGRTDNEIKNFWNSSLKKKLMKQ GIDPATHKPLINNESLLVKEEKEKPSMIMPLSQPQPQRTLM LESSHEYSEALLMNKPTFDLDPLQLQFELNQFGTNSSYFFSS DNISNNSFSNMINENTAGGLISWEGEN |

FIG. 7C

| | | |
|---|---|---|
| | Medtr3g077110 | MGRHFCSLKQKLRKGLWSPEEDEKLFNYITMFGVGCWSSV<br>PKLAGLQRCGKSCRLRWINYLRPDLKRGMFSKQEEDLIINL<br>HEALGNRWAQIAAQLPGRTDNEIKNFWNSSLKKKLMKQG<br>IDPATHKPFINNIESLIKEEKEPSMIMPLSHSQPQRILATHT<br>MLESSHDYSESLLMSDLINHYNIGGLALTEASRIFLMNNPTL<br>DFDPLYYNSSLINYYQPSLLQFEQNQFGNNSSYFFSSMPCL<br>NSSEFSDNINNSVSKFSSPLVNESSSNSTSTMSDYYQJSNMI |
| | Medtr3g077110.<br>1 | NENAGGLISWEGEEFINKTSSWQEGQLLSHNNSIDFSTYPL<br>TSLSEDLSNIEANFDVFHHL |
| | Medtr4g105130 | MGRHSCCLRQKLRKGLWSPEEDEKLFNHITRFGVGCWSSV<br>PKQAGLQRCGKSCRLRWINYLRPDLKRGMFSQQEEDLIISL<br>HEVLGNRWAQIAAQLPGRTDNEIKNFWNSCLKKKLLKQGI<br>DPTTHKPLTEAYLKEENKITETTVPSMQIPSITHGSAFLITDS<br>SYYDDNGLTEASREIFTSKQALDPLFCYDFQSGYNLPMSNY<br>HTTLKPCDQSQFGLNSSYGFTSMPSLTNSDHANVSVTEFS<br>DNNSASKINSFFMNDQVKESNSSNSSNMSTIYPSQMRST |
| | Medtr4g105130.<br>1 | MMENNNAGFCWDGSEKNIDPLFQFQVNAIKSEDYGTSS<br>WEEGQLQTHNSIEDFNSYPLTSLSEDLTEANFDVFHHI |
| *Musa*<br>*acuminata* | Macuminata93945<br>13 | MGRHSCCLRQKLRKGLWSPEEDEKLYNHIIAFGVGCWSSV<br>PKLAGLQRCGKSCRLRWINYLRPDLKRGSFSQQEEDVIIGLH<br>GILGNRWSKIASQLPGRTDNEIKNFWNSCLKKKLRLRGIDP<br>TTHRPLNEVKTQEETIRMYYSNSGANFEQLPEHPFPLIEIQT<br>CLDSIESNANFYYQFHQPFEPLSQNECLVKPELCDYGGVM<br>DVPENFGYGESSSNSGNWNCNVVPEIKHVFGSEALNWVS<br>VSKAETLVEPHEHKHSSWRECQHVMSSEDFSTEPVGSLPR |
| | XP_009394513.1 | DLSDICFNVPRDASVGEFNVEFI |

FIG. 7D

| | | |
|---|---|---|
| Macuminata93955 | XP_009395536.1 | MIPLPQPLMHINLLSPSTSRNTRRGFGGMGRHSCCLEQKIR KGLWSPEEDEKLYNHIIRYGVGCWSSVPKLAGLQRCGKSCR LRWINYLRPDLKRGNFSQQEEDLIISLHEIMGNRWSQIASQ LPGRTDNEIKNYWNSCLKKLRQRGIDPSTHKPLCETETEA QEASRTHLEQLPLQPVFDPFPLIETETCLDSVENNVNIYNQF HQSFESSLAQTECYANSGLREYSSVLDVYGDSSSNSSNWNC NTGAEMKDVVGDEALNWVAQSEGEAPPHVHMNGGEAH EHKFSPWQEKTNAESSEDYSTYSMRFLSCDVAETCFDIHRG ALASEFNVDFF |
| Macuminata93963 | XP_009396318.1 | MGRHSCCLKQKIRKGLWSPEEDEKLYDHIIRCGVGCWSSV PKLAGLERCGKSCRLRWINYLRPDLKRGNFSQQEEDTIIRLH EIMGNRWSQIASQLPGRTDNEIKNYWNSCLKKKLRQRGID PSSHKPLSEIAAQEEGTRTHCSNTGAAFEQLQLHPVFDTFPL IEIQTCLDSVETNVSIYGQFHQTFEPVGQDECLVNLELCDHG SALDNIGHGDSSINSNWNCNIGSEMKSVFGDEDLNWVS QSKVETPAHMQMNEEKTHEHKFNHWQEKNTYPIPVRSLS HDLSETCFSVSRDAMESEFNVDFC |
| Oryza sativa | LOC_Os05g46610 Os05g46610.1 | MGRLSSCGGVQAKLRKGLWSPEEDDKLYNHIIRHGVGCW SSVPKLAGLQRCGKSCRLRWINYLRPDLKRGSFSQQEEDLIV ALHEILGNRWSQIASHLPGRTDNEIKNFWNSCLKKKLRQR GLDPATHKPIAAAAAATSSESAVTQVDEDHKPHGAAAAA AAADGLAANAKQSVFDPFPVTDFGAGFDLGAANMAAALY GSHPDDGAGFVADYSSVLDVSENLGYGESSSNSSNWTCAE VSNVLDSEVLNWAASAGADAAAKAEPFADMEQQHSGYG GEYQVEDDATLEHKFSLPCHEQSLAQFDFNLEYF |

FIG. 7E

| | | |
|---|---|---|
| Os01g36460 | | MGRESAAACSPKPKLRRGLWSPEEDEKLFNHISRYGVGCW SSVPKLAGLERCGKSCRLRWINYLRPDLKRGSFSQQEELIIS LHKILGNRWSQIAAQLPGRTDNEIKNFWNSCLKKLRQRGI DPATHKPLNDGGAGAGEEHHDDGDKQQLMDDVDDCFAI GGGGSSDSLAPPHSPAVSFDPLSVTNVPTTMMQSSSSPYG AAGGEHSSFRSDTLCDYGGSSGGGVDVVSDAGTYSAYTGDS SSNSNSTAWTCGSVVVGGAGELPPPLLPHMDMFGRVD |
| | LOC_Os01g36460 .1 | AEPPPYPPFDVQARFSPWHHHHHHEPTLPTPPQRLDG GGGAAASFPIRSLSRDMPESCFDLGRGALDDEFGVDFL |
| Os01g50720 | | MGRHACSAAGVQQKLRKGLWSPEEDEKLYNHIYRYGVGC WSSVPKLAGLQRCGKSCRLRWINYLRPDLKRGSFSQQEED AIVGLHEILGNRWSQIASHLPGRTDNEIKNFWNSCLKKKLR QRGIDPSTHQPISTAAAAAAALDTSTQDQKPPATADGFA LKQQQQVFDPFPVIDSFGSGFDATGMPLYGHLGGKDAAG FVDYSSVLDVSENLGYGESSSNSSNWNCGVGAPEVNNALE |
| | LOC_Os01g50720 .1 | SEPLHWATESKVEPFVGYGEGDAMEHKFGLPCHGGQQEQG MTHFDFDVSRSMVVGDFNFEYFR |
| Os01g50720 | | MGRLSCGGGVQPKLRKGLWSPEEDEKLYNHIIRHGVGCW SSVPKLAGLQRCGKSCRLRWINYLRPDLKRGSFSQQEEDLIL ALHEILGNRWSQIASHLPGRTDNEIKNFWNSCLKKKLRQR GIDPSTHKPIAGAGAGAVDHDRKPAAGDSDEGLAQKQPA VFDPFPLADFGFDLGAAGVAALYCGPYDDGVGKASPDAG WFVADYSSVLDVSENLGYGESSSNSSNWTCAEMSSAVLDS |
| Panicum virgatum | Pavir.Ca01788 | Pavir.Ca01788.1. p | EVLHWASGGAAKPEPYTELEQQQRSGGYGGGEQAVDD DDDALEHKFSLPCGQEQSLAHFDFNLEYF |

FIG. 7F

Pavir.J18139    Pavir.J18139.1.p    MGREAAAARPKLRRGLWSPEEDEKLYNHIIRYGVGCWSS
VPKLAGLERCGKSCRLRWINYLRPDLKRGSFSQQEEDLIISL
HKILGNRWSQIASQLPGRTDNEIKNFWNSCIKKKLRQRGID
PATHKPLEDDAAAAANSGEAPRDDCNKLLPATADDHCG
FAMGGASSDPLAPHSPTVSFDPLSVTNVPAMQGSYGAAH
SFQPDNLCDYGGAAAYSAAAYTGGGADSSSNSNGTWTCG
NAVGGEPMPQLDMFGREAYHQFDPANKYSPWQQHEAA
RLHDGIGGAAGFPIRSMSRDLPDSCFDLARSGLEDEFSVDF
L Pavir.J19191    Pavir.J19191.1.p    MGRLSCGGGVQPKLRKGLWSPEEDEKLYNHIIRHGVGCW
SSVPKLAGLQRCGKSCRLRWINYLRPDLKRGSFSQQEGDLIL
ALHEILGNRWSQIASHLPGRTDNEIKNFWNSCLKKKLRQR
GIDPSTHKPIAGAAEVGAALPDARDHDHKPAAAAGDSDD
GLAQKQPAVFDPFPLADFGFDLGAAGVAALYCGPYDDGV
GKASPDAGGFVADYSSVLDVSENLGYGESSSNSSNWTCAE
MSSAVLDSEVLHWASGGGGGGGAAKPEPYTELERQQHSGG
YGGVEQAVDDDDALEHKFSLPCGQEQSLAHFDFNLEYF Pavir.J20716    Pavir.J20716.1.p    MGREAAAARPKLRRGLWSPEEDEKLYNHIIRYGVGCWSSV
PKLAGLERCGKSCRLRWINYLRPDLKRGSFSQQEEDLIINLH
KILGNRWSQIASQLPGRTDNEIKNFWNSCIKKKLRQRGIDP
ATHKPLEDDDDAAAAANSGEAARDDSKQLPAASDDHCGF
AMGGACSDPLAPHSPTVSFDPLSVTNVPEMQGSYGAAHS
FRPDNLCDYGGVDAASEGAAAYSAAAYTGGGVDSSSNSN
GTWTCGNVVGGEPMQQLDMFGGREAYHQFDPAKYSLW
QQHEAARLHDGVGGATGFPIRSMSRDLPDSCFDLARSGLE
DEFSVDFL

FIG. 7G

*Populus trichocarpa*

Potri.012G084100

0.1 MGRHSCCLKQKLRKGLWSPEEDERLFNYITRFGVGCWSSV
PKLAGLQRCGKSCRLRWINYLRPDLKRGMFSQQEEDLIISF
HEVLGNRWAQIAAQLPGRTDNEIKNFWNSCLKKKLMKQG
IDPATHKPLSQVEVKEEKICTEKASFQIPQSKGLPILSNFSAPE
PAFIINDTAYNSSGLTEASREQFINKQAYDPIAYFEFPPSIVPT
GYNSNLSSVYHPTVRPLDQNQFETSSNFVFTSMPSLTSFDH
GSMSGTDFSDNSASRMSSMFLNEAKESSSNSNISNYAGY
QMSNMVENAAGFSSWDSDDKLESVFQYHQVNGIKTGEL
KPSPWHDAGQLHTHQNSVDFSSCPLKSLSEDLKGANFDGF
HQI

Potri.015G082700

0.1 MGRHSCCLKQKLRKGLWSPEEDEKLLNYITRFGVGCWSSV
PKLAGLQRCGKSCRLRWINYLRPDLKRGMFSQQEEDLIISL
HEVLGNRWAQIAAQLPGRTDNEIKNLWNSYLKKKLMKQG
IDPTTHKPLCQVGVKEEKDCTEKASFQIPQSKGLPIVSNFTA
QEPAFLINDTTYNSSGLPEVSREQFLNKQAYDPLSYFEFPAG
IDLTGYNPSLSSVYHPTVRSLDQNQFETSSNFGFTSMPSLTS
FDHGSMSGTDFSDNSASRMSSMFLNEAKESSSNSSNISNY
AGYQMNNMVENAAAFSSWDSDDHKLESVFQYHQVNGV
KTEELKPSPWHEAGRLHTHQNSVDFNSYPLTSLSEDITGAN
FDVFHQI

FIG. 7H

| | | |
|---|---|---|
| *Prunus persica* | Ppersica018561m ppa018561m | MGRHSCCLKQKLRKGLWSPEEDEKLFNYITRFGVGCWSSV PKLAGLQRCGKSCRLRWINYLRPDLKRGMFSQQEEDLIISL HEVLGNRWAQIAAQLPGRTDNEIKNFWNSCLKKKLLKQGI DPTTHKPLSEEEMKEKKSMDCSELKECLPMPEHEQGLPTIP AMSSSQGPTFLVNDSNYFDGAGVLTQASRAFDSLSYFEFQ TGIEPSGYNSDLVSTQYHPTNVRPHFNQPHNTTYETSSNFG FTSMPSLANSDHGSMSGTDFSDNSASRLSSFFMNEVKECS SNSSNVSSYAAGFHMNNNSNNNNNNVVENAAFSWDT DNKLDSLFQFHANGIKSEELIKPNSWQQGQQLLHAQNSVD FNSYPLTSLSEDLTGANFDVFQHI |
| *Solanum tuberosum* | Stuber31557 | MGRHSCSVKQKLRKGLWSPEEDEKLCNYITNFGIGSWSSV PKLAGLQRCGKSCRLRWINYLRPDLKRGMFSQDEEDKIISL HQVLGNRWAQIAAQLPGRTDNEIKNFWNSSLKKKLMKQ GIDPNTHKPLKENQVIKDEENCTNKTSMLQIPPHLNEMAN GQFTESKQVFDLLFVPDFQSNSNPSEYNSEVLAQYHDQQS EFENNPNYVFCSASSVTKLEHGQMTETDFGSSSTSRMSSS NSSNMCSNQNTAGIQINGMSENSEALSWDIENKMESLFQ |
| | PGSC0003DMP40 0031557 | YPYIGIKNEELKSSPSQERDQLYGNSTSGDFMSNYPLSSLTE EFKWG |

FIG. 7I

| | | |
|---|---|---|
| Stuber47028 | PGSC0003DMP40 0047028 | MGRHSVFVKEKTRKGLWSPEEDEKLYNYITRFGVGCWSSV PKLAGLQRCGKSCRLRWINYLRPDLKRGMFSQEEDMIITL HKVVGNRWAQIAAKLPGRTDNEIKNFWNSNLKKKLIKQGI DPNTHKPLSENHQVRNETNYTDKASSLLPNMSNSAEIEQP FHFNSKRSFNSEAITRQLTEVSRNQLVSKQVFDPLFLYEFQA NVNPIGPYVHHHNQIEGNQDFGFCSNFQHGHMTTESDIS DSSTSRMSTSNSSNTMISHYSSAGIQINEMLEWDADNKID SLIQYPYVGIKNEENFSNNNPLSGENLDVFHHI |
| Vitis vinifera | Vvinifera07670001 001 GSVIVT01007670 | MGRHSCCLLKQKLRKGLWSPEEDEKLYNYITRFGVGCWSSV PKLAGLQRCGKSCRLRWINYLRPDLKRGMFSQQEEDIIISLH QVLGNRWAQIAAQLPGRTDNEIKNFWNSCLKKKLLKQGM DPNTHKPLNETEVGDGKNCTEKASLQLQHHFHCCHFPDFS YIQTRKFYPLLPFL MGRHAASGGGGGVQQKLRKGLW SPEEDE KLYNH IIRYGVGCW SSVPKLAGLQRCGKSC RLRW NYILRPDLKRGSFSQQEEDAVGLHEI LGNRW SQIASHLPGRTDNEKNFW NSCLKK KLRQRG IDPSTHKP ISANTAAAALEQPAASQ ERKPLSTAAADGGFDTKHQHQQVFDPFPLT DSFGGGFDAAAGAALYGHMGGGGGKQDA GAFVDYSSVLDVSENLGYGESSSNSSNW N CAPEANNALDGGDAPLHW ASESKATPHFA GYGGGEEQSLEEHKFLLPCHGQQEQSLPH |
| Sorghum bicolor | not featured in tree Sb03g032260 | |

FIG. 7J

| | | |
|---|---|---|
| not featured in tree | Sb09g027200 | MGKLSGGGGVPKLKKGLW SPEEDEKLY NHIRHGVGCW SSVPKLAGLQRCGKSCRLR W INYLRPDLKRGSFSQQEEDLTALHEILGNR W SQ ASHLPGRTDNEKNFW NSCLKKKLRQ RG IDPATHKP IAAG AAAEAGTALPDGRDHD RKPGG AADGDG DADG LAQSKQLQ PAAAVF DPFPVTDFG FDLGVAALYCGPYDDGKASPD AGFVADYSSVLDVSENLG YG ESSSNSSNW NCGAEM SNAVLDSEVLHW ASGAAAAKPEP YTELEQQQHSGG YSGGGGQAVDDDDA |
| not featured in tree | Sb03g024500 | MGREAAATRPKLRRG LW SPEEDEKLYNHII RYGVGCW SSVPKLAG LERCGKSCRLRW IN YLRPDLKRGSFSQQEEDLIISLHKILGNRW S QIASQLPGRTDNEKNFW NSCKKKLRQRGI DPATHKPLNDDDDVVVAADDNTVAPHRHQ DDKKLASSTDDQCFAAM GAAAASSDDPLA PHSPTVSFDPLSVTNVPTM QQGSYGAAHS FGRSDNHLCDYGGVDVVSDAATTYSAYTG GGDSSSNSNGTW TCGGNNVVGGDPMPPH MDMFGRDAEAVYQQFDPAKYSPW QHQQQ MGKHAASGGVVKLKKGLW SPEEDEKL YNHIIRYGVGCW SSVPKLAGLQRCGKSCRL RW INYLRPDLKRGSFSQQEEDAIVGLHQ IIG NRW SQ FASHLPGRTDNEKNFW NSCLKKKL RQRG IDTSTHKPAVSASVPAASEQPVSQDR KPLAAAADGGSDMKHQQVFDPFPLTDSF GGGFGAALYGHTGG KQDAAAFVDYSSVLD VSENLGYGGESSSNSSNW NCAPEVHNNAL |
| not featured in tree | GRMZM2G00340 6_T01 | DGDAPLHW ASESKATPFAGYGGEEQSLLG HRFSVPCHGQQEQSPPRFDEDGRGAVVG |

FIG. 7K

| | | |
|---|---|---|
| not featured in tree | GRMZM2G17523 2_T01 | MGRLSCGGGGGGVQPKLRKGLWSPEED EKLYNHIRHGVGCWSTVPKLAGLQRCGKS CRLRWINYLRPDLKRGSFSQQEEDLVALH EILGNRWSQIASHLPGRTDNEIKNFWNSCL KKKLRQRGIDPATHKPVAAAEASAALPDAR DHDREPGGAGAGADADGLAQQSKQPAAA VFDPFPVVDFGFDLSGGGVAALYGGPYD AAAGKASADDGFVADYSSVLDVSENLGY GESSSNSSNWGNGAEMGNAAAAVLDGEV LHWAKPEPYTELEQRSAGQAAADDDALHH IRYGVGCWSSVPKLAGLERCGKSCRLRWIN YLRPDLKRGSFSQQEEDLWSLHKILGNRW SQIASQLPGRTDNEIKNFWNSCIKKKLRQQ GIDPATHKPINDDDNAAAAAADNDAAVAP HHHRRHQDDHCGAANIDNNNNNNNNNN RQLPSADDHCFAMSSDDPLAPHSPTVSFDP LSVTNVPTAMQQGSYGSFRSDNDHLCDYG GGGVDVVSDAATAYSAPYTGGGGGGDS |
| not featured in tree | GRMZM2G06 4744_P01 | SSNSNGNGTWACSGGEPMPPHVAMFGRD AAQAAAYHQFVDPAKYSPWQQHPAARLHD HNVGGAAAGFPRSMSRDLPGSCFDLARSA |

FIG. 7L

SEQUENCE LISTING

```
<160> NUMBER OF SEQ ID NOS: 75

<210> SEQ ID NO 1
<211> LENGTH: 14
<212> TYPE: DNA
<213> ORGANISM: Artificial Sequence
<220> FEATURE:
<223> OTHER INFORMATION: A synthetic oligonucleotide

<400> SEQUENCE: 1
tttagatatc ataa                                                         14

<210> SEQ ID NO 2
<211> LENGTH: 278
<212> TYPE: PRT
<213> ORGANISM: Brachypodium distachyon

<400> SEQUENCE: 2

Met Gly Arg Leu Ser Cys Gly Gly Gly Gly Gly Gln Ala Lys Leu
1               5                   10                  15

Arg Lys Gly Leu Trp Ser Pro Glu Glu Asp Glu Lys Leu Tyr Asn His
                20                  25                  30

Ile Ile Arg His Gly Val Gly Cys Trp Ser Ser Val Pro Lys Leu Ala
            35                  40                  45

Gly Leu His Arg Cys Gly Lys Ser Cys Arg Leu Arg Trp Ile Asn Tyr
        50                  55                  60

Leu Arg Pro Asp Leu Lys Arg Gly Ser Phe Ser Leu Gln Glu Glu Asp
65                  70                  75                  80

Leu Ile Val Ala Leu His Glu Ile Leu Gly Asn Arg Trp Ser Gln Ile
                85                  90                  95

Ala Ser His Leu Pro Gly Arg Thr Asp Asn Glu Ile Lys Asn Phe Trp
            100                 105                 110

Asn Ser Cys Leu Lys Lys Lys Leu Arg Gln Gln Gly Ile Asp Pro Ala
        115                 120                 125

Thr His Lys Pro Ile Thr Ala Met Pro Asp Ala Leu Pro Thr Asp Ala
    130                 135                 140

Gln Glu Asp Glu Asp Gln Lys Pro Pro Thr Gly Ala Gly Ala Leu Ala
145                 150                 155                 160

Pro Asn Pro Lys Gln Gln Ala Val Phe Asp Pro Phe Pro Ala Ala Thr
                165                 170                 175

Asp Phe Gly Gly Val Phe Asp His Asp Gly Leu Ala Ala Val Pro Ala
            180                 185                 190

Leu Phe Glu Gly Val Thr Gly Asp Tyr Ser Ser Val Leu Asp Leu Asp
        195                 200                 205
```

```
Ser Tyr Gly Glu Ser Ser Asn Ser Asn Asn Asn Trp Asn Gly
    210                 215                 220

Cys Gly Ala Glu Met Ser Asn Val Leu Asp Gly Glu Ala Leu His Trp
225                 230                 235                 240

Ala Pro Ile Lys Asp Asp Asp Ala Ala Leu Gly Glu His Lys Phe
                245                 250                 255

Leu Leu Gln Met Pro Cys Gln Glu Gln Met Ser Leu Pro His Phe Asp
            260                 265                 270

Phe Asn Leu Glu Tyr Phe
            275

<210> SEQ ID NO 3
<211> LENGTH: 314
<212> TYPE: PRT
<213> ORGANISM: Brachypodium distachyon

<400> SEQUENCE: 3

Met Gly Arg Glu Gly Ala Ala Cys Ser Ser Lys Pro Lys Leu Arg Arg
1               5                   10                  15

Gly Leu Trp Ser Pro Glu Glu Asp Glu Lys Leu Tyr Asn His Ile Ile
            20                  25                  30

Arg Tyr Gly Val Gly Cys Trp Ser Ser Val Pro Lys Leu Ala Gly Leu
        35                  40                  45

Glu Arg Cys Gly Lys Ser Cys Arg Leu Arg Trp Ile Asn Tyr Leu Arg
50                  55                  60

Pro Asp Leu Lys Arg Gly Ser Phe Ser Gln Asp Glu Glu Asp Leu Ile
65                  70                  75                  80

Val Ser Leu His Lys Ile Leu Gly Asn Arg Trp Ser Gln Ile Ala Ser
                85                  90                  95

Gln Leu Pro Gly Arg Thr Asp Asn Glu Ile Lys Asn Phe Trp Asn Ser
            100                 105                 110

Cys Ile Lys Lys Lys Leu Arg Gln Leu Gly Ile Asp Pro Ala Thr His
        115                 120                 125

Lys Pro Leu Asn Asp Val Asp Asp Pro Ala Thr Thr Thr Leu Ala Asp
130                 135                 140

Ser Cys Asn Lys Gln Gln Gln Leu Ile Pro Asp Gln Asp Asp Asp Gly
145                 150                 155                 160

Ser Pro Cys Phe Asn Gly Ser Asp Val Asp Leu Leu Leu Ala Ala Ala
                165                 170                 175

Pro His Ser Pro Val Cys Ser Phe Asp Pro Leu Ser Val Thr Asn Val
            180                 185                 190

Pro Ala Thr Met His Ser Ser Gly Phe Arg Ser Asp Gly Ser Leu Cys
        195                 200                 205

Glu Tyr Gly Asn Ser Ala Tyr Thr Thr Gly Gly Asp Ser Ser Ser Asn
210                 215                 220

Ser Asn Ser Ala Trp Ser Asn Val Val Glu Pro Leu Pro His Met Asp
225                 230                 235                 240

Ile Phe Ile Arg Asp Ser Glu Pro Tyr Asn His Pro Phe Asp Pro Ala
                245                 250                 255

Lys Phe Ile Ser Ser Trp Asn His Gln Gln Pro His Gln Gln His
            260                 265                 270

Pro Ala Asp Gln Asp Val Gly Gly Ser Ala Ser Phe Pro Ile Arg
        275                 280                 285

Ser Leu Ser Arg Asp Val Leu Pro Glu Ser Cys Phe Gln Leu Ala Arg
```

```
                    290                 295                 300
Gly Ala Leu Glu Asp Glu Phe Asp Phe Leu
305                 310

<210> SEQ ID NO 4
<211> LENGTH: 283
<212> TYPE: PRT
<213> ORGANISM: Brachypodium distachyon

<400> SEQUENCE: 4

Met Gly Arg His Ala Gly Thr Gly Gly Val Gln Gln Lys Leu Arg Lys
1               5                   10                  15

Gly Leu Trp Ser Pro Glu Glu Asp Glu Lys Leu Tyr Asn His Ile Ile
            20                  25                  30

Arg Tyr Gly Val Gly Cys Trp Ser Ser Val Pro Lys Leu Ala Gly Leu
        35                  40                  45

Gln Arg Cys Gly Lys Ser Cys Arg Leu Arg Trp Ile Asn Tyr Leu Arg
    50                  55                  60

Pro Asp Leu Lys Arg Gly Ser Phe Ser Gln Gln Glu Glu Asp Ala Ile
65                  70                  75                  80

Val Gly Leu His Glu Ile Leu Gly Asn Arg Trp Ser Gln Ile Ala Ser
                85                  90                  95

His Leu Pro Gly Arg Thr Asp Asn Glu Ile Lys Asn Phe Trp Asn Ser
            100                 105                 110

Cys Leu Lys Lys Lys Leu Arg Gln Arg Gly Ile Asp Pro Ser Thr His
        115                 120                 125

Lys Pro Ile Ser Ser Ala Ala Ala Val Glu Thr Asp Gln Ala Pro
    130                 135                 140

Lys Asp Gln Lys Pro Gln Thr Ala Val Glu Gly Phe Ser Thr Leu Lys
145                 150                 155                 160

Gln Gln Gln Val Phe Asp Pro Phe Pro Val Thr Asp Thr Phe Asn Gly
                165                 170                 175

Gly Phe Asp Gly Val Gly Met Thr Leu Tyr Asp Asn Leu Gly Gly Lys
            180                 185                 190

Asp Ala Ser Gly Phe Val Asp Tyr Ser Ser Val Leu Asp Val Ser Glu
        195                 200                 205

Asn Leu Gly Tyr Gly Glu Ser Ser Ser Asn Ser Ser Asn Trp Asn Cys
    210                 215                 220

Ala Pro Glu Val Asn Asn Val Leu Glu Gly His Trp Ala Ser Glu Ser
225                 230                 235                 240

Lys Ala Glu Pro Phe Ala Gly Tyr Gly Gly Glu Gln Asp Glu Ala
                245                 250                 255

Leu Glu His Lys Phe Val Leu Pro Cys Gln Gly Gly Gln Glu His Ser
            260                 265                 270

Met Ala His Phe Asp Phe Asn Leu Glu Tyr Phe
        275                 280

<210> SEQ ID NO 5
<211> LENGTH: 361
<212> TYPE: PRT
<213> ORGANISM: Carica papaya

<400> SEQUENCE: 5

Met Gly Arg His Ser Cys Cys Leu Lys Gln Lys Leu Arg Lys Gly Leu
1               5                   10                  15

Trp Ser Pro Glu Glu Asp Glu Lys Leu Phe Asn Tyr Ile Thr Arg Phe
```

```
            20                  25                  30
Gly Val Gly Cys Trp Ser Ser Val Pro Lys Leu Ala Gly Leu Gln Arg
            35                  40                  45
Cys Gly Lys Ser Cys Arg Leu Arg Trp Ile Asn Tyr Leu Arg Pro Asp
 50                  55                  60
Leu Lys Arg Gly Met Phe Ser Gln Gln Glu Glu Asp Leu Ile Ile Ser
 65                  70                  75                  80
Leu His Glu Val Leu Gly Asn Arg Trp Ala Gln Ile Ala Ala Gln Leu
                    85                  90                  95
Pro Gly Arg Thr Asp Asn Glu Ile Lys Asn Phe Trp Asn Ser Cys Leu
                100                 105                 110
Lys Lys Lys Leu Met Lys Gln Gly Ile Asp Pro Thr Thr His Lys Pro
                115                 120                 125
Leu Ile Asn Asn Tyr Asn Asn Ile Gln Val Lys Gln Glu Lys Asp Cys
                130                 135                 140
Thr Asp Gln Thr Ser His Ser Thr Leu Ile Lys Pro Phe Thr Asn Ser
145                 150                 155                 160
His Glu Pro Ala Phe Leu Val Asn Asn Asp Ser Thr Thr Ser Asn Tyr
                165                 170                 175
Gln Gln Asp Ala Leu Arg Gln Asp Gln Gln Phe Leu Met Asn Lys Pro
                180                 185                 190
Val Val Ala Tyr Asp Pro Leu Ser Tyr Phe Asp Leu Pro Asp Val Pro
                195                 200                 205
Ile Thr Gly Tyr Thr Thr Ile Ser Ser Tyr Val Pro Gln Asn Gln Pro
                210                 215                 220
Thr Ile Leu Arg Ser Val Ala Phe Asp His Thr Gln Phe Glu Thr Ser
225                 230                 235                 240
Ser Asn Phe Thr Phe Ser Met Pro Ser Leu Val Asn Phe His Asp
                245                 250                 255
Tyr Gly Asn Met Ser Gly Thr Glu Phe Ser Asp Asn Ser Phe Leu Leu
                260                 265                 270
Asn Glu Ala Lys Glu Ser Ser Asn Ser Ser Asn Ile Thr Thr Thr
                275                 280                 285
Thr Thr Thr Ala Leu Thr Ser Asn Met Val Glu Asn Asn Gly Ala Phe
                290                 295                 300
Ser Trp Glu Asn Asp Asn Lys Leu Asp Cys Met Phe Gln Pro Ser Asn
305                 310                 315                 320
Ser Trp Arg Asp Gln Asp Glu Gln Leu Gln Ser Gln Thr Cys Val Asp
                325                 330                 335
Leu Ser Ser Phe Pro Leu Ala Ser Leu Ser Glu Asp Leu Thr Gly Pro
                340                 345                 350
Asn Phe Asp Arg Val Phe His His Ile
                355                 360

<210> SEQ ID NO 6
<211> LENGTH: 382
<212> TYPE: PRT
<213> ORGANISM: Eucalyptus gradis

<400> SEQUENCE: 6

Met Gly Arg His Ser Cys Cys Val Lys Gln Lys Leu Arg Lys Gly Leu
 1               5                  10                  15
Trp Ser Pro Glu Glu Asp Glu Lys Leu Phe Asn Tyr Ile Thr Arg Phe
                20                  25                  30
```

```
Gly Val Gly Cys Trp Ser Ser Val Pro Lys Leu Ala Gly Leu Gln Arg
             35                  40                  45

Cys Gly Lys Ser Cys Arg Leu Arg Trp Ile Asn Tyr Leu Arg Pro Asp
     50                  55                  60

Leu Lys Arg Gly Met Phe Ser Gln Glu Glu Asp Leu Ile Val Ser
 65                  70                  75                  80

Leu His Lys Val Leu Gly Asn Arg Trp Ala Gln Ile Ala Ala Gln Leu
                 85                  90                  95

Pro Gly Arg Thr Asp Asn Glu Ile Lys Asn Phe Trp Asn Ser Cys Leu
            100                 105                 110

Lys Lys Lys Leu Met Lys Gln Gly Ile Asp Pro Ala Thr His Gln Pro
            115                 120                 125

Ile Ser Glu Val Gln Leu Ile Lys Glu Glu Lys Cys Ala Glu Asn Lys
130                 135                 140

Ser Leu Gln Val Pro Gln Leu Lys Gly Leu Thr Pro Ala Val Ser Ser
145                 150                 155                 160

Ser Arg Ala His Glu Pro Ala Phe Leu Ile Ser Asp Thr Cys Tyr Glu
                165                 170                 175

Gly Gly Ala Leu Ile Glu Pro Ser Arg Glu Ser Ala Asp Asn Asn Asn
            180                 185                 190

Tyr Met Ser Arg Pro Val Phe Asp Ser Leu Pro Tyr Phe Glu Phe Gln
            195                 200                 205

Ser Gly Val Asp Met Val Gly Phe Asn Ser Asn Leu Leu Ser Gln Tyr
            210                 215                 220

His Asp Pro Pro Arg Thr Ile Asp Gln Ser His Leu Asp Ile Ser Ser
225                 230                 235                 240

Asn Phe Glu Phe Ser Ser Met Pro Ser Leu Thr Asn Phe Asp His Pro
                245                 250                 255

Gly Ala Thr Met Ser Gly Ser Glu Phe Ser Asn Asn Ser Thr Ser Arg
            260                 265                 270

Met Ser Pro Phe Phe His Glu Ala Lys Asp Gln Cys Ser Thr Asn
            275                 280                 285

Asn Ser Ser Ser Ile Gly Asn Tyr Thr Gly Phe Gln Val Asn Ser Ser
290                 295                 300

Val Glu Asn Ala Ala Phe Ser Trp Cys Ser Ser Glu Asn Lys Leu Asp
305                 310                 315                 320

Cys Leu Phe Gln Tyr Gln Ala Asn Gly Thr Ser Lys Ser Glu Glu Leu
                325                 330                 335

Lys Pro Gln Gly Ser Trp Gln Glu Asp Gln Leu His Ile Gly Pro Val
            340                 345                 350

Asn Ser Ser Ser Glu Asp Phe Gly Ser Phe Gln Leu Thr Ser Leu Ser
            355                 360                 365

Asp Asp Leu Thr Ala Ala Asn Phe Asp Ile Phe Gln Gln Met
            370                 375                 380

<210> SEQ ID NO 7
<211> LENGTH: 230
<212> TYPE: PRT
<213> ORGANISM: Medicago truncatula

<400> SEQUENCE: 7

Met Ser Arg Arg His Ser Cys Ser Leu Lys Gln Lys Leu Arg Lys Gly
1               5                   10                  15

Leu Trp Ser Pro Glu Glu Asp Asp Lys Leu Phe Asn Tyr Ile Thr Met
            20                  25                  30
```

Phe Gly Val Gly Cys Trp Ser Ser Val Pro Lys Leu Ala Gly Leu Gln
            35                  40                  45

Arg Cys Gly Lys Ser Cys Arg Leu Arg Trp Ile Asn Tyr Leu Arg Pro
 50                  55                  60

Asp Leu Lys Arg Gly Met Phe Ser Lys Gln Glu Glu Asp Leu Ile Ile
 65                  70                  75                  80

Asn Leu His Glu Ala Leu Gly Asn Arg Trp Ala Gln Ile Ala Ser Gln
                 85                  90                  95

Leu Pro Gly Arg Thr Asp Asn Glu Ile Lys Asn Phe Trp Asn Ser Ser
                100                 105                 110

Leu Lys Lys Lys Leu Met Lys Gln Gly Ile Asp Pro Ala Thr His Lys
                115                 120                 125

Pro Leu Ile Asn Asn Glu Ser Leu Leu Val Lys Glu Glu Lys Glu Lys
130                 135                 140

Pro Ser Met Ile Met Pro Leu Ser Gln Pro Gln Pro Gln Arg Thr Leu
145                 150                 155                 160

Met Leu Glu Ser Ser His Glu Tyr Ser Glu Ala Leu Leu Met Asn Lys
                165                 170                 175

Pro Thr Phe Asp Leu Asp Pro Leu Gln Leu Gln Phe Glu Leu Asn Gln
                180                 185                 190

Phe Gly Thr Asn Ser Ser Tyr Phe Phe Ser Ser Asp Asn Ile Ser Asn
                195                 200                 205

Asn Ser Phe Ser Asn Met Ile Asn Glu Asn Thr Ala Gly Gly Leu Ile
                210                 215                 220

Ser Trp Glu Gly Glu Asn
225                 230

<210> SEQ ID NO 8
<211> LENGTH: 349
<212> TYPE: PRT
<213> ORGANISM: Medicago truncatula

<400> SEQUENCE: 8

Met Gly Arg His Phe Cys Ser Leu Lys Gln Lys Leu Arg Lys Gly Leu
 1               5                  10                  15

Trp Ser Pro Glu Glu Asp Glu Lys Leu Phe Asn Tyr Ile Thr Met Phe
                20                  25                  30

Gly Val Gly Cys Trp Ser Ser Val Pro Lys Leu Ala Gly Leu Gln Arg
            35                  40                  45

Cys Gly Lys Ser Cys Arg Leu Arg Trp Ile Asn Tyr Leu Arg Pro Asp
 50                  55                  60

Leu Lys Arg Gly Met Phe Ser Lys Gln Glu Glu Asp Leu Ile Ile Asn
 65                  70                  75                  80

Leu His Glu Ala Leu Gly Asn Arg Trp Ala Gln Ile Ala Ala Gln Leu
                 85                  90                  95

Pro Gly Arg Thr Asp Asn Glu Ile Lys Asn Phe Trp Asn Ser Ser Leu
                100                 105                 110

Lys Lys Lys Leu Met Lys Gln Gly Ile Asp Pro Ala Thr His Lys Pro
                115                 120                 125

Phe Ile Asn Asn Ile Glu Ser Leu Ile Lys Glu Lys Glu Lys Pro
130                 135                 140

Ser Met Ile Met Pro Leu Ser His Ser Gln Pro Gln Arg Ile Leu Ala
145                 150                 155                 160

Thr His Thr Met Leu Glu Ser Ser His Asp Tyr Ser Glu Ser Leu Leu

```
                165                 170                 175
Met Ser Asp Leu Ile Asn His Tyr Asn Ile Gly Gly Leu Ala Leu Thr
            180                 185                 190

Glu Ala Ser Arg Ile Phe Leu Met Asn Asn Pro Thr Leu Asp Phe Asp
        195                 200                 205

Pro Leu Tyr Tyr Asn Ser Ser Leu Ile Asn Tyr Tyr Gln Pro Ser Leu
    210                 215                 220

Leu Gln Phe Glu Gln Asn Gln Phe Gly Asn Asn Ser Ser Tyr Phe Phe
225                 230                 235                 240

Ser Ser Met Pro Cys Leu Asn Ser Ser Glu Phe Ser Asp Asn Ile Asn
                245                 250                 255

Asn Ser Val Ser Lys Phe Ser Ser Pro Leu Val Asn Glu Ser Ser Ser
            260                 265                 270

Asn Ser Thr Ser Thr Met Ser Asp Tyr Tyr Gln Ile Ser Asn Met Ile
        275                 280                 285

Asn Glu Asn Ala Gly Gly Leu Ile Ser Trp Glu Gly Glu Glu Phe Ile
    290                 295                 300

Asn Lys Thr Ser Ser Trp Gln Glu Gly Gln Leu Leu Ser His Asn Asn
305                 310                 315                 320

Ser Ile Asp Phe Ser Thr Tyr Pro Leu Thr Ser Leu Ser Glu Asp Leu
                325                 330                 335

Ser Asn Ile Glu Ala Asn Phe Asp Val Phe His His Leu
            340                 345

<210> SEQ ID NO 9
<211> LENGTH: 361
<212> TYPE: PRT
<213> ORGANISM: Medicago truncatula

<400> SEQUENCE: 9

Met Gly Arg His Ser Cys Cys Leu Lys Gln Lys Leu Arg Lys Gly Leu
1               5                   10                  15

Trp Ser Pro Glu Glu Asp Glu Lys Leu Phe Asn His Ile Thr Arg Phe
            20                  25                  30

Gly Val Gly Cys Trp Ser Ser Val Pro Lys Gln Ala Gly Leu Gln Arg
        35                  40                  45

Cys Gly Lys Ser Cys Arg Leu Arg Trp Ile Asn Tyr Leu Arg Pro Asp
    50                  55                  60

Leu Lys Arg Gly Met Phe Ser Gln Gln Glu Glu Asp Leu Ile Ile Ser
65                  70                  75                  80

Leu His Glu Val Leu Gly Asn Arg Trp Ala Gln Ile Ala Ala Gln Leu
                85                  90                  95

Pro Gly Arg Thr Asp Asn Glu Ile Lys Asn Phe Trp Asn Ser Cys Leu
            100                 105                 110

Lys Lys Lys Leu Leu Lys Gln Gly Ile Asp Pro Thr Thr His Lys Pro
        115                 120                 125

Leu Thr Glu Ala Tyr Leu Lys Glu Glu Asn Lys Ile Thr Glu Thr Thr
    130                 135                 140

Val Pro Ser Met Gln Ile Pro Ser Ile Thr Ser His Gly Ser Ala Phe
145                 150                 155                 160

Leu Ile Thr Asp Ser Ser Tyr Tyr Asp Asp Asn Gly Leu Thr Glu Ala
                165                 170                 175

Ser Arg Glu Ile Phe Thr Ser Lys Gln Ala Leu Asp Pro Leu Phe Cys
            180                 185                 190
```

```
Tyr Asp Phe Gln Ser Gly Tyr Asn Leu Pro Met Ser Asn Tyr His Thr
        195                 200                 205

Thr Leu Lys Pro Cys Asp Gln Ser Gln Phe Gly Leu Asn Ser Ser Tyr
    210                 215                 220

Gly Phe Thr Ser Met Pro Ser Leu Thr Asn Ser Asp His Ala Asn Val
225                 230                 235                 240

Ser Val Thr Glu Phe Ser Asp Asn Asn Ser Ala Ser Lys Ile Asn Ser
            245                 250                 255

Phe Phe Met Asn Asp Gln Val Lys Glu Ser Asn Ser Asn Ser Ser
            260                 265                 270

Asn Met Ser Thr Ile Tyr Pro Ser Gln Met Arg Ser Thr Met Met Glu
        275                 280                 285

Asn Asn Asn Ala Gly Phe Cys Trp Asp Gly Ser Glu Lys Asn Ile Asp
290                 295                 300

Pro Leu Phe Gln Phe Gln Val Asn Ala Ile Lys Ser Glu Asp Tyr Gly
305                 310                 315                 320

Thr Ser Ser Trp Glu Glu Gly Gln Leu Gln Thr His Asn Ser Ile Glu
            325                 330                 335

Asp Phe Asn Ser Tyr Pro Leu Thr Ser Leu Ser Glu Asp Leu Thr Glu
            340                 345                 350

Ala Asn Phe Asp Val Phe His His Ile
        355                 360

<210> SEQ ID NO 10
<211> LENGTH: 307
<212> TYPE: PRT
<213> ORGANISM: Musa acuminata

<400> SEQUENCE: 10

Met Gly Arg His Ser Cys Cys Leu Arg Gln Lys Leu Arg Lys Gly Leu
1               5                   10                  15

Trp Ser Pro Glu Glu Asp Glu Lys Leu Tyr Asn His Ile Ile Ala Phe
            20                  25                  30

Gly Val Gly Cys Trp Ser Ser Val Pro Lys Leu Ala Gly Leu Gln Arg
        35                  40                  45

Cys Gly Lys Ser Cys Arg Leu Arg Trp Ile Asn Tyr Leu Arg Pro Asp
    50                  55                  60

Leu Lys Arg Gly Ser Phe Ser Gln Gln Glu Asp Val Ile Ile Gly
65                  70                  75                  80

Leu His Gly Ile Leu Gly Asn Arg Trp Ser Lys Ile Ala Ser Gln Leu
                85                  90                  95

Pro Gly Arg Thr Asp Asn Glu Ile Lys Asn Phe Trp Asn Ser Cys Leu
            100                 105                 110

Lys Lys Lys Leu Arg Leu Arg Gly Ile Asp Pro Thr Thr His Arg Pro
        115                 120                 125

Leu Asn Glu Val Lys Thr Gln Glu Thr Ile Arg Met Tyr Tyr Ser
    130                 135                 140

Asn Ser Gly Ala Asn Phe Glu Gln Leu Pro Glu His Pro Phe Pro Leu
145                 150                 155                 160

Ile Glu Ile Gln Thr Cys Leu Asp Ser Ile Glu Ser Asn Ala Asn Phe
                165                 170                 175

Tyr Tyr Gln Phe His Gln Pro Phe Glu Pro Leu Ser Gln Asn Glu Cys
            180                 185                 190

Leu Val Lys Pro Glu Leu Cys Asp Tyr Gly Gly Val Met Asp Val Pro
        195                 200                 205
```

```
Glu Asn Phe Gly Tyr Gly Glu Ser Ser Asn Ser Gly Asn Trp Asn
    210                 215                 220

Cys Asn Val Val Pro Glu Ile Lys His Val Phe Gly Ser Glu Ala Leu
225                 230                 235                 240

Asn Trp Val Ser Val Ser Lys Ala Glu Thr Leu Val Glu Pro His Glu
                245                 250                 255

His Lys His Ser Ser Trp Arg Glu Cys Gln His Val Met Ser Ser Glu
            260                 265                 270

Asp Phe Ser Thr Glu Pro Val Gly Ser Leu Pro Arg Asp Leu Ser Asp
            275                 280                 285

Ile Cys Phe Asn Val Pro Arg Asp Ala Ser Val Gly Glu Phe Asn Val
    290                 295                 300

Glu Phe Ile
305

<210> SEQ ID NO 11
<211> LENGTH: 336
<212> TYPE: PRT
<213> ORGANISM: Musa acuminata

<400> SEQUENCE: 11

Met Ile Pro Leu Pro Gln Pro Leu Met His Ile Asn Leu Leu Ser Pro
1               5                   10                  15

Ser Thr Ser Arg Asn Thr Arg Arg Gly Phe Gly Gly Met Gly Arg His
                20                  25                  30

Ser Cys Cys Leu Glu Gln Lys Ile Arg Lys Gly Leu Trp Ser Pro Glu
            35                  40                  45

Glu Asp Glu Lys Leu Tyr Asn His Ile Ile Arg Tyr Gly Val Gly Cys
    50                  55                  60

Trp Ser Ser Val Pro Lys Leu Ala Gly Leu Gln Arg Cys Gly Lys Ser
65                  70                  75                  80

Cys Arg Leu Arg Trp Ile Asn Tyr Leu Arg Pro Asp Leu Lys Arg Gly
                85                  90                  95

Asn Phe Ser Gln Gln Glu Glu Asp Leu Ile Ile Ser Leu His Glu Ile
            100                 105                 110

Met Gly Asn Arg Trp Ser Gln Ile Ala Ser Gln Leu Pro Gly Arg Thr
        115                 120                 125

Asp Asn Glu Ile Lys Asn Tyr Trp Asn Ser Cys Leu Lys Lys Lys Leu
    130                 135                 140

Arg Gln Arg Gly Ile Asp Pro Ser Thr His Lys Pro Leu Cys Glu Thr
145                 150                 155                 160

Glu Thr Glu Ala Gln Glu Ala Ser Arg Thr His Leu Glu Gln Leu Pro
                165                 170                 175

Leu Gln Pro Val Phe Asp Pro Phe Pro Leu Ile Glu Thr Glu Thr Cys
            180                 185                 190

Leu Asp Ser Val Glu Asn Asn Val Asn Ile Tyr Asn Gln Phe His Gln
        195                 200                 205

Ser Phe Glu Ser Ser Leu Ala Gln Thr Glu Cys Tyr Ala Asn Ser Gly
    210                 215                 220

Leu Arg Glu Tyr Ser Ser Val Leu Asp Val Tyr Gly Asp Ser Ser Ser
225                 230                 235                 240

Asn Ser Ser Asn Trp Asn Cys Asn Thr Gly Ala Glu Met Lys Asp Val
                245                 250                 255

Val Gly Asp Glu Ala Leu Asn Trp Val Ala Gln Ser Glu Gly Glu Ala
```

```
            260             265             270
Pro Pro His Val His Met Asn Gly Gly Glu Ala His Glu His Lys Phe
        275                 280             285

Ser Pro Trp Gln Glu Lys Thr Asn Ala Glu Ser Ser Glu Asp Tyr Ser
290                 295                 300

Thr Tyr Ser Met Arg Phe Leu Ser Cys Asp Val Ala Glu Thr Cys Phe
305                 310                 315                 320

Asp Ile His Arg Gly Ala Leu Ala Ser Glu Phe Asn Val Asp Phe Phe
                325                 330                 335

<210> SEQ ID NO 12
<211> LENGTH: 308
<212> TYPE: PRT
<213> ORGANISM: Musa acuminata

<400> SEQUENCE: 12

Met Gly Arg His Ser Cys Cys Leu Lys Gln Lys Ile Arg Lys Gly Leu
1               5                   10                  15

Trp Ser Pro Glu Glu Asp Glu Lys Leu Tyr Asp His Ile Ile Arg Cys
                20                  25                  30

Gly Val Gly Cys Trp Ser Ser Val Pro Lys Leu Ala Gly Leu Glu Arg
            35                  40                  45

Cys Gly Lys Ser Cys Arg Leu Arg Trp Ile Asn Tyr Leu Arg Pro Asp
        50                  55                  60

Leu Lys Arg Gly Asn Phe Ser Gln Gln Glu Asp Thr Ile Ile Arg
65                  70                  75                  80

Leu His Glu Ile Met Gly Asn Arg Trp Ser Gln Ile Ala Ser Gln Leu
                85                  90                  95

Pro Gly Arg Thr Asp Asn Glu Ile Lys Asn Tyr Trp Asn Ser Cys Leu
            100                 105                 110

Lys Lys Lys Leu Arg Gln Arg Gly Ile Asp Pro Ser Ser His Lys Pro
        115                 120                 125

Leu Ser Glu Ile Ala Ala Gln Glu Glu Gly Thr Arg Thr His Cys Ser
130                 135                 140

Asn Thr Gly Ala Ala Phe Glu Gln Leu Gln Leu His Pro Val Phe Asp
145                 150                 155                 160

Thr Phe Pro Leu Ile Glu Ile Gln Thr Cys Leu Asp Ser Val Glu Thr
                165                 170                 175

Asn Val Ser Ile Tyr Gly Gln Phe His Gln Thr Phe Glu Pro Val Gly
            180                 185                 190

Gln Asp Glu Cys Leu Val Asn Leu Glu Leu Cys Asp His Gly Ser Ala
        195                 200                 205

Leu Asp Asn Ile Gly His Gly Asp Ser Ser Ile Asn Ser Ser Asn Trp
210                 215                 220

Asn Cys Asn Ile Gly Ser Glu Met Lys Ser Val Phe Gly Asp Glu Asp
225                 230                 235                 240

Leu Asn Trp Val Ser Gln Ser Lys Val Glu Thr Pro Ala His Met Gln
                245                 250                 255

Met Asn Glu Glu Lys Thr His Glu His Lys Phe Asn His Trp Gln Glu
            260                 265                 270

Lys Asn Thr Tyr Pro Ile Pro Val Arg Ser Leu Ser His Asp Leu Ser
        275                 280                 285

Glu Thr Cys Phe Ser Val Ser Arg Asp Ala Met Glu Ser Glu Phe Asn
290                 295                 300
```

Val Asp Phe Cys
305

<210> SEQ ID NO 13
<211> LENGTH: 312
<212> TYPE: PRT
<213> ORGANISM: Oryza sativa

<400> SEQUENCE: 13

Met Gly Arg Leu Ser Ser Cys Gly Gly Val Gln Ala Lys Leu Arg Lys
1               5                   10                  15

Gly Leu Trp Ser Pro Glu Glu Asp Asp Lys Leu Tyr Asn His Ile Ile
                20                  25                  30

Arg His Gly Val Gly Cys Trp Ser Ser Val Pro Lys Leu Ala Gly Leu
            35                  40                  45

Gln Arg Cys Gly Lys Ser Cys Arg Leu Arg Trp Ile Asn Tyr Leu Arg
    50                  55                  60

Pro Asp Leu Lys Arg Gly Ser Phe Ser Gln Gln Glu Glu Asp Leu Ile
65                  70                  75                  80

Val Ala Leu His Glu Ile Leu Gly Asn Arg Trp Ser Gln Ile Ala Ser
                85                  90                  95

His Leu Pro Gly Arg Thr Asp Asn Glu Ile Lys Asn Phe Trp Asn Ser
            100                 105                 110

Cys Leu Lys Lys Lys Leu Arg Gln Arg Gly Leu Asp Pro Ala Thr His
        115                 120                 125

Lys Pro Ile Ala Ala Ala Ala Ala Ala Thr Ser Ser Glu Ser Ala
130                 135                 140

Val Thr Gln Val Asp Glu Asp His Lys Pro His Gly Ala Ala Ala Ala
145                 150                 155                 160

Ala Ala Ala Ala Asp Gly Leu Ala Ala Asn Ala Lys Gln Ser Val Phe
                165                 170                 175

Asp Pro Phe Pro Val Thr Asp Phe Gly Ala Gly Phe Asp Leu Gly Ala
            180                 185                 190

Ala Asn Met Ala Ala Ala Leu Tyr Gly Ser His Pro Asp Asp Gly Ala
        195                 200                 205

Gly Phe Val Ala Asp Tyr Ser Ser Val Leu Asp Val Ser Glu Asn Leu
    210                 215                 220

Gly Tyr Gly Glu Ser Ser Asn Ser Ser Asn Trp Thr Cys Ala Glu
225                 230                 235                 240

Val Ser Asn Val Leu Asp Ser Glu Val Leu Asn Trp Ala Ala Ser Ala
                245                 250                 255

Gly Ala Asp Ala Ala Lys Ala Glu Pro Phe Ala Asp Met Glu Gln
            260                 265                 270

Gln His Ser Gly Tyr Gly Gly Tyr Gln Val Glu Asp Asp Ala Thr
        275                 280                 285

Leu Glu His Lys Phe Ser Leu Pro Cys His Glu Gln Ser Leu Ala Gln
    290                 295                 300

Phe Asp Phe Asn Leu Glu Tyr Phe
305                 310

<210> SEQ ID NO 14
<211> LENGTH: 357
<212> TYPE: PRT
<213> ORGANISM: Oryza sativa

<400> SEQUENCE: 14

Met Gly Arg Glu Ser Ala Ala Cys Ser Pro Lys Pro Lys Leu Arg
1               5                   10                  15

Arg Gly Leu Trp Ser Pro Glu Asp Glu Lys Leu Phe Asn His Ile
            20                  25                  30

Ser Arg Tyr Gly Val Gly Cys Trp Ser Val Pro Lys Leu Ala Gly
            35                  40                  45

Leu Glu Arg Cys Gly Lys Ser Cys Arg Leu Arg Trp Ile Asn Tyr Leu
50                  55                  60

Arg Pro Asp Leu Lys Arg Gly Ser Phe Ser Gln Glu Glu Glu Leu
65                  70                  75                  80

Ile Ile Ser Leu His Lys Ile Leu Gly Asn Arg Trp Ser Gln Ile Ala
                85                  90                  95

Ala Gln Leu Pro Gly Arg Thr Asp Asn Glu Ile Lys Asn Phe Trp Asn
            100                 105                 110

Ser Cys Leu Lys Lys Lys Leu Arg Gln Arg Gly Ile Asp Pro Ala Thr
                115                 120                 125

His Lys Pro Leu Asn Asp Gly Ala Gly Ala Gly Glu Glu His His
    130                 135                 140

Asp Asp Gly Asp Lys Gln Gln Leu Met Asp Asp Val Asp Asp Cys Phe
145                 150                 155                 160

Ala Ile Gly Gly Gly Gly Ser Ser Asp Ser Leu Ala Pro Pro His Ser
                165                 170                 175

Pro Ala Val Ser Phe Asp Pro Leu Ser Val Thr Asn Val Pro Thr Thr
            180                 185                 190

Met Met Gln Ser Ser Ser Ser Pro Tyr Gly Ala Gly Gly Glu His
    195                 200                 205

Ser Ser Phe Arg Ser Asp Thr Leu Cys Asp Tyr Gly Gly Ser Gly Gly
    210                 215                 220

Gly Val Asp Val Val Ser Asp Ala Gly Thr Tyr Ser Ala Tyr Thr Gly
225                 230                 235                 240

Asp Ser Ser Ser Asn Ser Asn Ser Thr Ala Trp Thr Cys Gly Ser Val
                245                 250                 255

Val Val Gly Gly Ala Gly Glu Leu Pro Pro Pro Leu Leu Pro His
    260                 265                 270

Met Asp Met Phe Gly Arg Val Asp Ala Glu Pro Pro Tyr Pro Pro
    275                 280                 285

Phe Asp Val Gln Ala Arg Phe Ser Pro Trp His His His His His
    290                 295                 300

His His Glu Pro Thr Leu Pro Thr Pro Gln Arg Leu Asp Gly Gly
305                 310                 315                 320

Gly Gly Ala Ala Ala Ser Phe Pro Ile Arg Ser Leu Ser Arg Asp Met
            325                 330                 335

Pro Glu Ser Cys Phe Asp Leu Gly Arg Gly Ala Leu Asp Asp Glu Phe
                340                 345                 350

Gly Val Asp Phe Leu
        355

<210> SEQ ID NO 15
<211> LENGTH: 301
<212> TYPE: PRT
<213> ORGANISM: Oryza sativa

<400> SEQUENCE: 15

Met Gly Arg His Ala Cys Ser Ala Ala Gly Val Gln Gln Lys Leu Arg
1               5                   10                  15

```
Lys Gly Leu Trp Ser Pro Glu Glu Asp Glu Lys Leu Tyr Asn His Ile
            20                  25                  30

Tyr Arg Tyr Gly Val Gly Cys Trp Ser Ser Val Pro Lys Leu Ala Gly
            35                  40                  45

Leu Gln Arg Cys Gly Lys Ser Cys Arg Leu Arg Trp Ile Asn Tyr Leu
 50                  55                  60

Arg Pro Asp Leu Lys Arg Gly Ser Phe Ser Gln Gln Glu Asp Ala
65                  70                  75                  80

Ile Val Gly Leu His Glu Ile Leu Gly Asn Arg Trp Ser Gln Ile Ala
                    85                  90                  95

Ser His Leu Pro Gly Arg Thr Asp Asn Glu Ile Lys Asn Phe Trp Asn
                100                 105                 110

Ser Cys Leu Lys Lys Lys Leu Arg Gln Arg Gly Ile Asp Pro Ser Thr
                115                 120                 125

His Gln Pro Ile Ser Thr Ala Ala Ala Ala Ala Ala Ala Leu Asp
        130                 135                 140

Thr Ser Thr Gln Asp Gln Lys Pro Pro Ala Thr Ala Asp Gly Phe Ala
145                 150                 155                 160

Leu Lys Gln Gln Gln Gln Val Phe Asp Pro Phe Pro Val Ile Asp Ser
                165                 170                 175

Phe Gly Ser Gly Phe Asp Ala Thr Gly Met Pro Leu Tyr Gly His Leu
                180                 185                 190

Gly Gly Lys Asp Ala Ala Gly Phe Val Asp Tyr Ser Ser Val Leu Asp
            195                 200                 205

Val Ser Glu Asn Leu Gly Tyr Gly Glu Ser Ser Asn Ser Ser Asn
    210                 215                 220

Trp Asn Cys Gly Val Gly Ala Pro Glu Val Asn Asn Ala Leu Glu Ser
225                 230                 235                 240

Glu Pro Leu His Trp Ala Thr Glu Ser Lys Val Glu Pro Phe Val Gly
                245                 250                 255

Tyr Gly Glu Gly Asp Ala Met Glu His Lys Phe Gly Leu Pro Cys His
            260                 265                 270

Gly Gln Gln Glu Gln Gly Met Thr His Phe Asp Phe Asp Val Ser Arg
            275                 280                 285

Ser Met Val Val Gly Asp Phe Asn Phe Glu Tyr Phe Arg
290                 295                 300

<210> SEQ ID NO 16
<211> LENGTH: 306
<212> TYPE: PRT
<213> ORGANISM: Panicum virgatum

<400> SEQUENCE: 16

Met Gly Arg Leu Ser Cys Gly Gly Val Gln Pro Lys Leu Arg Lys
1                 5                  10                  15

Gly Leu Trp Ser Pro Glu Glu Asp Glu Lys Leu Tyr Asn His Ile Ile
            20                  25                  30

Arg His Gly Val Gly Cys Trp Ser Ser Val Pro Lys Leu Ala Gly Leu
            35                  40                  45

Gln Arg Cys Gly Lys Ser Cys Arg Leu Arg Trp Ile Asn Tyr Leu Arg
 50                  55                  60

Pro Asp Leu Lys Arg Gly Ser Phe Ser Gln Gln Glu Asp Leu Ile
65                  70                  75                  80

Leu Ala Leu His Glu Ile Leu Gly Asn Arg Trp Ser Gln Ile Ala Ser
```

```
                85                  90                  95
His Leu Pro Gly Arg Thr Asp Asn Glu Ile Lys Asn Phe Trp Asn Ser
            100                 105                 110

Cys Leu Lys Lys Lys Leu Arg Gln Arg Gly Ile Asp Pro Ser Thr His
            115                 120                 125

Lys Pro Ile Ala Gly Ala Gly Ala Val Asp His Asp Arg Lys
130             135                 140

Pro Ala Ala Gly Asp Ser Asp Glu Gly Leu Ala Gln Lys Gln Pro Ala
145                 150                 155                 160

Val Phe Asp Pro Phe Pro Leu Ala Asp Phe Gly Phe Asp Leu Gly Ala
                165                 170                 175

Ala Gly Val Ala Ala Leu Tyr Cys Gly Pro Tyr Asp Asp Gly Val Gly
                180                 185                 190

Lys Ala Ser Pro Asp Ala Gly Trp Phe Val Ala Asp Tyr Ser Ser Val
                195                 200                 205

Leu Asp Val Ser Glu Asn Leu Gly Tyr Gly Glu Ser Ser Ser Asn Ser
            210                 215                 220

Ser Asn Trp Thr Cys Ala Glu Met Ser Ser Ala Val Leu Asp Ser Glu
225                 230                 235                 240

Val Leu His Trp Ala Ser Gly Gly Ala Ala Lys Pro Glu Pro Tyr
                245                 250                 255

Thr Glu Leu Glu Gln Gln Gln Arg Ser Gly Tyr Gly Gly Gly Glu
            260                 265                 270

Gln Ala Val Asp Asp Asp Asp Ala Leu Glu His Lys Phe Ser Leu
                275                 280                 285

Pro Cys Gly Gln Glu Gln Ser Leu Ala His Phe Asp Phe Asn Leu Glu
            290                 295                 300

Tyr Phe
305

<210> SEQ ID NO 17
<211> LENGTH: 319
<212> TYPE: PRT
<213> ORGANISM: Panicum virgatum

<400> SEQUENCE: 17

Met Gly Arg Glu Ala Ala Ala Ala Arg Pro Lys Leu Arg Arg Gly
1               5                   10                  15

Leu Trp Ser Pro Glu Glu Asp Glu Lys Leu Tyr Asn His Ile Ile Arg
                20                  25                  30

Tyr Gly Val Gly Cys Trp Ser Val Pro Lys Leu Ala Gly Leu Glu
                35                  40                  45

Arg Cys Gly Lys Ser Cys Arg Leu Arg Trp Ile Asn Tyr Leu Arg Pro
50                  55                  60

Asp Leu Lys Arg Gly Ser Phe Ser Gln Gln Glu Glu Asp Leu Ile Ile
65                  70                  75                  80

Ser Leu His Lys Ile Leu Gly Asn Arg Trp Ser Gln Ile Ala Ser Gln
                85                  90                  95

Leu Pro Gly Arg Thr Asp Asn Glu Ile Lys Asn Phe Trp Asn Ser Cys
            100                 105                 110

Ile Lys Lys Lys Leu Arg Gln Arg Gly Ile Asp Pro Ala Thr His Lys
        115                 120                 125

Pro Leu Glu Asp Asp Ala Ala Ala Ala Ala Asn Ser Gly Glu Ala
130                 135                 140
```

```
Pro Arg Asp Asp Cys Asn Lys Leu Leu Pro Ala Thr Ala Asp Asp His
145                 150                 155                 160

Cys Gly Phe Ala Met Gly Gly Ala Ser Ser Asp Pro Leu Ala Pro His
                165                 170                 175

Ser Pro Thr Val Ser Phe Asp Pro Leu Ser Val Thr Asn Val Pro Ala
            180                 185                 190

Met Gln Gly Ser Tyr Gly Ala Ala His Ser Phe Gln Pro Asp Asn Leu
        195                 200                 205

Cys Asp Tyr Gly Gly Ala Ala Tyr Ser Ala Ala Tyr Thr Gly
    210                 215                 220

Gly Gly Ala Asp Ser Ser Asn Ser Asn Gly Thr Trp Thr Cys Gly
225                 230                 235                 240

Asn Ala Val Gly Gly Glu Pro Met Pro Gln Leu Asp Met Phe Gly Arg
                245                 250                 255

Glu Ala Tyr His Gln Phe Asp Pro Ala Asn Lys Tyr Ser Pro Trp Gln
                260                 265                 270

Gln His Glu Ala Ala Arg Leu His Asp Gly Ile Gly Gly Ala Ala Gly
            275                 280                 285

Phe Pro Ile Arg Ser Met Ser Arg Asp Leu Pro Asp Ser Cys Phe Asp
290                 295                 300

Leu Ala Arg Ser Gly Leu Glu Asp Glu Phe Ser Val Asp Phe Leu
305                 310                 315
```

<210> SEQ ID NO 18
<211> LENGTH: 316
<212> TYPE: PRT
<213> ORGANISM: Panicum virgatum

<400> SEQUENCE: 18

```
Met Gly Arg Leu Ser Cys Gly Gly Val Gln Pro Lys Leu Arg Lys
1               5                   10                  15

Gly Leu Trp Ser Pro Glu Glu Asp Glu Lys Leu Tyr Asn His Ile Ile
                20                  25                  30

Arg His Gly Val Gly Cys Trp Ser Ser Val Pro Lys Leu Ala Gly Leu
            35                  40                  45

Gln Arg Cys Gly Lys Ser Cys Arg Leu Arg Trp Ile Asn Tyr Leu Arg
50                  55                  60

Pro Asp Leu Lys Arg Gly Ser Phe Ser Gln Gln Glu Gly Asp Leu Ile
65                  70                  75                  80

Leu Ala Leu His Glu Ile Leu Gly Asn Arg Trp Ser Gln Ile Ala Ser
                85                  90                  95

His Leu Pro Gly Arg Thr Asp Asn Glu Ile Lys Asn Phe Trp Asn Ser
            100                 105                 110

Cys Leu Lys Lys Lys Leu Arg Gln Arg Gly Ile Asp Pro Ser Thr His
        115                 120                 125

Lys Pro Ile Ala Gly Ala Ala Glu Val Gly Ala Ala Leu Pro Asp Ala
    130                 135                 140

Arg Asp His Asp His Lys Pro Ala Ala Ala Gly Asp Ser Asp Asp
145                 150                 155                 160

Gly Leu Ala Gln Lys Gln Pro Ala Val Phe Asp Pro Phe Pro Leu Ala
                165                 170                 175

Asp Phe Gly Phe Asp Leu Gly Ala Ala Gly Val Ala Ala Leu Tyr Cys
            180                 185                 190

Gly Pro Tyr Asp Asp Gly Val Gly Lys Ala Ser Pro Asp Ala Gly Gly
        195                 200                 205
```

```
Phe Val Ala Asp Tyr Ser Ser Val Leu Asp Val Ser Glu Asn Leu Gly
            210                 215                 220

Tyr Gly Glu Ser Ser Ser Asn Ser Ser Asn Trp Thr Cys Ala Glu Met
225                 230                 235                 240

Ser Ser Ala Val Leu Asp Ser Glu Val Leu His Trp Ala Ser Gly Gly
                245                 250                 255

Gly Gly Gly Gly Ala Ala Lys Pro Glu Pro Tyr Thr Glu Leu Glu Arg
            260                 265                 270

Gln Gln His Ser Gly Gly Tyr Gly Gly Val Glu Gln Ala Val Asp Asp
        275                 280                 285

Asp Asp Ala Leu Glu His Lys Phe Ser Leu Pro Cys Gly Gln Glu Gln
    290                 295                 300

Ser Leu Ala His Phe Asp Phe Asn Leu Glu Tyr Phe
305                 310                 315

<210> SEQ ID NO 19
<211> LENGTH: 325
<212> TYPE: PRT
<213> ORGANISM: Panicum virgatum

<400> SEQUENCE: 19

Met Gly Arg Glu Ala Ala Ala Arg Pro Lys Leu Arg Arg Gly Leu
1               5                   10                  15

Trp Ser Pro Glu Glu Asp Glu Lys Leu Tyr Asn His Ile Ile Arg Tyr
                20                  25                  30

Gly Val Gly Cys Trp Ser Ser Val Pro Lys Leu Ala Gly Leu Glu Arg
            35                  40                  45

Cys Gly Lys Ser Cys Arg Leu Arg Trp Ile Asn Tyr Leu Arg Pro Asp
    50                  55                  60

Leu Lys Arg Gly Ser Phe Ser Gln Gln Glu Glu Asp Leu Ile Ile Asn
65                  70                  75                  80

Leu His Lys Ile Leu Gly Asn Arg Trp Ser Gln Ile Ala Ser Gln Leu
                85                  90                  95

Pro Gly Arg Thr Asp Asn Glu Ile Lys Asn Phe Trp Asn Ser Cys Ile
            100                 105                 110

Lys Lys Lys Leu Arg Gln Arg Gly Ile Asp Pro Ala Thr His Lys Pro
    115                 120                 125

Leu Glu Asp Asp Asp Asp Ala Ala Ala Ala Asn Ser Gly Glu Ala
130                 135                 140

Ala Arg Asp Asp Ser Lys Gln Leu Pro Ala Ala Ser Asp Asp His Cys
145                 150                 155                 160

Gly Phe Ala Met Gly Gly Ala Cys Ser Asp Pro Leu Ala Pro His Ser
                165                 170                 175

Pro Thr Val Ser Phe Asp Pro Leu Ser Val Thr Asn Val Pro Glu Met
            180                 185                 190

Gln Gly Ser Tyr Gly Ala Ala His Ser Phe Arg Pro Asp Asn Leu Cys
    195                 200                 205

Asp Tyr Gly Gly Val Asp Ala Ala Ser Glu Gly Ala Ala Ala Tyr Ser
    210                 215                 220

Ala Ala Ala Tyr Thr Gly Gly Gly Val Asp Ser Ser Asn Ser Asn
225                 230                 235                 240

Gly Thr Trp Thr Cys Gly Asn Val Val Gly Gly Glu Pro Met Gln Gln
                245                 250                 255

Leu Asp Met Phe Gly Gly Arg Glu Ala Tyr His Gln Phe Asp Pro Ala
```

```
            260                 265                 270
Lys Tyr Ser Leu Trp Gln Gln His Glu Ala Ala Arg Leu His Asp Gly
            275                 280                 285

Val Gly Gly Ala Thr Gly Phe Pro Ile Arg Ser Met Ser Arg Asp Leu
            290                 295                 300

Pro Asp Ser Cys Phe Asp Leu Ala Arg Ser Gly Leu Glu Asp Glu Phe
305                 310                 315                 320

Ser Val Asp Phe Leu
            325

<210> SEQ ID NO 20
<211> LENGTH: 370
<212> TYPE: PRT
<213> ORGANISM: Populus trichocarpa

<400> SEQUENCE: 20

Met Gly Arg His Ser Cys Cys Leu Lys Gln Lys Leu Arg Lys Gly Leu
1               5                   10                  15

Trp Ser Pro Glu Glu Asp Glu Arg Leu Phe Asn Tyr Ile Thr Arg Phe
            20                  25                  30

Gly Val Gly Cys Trp Ser Ser Val Pro Lys Leu Ala Gly Leu Gln Arg
            35                  40                  45

Cys Gly Lys Ser Cys Arg Leu Arg Trp Ile Asn Tyr Leu Arg Pro Asp
        50                  55                  60

Leu Lys Arg Gly Met Phe Ser Gln Gln Glu Glu Asp Leu Ile Ile Ser
65                  70                  75                  80

Phe His Glu Val Leu Gly Asn Arg Trp Ala Gln Ile Ala Ala Gln Leu
                85                  90                  95

Pro Gly Arg Thr Asp Asn Glu Ile Lys Asn Phe Trp Asn Ser Cys Leu
            100                 105                 110

Lys Lys Lys Leu Met Lys Gln Gly Ile Asp Pro Ala Thr His Lys Pro
        115                 120                 125

Leu Ser Gln Val Glu Val Lys Glu Glu Lys Ile Cys Thr Glu Lys Ala
130                 135                 140

Ser Phe Gln Ile Pro Gln Ser Lys Gly Leu Pro Ile Leu Ser Asn Phe
145                 150                 155                 160

Ser Ala Pro Glu Pro Ala Phe Ile Ile Asn Asp Thr Ala Tyr Asn Ser
                165                 170                 175

Ser Gly Leu Thr Glu Ala Ser Arg Glu Gln Phe Ile Asn Lys Gln Ala
            180                 185                 190

Tyr Asp Pro Ile Ala Tyr Phe Glu Phe Pro Ser Ile Val Pro Thr
        195                 200                 205

Gly Tyr Asn Ser Asn Leu Ser Ser Val Tyr His Pro Thr Val Arg Pro
210                 215                 220

Leu Asp Gln Asn Gln Phe Glu Thr Ser Ser Asn Phe Val Phe Thr Ser
225                 230                 235                 240

Met Pro Ser Leu Thr Ser Phe Asp His Gly Ser Met Ser Gly Thr Asp
                245                 250                 255

Phe Ser Asp Asn Ser Ala Ser Arg Met Ser Ser Met Phe Leu Asn Glu
            260                 265                 270

Ala Lys Glu Ser Ser Ser Asn Ser Ser Asn Ile Ser Asn Tyr Ala Gly
        275                 280                 285

Tyr Gln Met Ser Asn Met Val Glu Asn Ala Ala Gly Phe Ser Ser Trp
290                 295                 300
```

Asp Ser Asp Asp Lys Leu Glu Ser Val Phe Gln Tyr His Gln Val Asn
305                 310                 315                 320

Gly Ile Lys Thr Gly Glu Leu Lys Pro Ser Pro Trp His Asp Ala Gly
            325                 330                 335

Gln Leu His Thr His Gln Asn Ser Val Asp Phe Ser Ser Cys Pro Leu
            340                 345                 350

Lys Ser Leu Ser Glu Asp Leu Lys Gly Ala Asn Phe Asp Gly Phe His
        355                 360                 365

Gln Ile
    370

<210> SEQ ID NO 21
<211> LENGTH: 371
<212> TYPE: PRT
<213> ORGANISM: Populus trichocarpa

<400> SEQUENCE: 21

Met Gly Arg His Ser Cys Cys Leu Lys Gln Lys Leu Arg Lys Gly Leu
1               5                   10                  15

Trp Ser Pro Glu Glu Asp Glu Lys Leu Leu Asn Tyr Ile Thr Arg Phe
            20                  25                  30

Gly Val Gly Cys Trp Ser Ser Val Pro Lys Leu Ala Gly Leu Gln Arg
        35                  40                  45

Cys Gly Lys Ser Cys Arg Leu Arg Trp Ile Asn Tyr Leu Arg Pro Asp
    50                  55                  60

Leu Lys Arg Gly Met Phe Ser Gln Gln Glu Asp Leu Ile Ile Ser
65                  70                  75                  80

Leu His Glu Val Leu Gly Asn Arg Trp Ala Gln Ile Ala Ala Gln Leu
                85                  90                  95

Pro Gly Arg Thr Asp Asn Glu Ile Lys Asn Leu Trp Asn Ser Tyr Leu
            100                 105                 110

Lys Lys Lys Leu Met Lys Gln Gly Ile Asp Pro Thr Thr His Lys Pro
        115                 120                 125

Leu Cys Gln Val Gly Val Lys Glu Lys Asp Cys Thr Glu Lys Ala
    130                 135                 140

Ser Phe Gln Ile Pro Gln Ser Lys Gly Leu Pro Ile Val Ser Asn Phe
145                 150                 155                 160

Thr Ala Gln Glu Pro Ala Phe Leu Ile Asn Asp Thr Thr Tyr Asn Ser
                165                 170                 175

Ser Gly Leu Pro Glu Val Ser Arg Glu Gln Phe Leu Asn Lys Gln Ala
            180                 185                 190

Tyr Asp Pro Leu Ser Tyr Phe Glu Phe Pro Ala Gly Ile Asp Leu Thr
        195                 200                 205

Gly Tyr Asn Pro Ser Leu Ser Val Tyr His Pro Thr Val Arg Ser
    210                 215                 220

Leu Asp Gln Asn Gln Phe Glu Thr Ser Ser Asn Phe Gly Phe Thr Ser
225                 230                 235                 240

Met Pro Ser Leu Thr Ser Phe Asp His Gly Ser Met Ser Gly Thr Asp
                245                 250                 255

Phe Ser Asp Asn Ser Ala Ser Arg Met Ser Ser Met Phe Leu Asn Glu
            260                 265                 270

Ala Lys Glu Ser Ser Ser Asn Ser Ser Asn Ile Ser Asn Tyr Ala Gly
        275                 280                 285

Tyr Gln Met Asn Asn Met Val Glu Asn Ala Ala Ala Phe Ser Ser Trp
    290                 295                 300

Asp Ser Asp Asp His Lys Leu Glu Ser Val Phe Gln Tyr His Gln Val
305                 310                 315                 320

Asn Gly Val Lys Thr Glu Glu Leu Lys Pro Ser Pro Trp His Glu Ala
            325                 330                 335

Gly Arg Leu His Thr His Gln Asn Ser Val Asp Phe Asn Ser Tyr Pro
            340                 345                 350

Leu Thr Ser Leu Ser Glu Asp Ile Thr Gly Ala Asn Phe Asp Val Phe
            355                 360                 365

His Gln Ile
    370

<210> SEQ ID NO 22
<211> LENGTH: 384
<212> TYPE: PRT
<213> ORGANISM: Prunus persica

<400> SEQUENCE: 22

Met Gly Arg His Ser Cys Cys Leu Lys Gln Lys Leu Arg Lys Gly Leu
1               5                   10                  15

Trp Ser Pro Glu Glu Asp Glu Lys Leu Phe Asn Tyr Ile Thr Arg Phe
            20                  25                  30

Gly Val Gly Cys Trp Ser Ser Val Pro Lys Leu Ala Gly Leu Gln Arg
        35                  40                  45

Cys Gly Lys Ser Cys Arg Leu Arg Trp Ile Asn Tyr Leu Arg Pro Asp
50                  55                  60

Leu Lys Arg Gly Met Phe Ser Gln Gln Glu Glu Asp Leu Ile Ile Ser
65                  70                  75                  80

Leu His Glu Val Leu Gly Asn Arg Trp Ala Gln Ile Ala Ala Gln Leu
                85                  90                  95

Pro Gly Arg Thr Asp Asn Glu Ile Lys Asn Phe Trp Asn Ser Cys Leu
            100                 105                 110

Lys Lys Lys Leu Leu Lys Gln Gly Ile Asp Pro Thr Thr His Lys Pro
        115                 120                 125

Leu Ser Glu Glu Glu Met Lys Glu Lys Lys Ser Met Asp Cys Ser Glu
130                 135                 140

Leu Lys Glu Cys Leu Pro Met Pro Glu His Glu Gln Gly Leu Pro Thr
145                 150                 155                 160

Ile Pro Ala Met Ser Ser Ser Gln Gly Pro Thr Phe Leu Val Asn Asp
                165                 170                 175

Ser Asn Tyr Phe Asp Gly Ala Gly Val Leu Thr Gln Ala Ser Arg Ala
            180                 185                 190

Phe Asp Ser Leu Ser Tyr Phe Glu Phe Gln Thr Gly Ile Glu Pro Ser
        195                 200                 205

Gly Tyr Asn Ser Asp Leu Val Ser Thr Gln Tyr His Pro Thr Asn Val
210                 215                 220

Arg Pro His Phe Asn Gln Pro His Asn Thr Thr Tyr Glu Thr Ser Ser
225                 230                 235                 240

Asn Phe Gly Phe Thr Ser Met Pro Ser Leu Ala Asn Ser Asp His Gly
                245                 250                 255

Ser Met Ser Gly Thr Asp Phe Ser Asp Asn Ser Ala Ser Arg Leu Ser
            260                 265                 270

Ser Phe Phe Met Asn Glu Val Lys Glu Cys Ser Ser Asn Ser Ser Asn
        275                 280                 285

Val Ser Ser Tyr Ala Ala Gly Phe His Met Asn Asn Asn Ser Asn Asn

```
                290                 295                 300
Asn Asn Asn Asn Asn Val Val Glu Asn Ala Ala Phe Ser Trp Asp Thr
305                 310                 315                 320

Asp Asn Lys Leu Asp Ser Leu Phe Gln Phe His Ala Asn Gly Ile Lys
                325                 330                 335

Ser Glu Glu Leu Ile Lys Pro Asn Ser Trp Gln Gln Gly Gln Gln Leu
                340                 345                 350

Leu His Ala Gln Asn Ser Val Asp Phe Asn Ser Tyr Pro Leu Thr Ser
                355                 360                 365

Leu Ser Glu Asp Leu Thr Gly Ala Asn Phe Asp Val Phe Gln His Ile
                370                 375                 380

<210> SEQ ID NO 23
<211> LENGTH: 325
<212> TYPE: PRT
<213> ORGANISM: Solanum tuberosum

<400> SEQUENCE: 23

Met Gly Arg His Ser Cys Ser Val Lys Gln Lys Leu Arg Lys Gly Leu
1               5                   10                  15

Trp Ser Pro Glu Glu Asp Glu Lys Leu Cys Asn Tyr Ile Thr Asn Phe
                20                  25                  30

Gly Ile Gly Ser Trp Ser Ser Val Pro Lys Leu Ala Gly Leu Gln Arg
            35                  40                  45

Cys Gly Lys Ser Cys Arg Leu Arg Trp Ile Asn Tyr Leu Arg Pro Asp
        50                  55                  60

Leu Lys Arg Gly Met Phe Ser Gln Asp Glu Asp Lys Ile Ile Ser
65                  70                  75                  80

Leu His Gln Val Leu Gly Asn Arg Trp Ala Gln Ile Ala Ala Gln Leu
                85                  90                  95

Pro Gly Arg Thr Asp Asn Glu Ile Lys Asn Phe Trp Asn Ser Ser Leu
            100                 105                 110

Lys Lys Lys Leu Met Lys Gln Gly Ile Asp Pro Asn Thr His Lys Pro
        115                 120                 125

Leu Lys Glu Asn Gln Val Ile Lys Asp Glu Asn Cys Thr Asn Lys
    130                 135                 140

Thr Ser Met Leu Gln Ile Pro Pro His Leu Asn Glu Met Ala Asn Gly
145                 150                 155                 160

Gln Phe Thr Glu Ser Lys Gln Val Phe Asp Leu Leu Phe Val Pro Asp
                165                 170                 175

Phe Gln Ser Asn Ser Asn Pro Ser Glu Tyr Asn Ser Glu Val Leu Ala
            180                 185                 190

Gln Tyr His Asp Gln Gln Ser Glu Phe Glu Asn Asn Pro Asn Tyr Val
        195                 200                 205

Phe Cys Ser Ala Ser Ser Val Thr Lys Leu Glu His Gly Gln Met Thr
    210                 215                 220

Glu Thr Asp Phe Gly Ser Ser Thr Ser Arg Met Ser Ser Ser Asn
225                 230                 235                 240

Ser Ser Asn Met Cys Ser Asn Gln Asn Thr Ala Gly Ile Gln Ile Asn
                245                 250                 255

Gly Met Ser Glu Asn Ser Glu Ala Leu Ser Trp Asp Ile Glu Asn Lys
            260                 265                 270

Met Glu Ser Leu Phe Gln Tyr Pro Tyr Ile Gly Ile Lys Asn Glu Glu
        275                 280                 285
```

Leu Lys Ser Ser Pro Ser Gln Glu Arg Asp Gln Leu Tyr Gly Asn Ser
        290                 295                 300

Thr Ser Gly Asp Phe Met Ser Asn Tyr Pro Leu Ser Ser Leu Thr Glu
305                 310                 315                 320

Glu Phe Lys Trp Gly
            325

<210> SEQ ID NO 24
<211> LENGTH: 315
<212> TYPE: PRT
<213> ORGANISM: Solanum tuberosum

<400> SEQUENCE: 24

Met Gly Arg His Ser Val Phe Val Lys Glu Lys Thr Arg Lys Gly Leu
1               5                   10                  15

Trp Ser Pro Glu Glu Asp Glu Lys Leu Tyr Asn Tyr Ile Thr Arg Phe
            20                  25                  30

Gly Val Gly Cys Trp Ser Ser Val Pro Lys Leu Ala Gly Leu Gln Arg
        35                  40                  45

Cys Gly Lys Ser Cys Arg Leu Arg Trp Ile Asn Tyr Leu Arg Pro Asp
    50                  55                  60

Leu Lys Arg Gly Met Phe Ser Gln Glu Glu Asp Met Ile Ile Thr
65                  70                  75                  80

Leu His Lys Val Val Gly Asn Arg Trp Ala Gln Ile Ala Ala Lys Leu
                85                  90                  95

Pro Gly Arg Thr Asp Asn Glu Ile Lys Asn Phe Trp Asn Ser Asn Leu
            100                 105                 110

Lys Lys Lys Leu Ile Lys Gln Gly Ile Asp Pro Asn Thr His Lys Pro
        115                 120                 125

Leu Ser Glu Asn His Gln Val Arg Asn Glu Thr Asn Tyr Thr Asp Lys
    130                 135                 140

Ala Ser Ser Leu Leu Pro Asn Met Ser Asn Ser Ala Glu Ile Glu Gln
145                 150                 155                 160

Pro Phe His Phe Asn Ser Lys Arg Ser Phe Asn Ser Glu Ala Ile Thr
                165                 170                 175

Arg Gln Leu Thr Glu Val Ser Arg Asn Gln Leu Val Ser Lys Gln Val
            180                 185                 190

Phe Asp Pro Leu Phe Leu Tyr Glu Phe Gln Ala Asn Val Asn Pro Ile
        195                 200                 205

Gly Pro Tyr Val His His Asn Gln Ile Glu Gly Asn Gln Asp Phe
    210                 215                 220

Gly Phe Cys Ser Asn Phe Gln His Gly His Met Thr Thr Glu Ser Asp
225                 230                 235                 240

Ile Ser Asp Ser Ser Thr Ser Arg Met Ser Thr Ser Asn Ser Ser Asn
                245                 250                 255

Thr Met Ile Ser His Tyr Ser Ser Ala Gly Ile Gln Ile Asn Glu Met
            260                 265                 270

Leu Glu Trp Asp Ala Asp Asn Lys Ile Asp Ser Leu Ile Gln Tyr Pro
        275                 280                 285

Tyr Val Gly Ile Lys Asn Glu Glu Asn Phe Ser Asn Asn Asn Pro Leu
    290                 295                 300

Ser Gly Glu Asn Leu Asp Val Phe His His Ile
305                 310                 315

<210> SEQ ID NO 25

```
<211> LENGTH: 175
<212> TYPE: PRT
<213> ORGANISM: Vitis vinifera

<400> SEQUENCE: 25

Met Gly Arg His Ser Cys Cys Leu Lys Gln Lys Leu Arg Lys Gly Leu
1               5                   10                  15

Trp Ser Pro Glu Glu Asp Glu Lys Leu Tyr Asn Tyr Ile Thr Arg Phe
            20                  25                  30

Gly Val Gly Cys Trp Ser Ser Val Pro Lys Leu Ala Gly Leu Gln Arg
        35                  40                  45

Cys Gly Lys Ser Cys Arg Leu Arg Trp Ile Asn Tyr Leu Arg Pro Asp
    50                  55                  60

Leu Lys Arg Gly Met Phe Ser Gln Gln Glu Glu Asp Ile Ile Ile Ser
65                  70                  75                  80

Leu His Gln Val Leu Gly Asn Arg Trp Ala Gln Ile Ala Ala Gln Leu
                85                  90                  95

Pro Gly Arg Thr Asp Asn Glu Ile Lys Asn Phe Trp Asn Ser Cys Leu
            100                 105                 110

Lys Lys Lys Leu Leu Lys Gln Gly Met Asp Pro Asn Thr His Lys Pro
        115                 120                 125

Leu Asn Glu Thr Glu Val Gly Asp Gly Lys Asn Cys Thr Glu Lys Ala
    130                 135                 140

Ser Leu Gln Leu Gln His Phe His Cys Cys His Phe Pro Asp Phe
145                 150                 155                 160

Ser Tyr Ile Gln Thr Arg Lys Phe Tyr Pro Leu Leu Pro Phe Leu
                165                 170                 175

<210> SEQ ID NO 26
<211> LENGTH: 314
<212> TYPE: PRT
<213> ORGANISM: Sorghum bicolor

<400> SEQUENCE: 26

Met Gly Arg His Ala Ala Ser Gly Gly Gly Gly Val Gln Gln Lys
1               5                   10                  15

Leu Arg Lys Gly Leu Trp Ser Pro Glu Glu Asp Glu Lys Leu Tyr Asn
            20                  25                  30

His Ile Ile Arg Tyr Gly Val Gly Cys Trp Ser Ser Val Pro Lys Leu
        35                  40                  45

Ala Gly Leu Gln Arg Cys Gly Lys Ser Cys Arg Leu Arg Trp Ile Asn
    50                  55                  60

Tyr Leu Arg Pro Asp Leu Lys Arg Gly Ser Phe Ser Gln Gln Glu Glu
65                  70                  75                  80

Asp Ala Ile Val Gly Leu His Glu Ile Leu Gly Asn Arg Trp Ser Gln
                85                  90                  95

Ile Ala Ser His Leu Pro Gly Arg Thr Asp Asn Glu Ile Lys Asn Phe
            100                 105                 110

Trp Asn Ser Cys Leu Lys Lys Lys Leu Arg Gln Arg Gly Ile Asp Pro
        115                 120                 125

Ser Thr His Lys Pro Ile Ser Ala Asn Thr Ala Ala Ala Leu Glu
    130                 135                 140

Gln Pro Ala Ala Ser Gln Glu Arg Lys Pro Leu Ser Thr Ala Ala Ala
145                 150                 155                 160

Asp Gly Gly Phe Asp Thr Lys His Gln His Gln Val Phe Asp Pro
                165                 170                 175
```

```
Phe Pro Leu Thr Asp Ser Phe Gly Gly Gly Phe Asp Ala Ala Ala Gly
            180                 185                 190

Ala Ala Leu Tyr Gly His Met Gly Gly Gly Gly Lys Gln Asp Ala
        195                 200                 205

Gly Ala Phe Val Asp Tyr Ser Ser Val Leu Asp Val Ser Glu Asn Leu
    210                 215                 220

Gly Tyr Gly Glu Ser Ser Asn Ser Ser Asn Trp Asn Cys Ala Pro
225                 230                 235                 240

Glu Ala Asn Asn Ala Leu Asp Gly Asp Ala Pro Leu His Trp Ala
                245                 250                 255

Ser Glu Ser Lys Ala Thr Pro His Phe Ala Gly Tyr Gly Gly Gly Glu
        260                 265                 270

Glu Gln Ser Leu Glu Glu His Lys Phe Leu Leu Pro Cys His Gly Gln
        275                 280                 285

Gln Glu Gln Ser Leu Pro His Phe Asp Phe Asp Ile Ser Arg Gly Ala
    290                 295                 300

Val Val Gly Asp Phe Asn Leu Glu Phe Phe
305                 310

<210> SEQ ID NO 27
<211> LENGTH: 322
<212> TYPE: PRT
<213> ORGANISM: Sorghum bicolor

<400> SEQUENCE: 27

Met Gly Arg Leu Ser Cys Gly Gly Gly Val Gln Pro Lys Leu Arg
1               5                   10                  15

Lys Gly Leu Trp Ser Pro Glu Glu Asp Glu Lys Leu Tyr Asn His Ile
            20                  25                  30

Ile Arg His Gly Val Gly Cys Trp Ser Ser Val Pro Lys Leu Ala Gly
        35                  40                  45

Leu Gln Arg Cys Gly Lys Ser Cys Arg Leu Arg Trp Ile Asn Tyr Leu
    50                  55                  60

Arg Pro Asp Leu Lys Arg Gly Ser Phe Ser Gln Gln Glu Glu Asp Leu
65                  70                  75                  80

Ile Ile Ala Leu His Glu Ile Leu Gly Asn Arg Trp Ser Gln Ile Ala
                85                  90                  95

Ser His Leu Pro Gly Arg Thr Asp Asn Glu Ile Lys Asn Phe Trp Asn
            100                 105                 110

Ser Cys Leu Lys Lys Lys Leu Arg Gln Arg Gly Ile Asp Pro Ala Thr
        115                 120                 125

His Lys Pro Ile Ala Ala Gly Ala Ala Ala Glu Ala Gly Thr Ala Leu
    130                 135                 140

Pro Asp Gly Arg Asp His Asp Arg Lys Pro Gly Gly Ala Ala Asp Gly
145                 150                 155                 160

Asp Gly Asp Ala Asp Gly Leu Ala Gln Ser Lys Gln Leu Gln Pro Ala
                165                 170                 175

Ala Ala Val Phe Asp Pro Phe Pro Val Thr Asp Phe Gly Phe Asp Leu
            180                 185                 190

Gly Val Ala Ala Leu Tyr Cys Gly Pro Tyr Asp Asp Gly Lys Ala Ser
        195                 200                 205

Pro Asp Ala Gly Phe Val Ala Asp Tyr Ser Ser Val Leu Asp Val Ser
    210                 215                 220

Glu Asn Leu Gly Tyr Gly Glu Ser Ser Ser Asn Ser Ser Asn Trp Asn
```

```
                  225                 230                 235                 240

Cys Gly Ala Glu Met Ser Asn Ala Val Leu Asp Ser Glu Val Leu His
                245                 250                 255

Trp Ala Ser Gly Ala Ala Ala Lys Pro Glu Pro Tyr Thr Glu Leu
            260                 265                 270

Glu Gln Gln Gln His Ser Gly Tyr Ser Gly Gly Gly Gln
        275                 280                 285

Ala Val Asp Asp Asp Asp Ala Leu Glu His Lys Phe Leu Leu Pro
        290                 295                 300

Cys Gly Gly Gln Glu Gln Ser Leu Ala His Phe Asp Phe Asn Leu Glu
305                 310                 315                 320

Tyr Phe

<210> SEQ ID NO 28
<211> LENGTH: 341
<212> TYPE: PRT
<213> ORGANISM: Sorghum bicolor

<400> SEQUENCE: 28

Met Gly Arg Glu Ala Ala Ala Thr Arg Pro Lys Leu Arg Arg Gly Leu
1               5                   10                  15

Trp Ser Pro Glu Glu Asp Glu Lys Leu Tyr Asn His Ile Ile Arg Tyr
            20                  25                  30

Gly Val Gly Cys Trp Ser Ser Val Pro Lys Leu Ala Gly Leu Glu Arg
        35                  40                  45

Cys Gly Lys Ser Cys Arg Leu Arg Trp Ile Asn Tyr Leu Arg Pro Asp
    50                  55                  60

Leu Lys Arg Gly Ser Phe Ser Gln Gln Glu Glu Asp Leu Ile Ile Ser
65                  70                  75                  80

Leu His Lys Ile Leu Gly Asn Arg Trp Ser Gln Ile Ala Ser Gln Leu
                85                  90                  95

Pro Gly Arg Thr Asp Asn Glu Ile Lys Asn Phe Trp Asn Ser Cys Ile
            100                 105                 110

Lys Lys Lys Leu Arg Gln Arg Gly Ile Asp Pro Ala Thr His Lys Pro
        115                 120                 125

Leu Asn Asp Asp Asp Val Val Ala Ala Asp Asn Thr Val
    130                 135                 140

Ala Pro His Arg His Gln Asp Asp Lys Lys Leu Ala Ser Ser Thr Asp
145                 150                 155                 160

Asp Gln Cys Phe Ala Ala Met Gly Ala Ala Ala Ser Ser Asp Asp
                165                 170                 175

Pro Leu Ala Pro His Ser Pro Thr Val Ser Phe Asp Pro Leu Ser Val
            180                 185                 190

Thr Asn Val Pro Thr Met Gln Gln Gly Ser Tyr Gly Ala Ala His Ser
        195                 200                 205

Phe Gly Arg Ser Asp Asn His Leu Cys Asp Tyr Gly Val Asp Val
    210                 215                 220

Val Ser Asp Ala Ala Thr Thr Tyr Ser Ala Tyr Thr Gly Gly Gly Asp
225                 230                 235                 240

Ser Ser Ser Asn Ser Asn Gly Thr Trp Thr Cys Gly Gly Asn Asn Val
                245                 250                 255

Val Gly Gly Asp Pro Met Pro Pro His Met Asp Met Phe Gly Arg Asp
            260                 265                 270

Ala Glu Ala Val Tyr Gln Gln Phe Asp Pro Ala Lys Tyr Ser Pro Trp
```

```
              275                 280                 285
Gln His Gln Gln Gln His Pro Ala Ala Arg Phe Asp Gly His Asn
            290                 295                 300
Val Ser Ser Gly Gly Ala Ala Ala Gly Phe Leu Ile Arg Arg Asp Leu
305                 310                 315                 320
Pro Asp Ser Cys Phe Asp Leu Ala Arg Ser Ala Leu Glu Asp Glu Phe
                325                 330                 335
Ser Val Asp Phe Leu
                340

<210> SEQ ID NO 29
<211> LENGTH: 301
<212> TYPE: PRT
<213> ORGANISM: Sorghum bicolor

<400> SEQUENCE: 29

Met Gly Arg His Ala Ala Ser Gly Gly Gly Val Gln Gln Lys Leu Arg
1               5                   10                  15
Lys Gly Leu Trp Ser Pro Glu Glu Asp Glu Lys Leu Tyr Asn His Ile
                20                  25                  30
Ile Arg Tyr Gly Val Gly Cys Trp Ser Ser Val Pro Lys Leu Ala Gly
            35                  40                  45
Leu Gln Arg Cys Gly Lys Ser Cys Arg Leu Arg Trp Ile Asn Tyr Leu
        50                  55                  60
Arg Pro Asp Leu Lys Arg Gly Ser Phe Ser Gln Gln Glu Glu Asp Ala
65                  70                  75                  80
Ile Val Gly Leu His Gln Ile Leu Gly Asn Arg Trp Ser Gln Ile Ala
                85                  90                  95
Ser His Leu Pro Gly Arg Thr Asp Asn Glu Ile Lys Asn Phe Trp Asn
            100                 105                 110
Ser Cys Leu Lys Lys Lys Leu Arg Gln Arg Gly Ile Asp Thr Ser Thr
        115                 120                 125
His Lys Pro Ala Val Ser Ala Ser Val Pro Ala Ala Ser Glu Gln Pro
130                 135                 140
Val Ser Gln Asp Arg Lys Pro Leu Ala Ala Ala Ala Asp Gly Gly
145                 150                 155                 160
Ser Asp Met Lys His Gln Gln Val Phe Asp Pro Phe Pro Leu Thr Asp
                165                 170                 175
Ser Phe Gly Gly Gly Phe Gly Ala Ala Leu Tyr Gly His Thr Gly Gly
            180                 185                 190
Lys Gln Asp Ala Ala Ala Phe Val Asp Tyr Ser Ser Val Leu Asp Val
        195                 200                 205
Ser Glu Asn Leu Gly Tyr Gly Gly Ser Ser Asn Ser Ser Asn
210                 215                 220
Trp Asn Cys Ala Pro Glu Val His Asn Asn Ala Leu Asp Gly Asp Ala
225                 230                 235                 240
Pro Leu His Trp Ala Ser Glu Ser Lys Ala Thr Pro Phe Ala Gly Tyr
                245                 250                 255
Gly Gly Glu Glu Gln Ser Leu Leu Gly His Arg Phe Ser Val Pro Cys
            260                 265                 270
His Gly Gln Gln Glu Gln Ser Pro Pro Arg Phe Asp Phe Asp Ile Gly
        275                 280                 285
Arg Gly Ala Val Val Gly Glu Phe Ser Leu Glu Phe Phe
290                 295                 300
```

<210> SEQ ID NO 30
<211> LENGTH: 313
<212> TYPE: PRT
<213> ORGANISM: Sorghum bicolor

<400> SEQUENCE: 30

Met Gly Arg Leu Ser Cys Gly Gly Gly Gly Gly Val Gln Pro
1               5                   10                  15

Lys Leu Arg Lys Gly Leu Trp Ser Pro Glu Glu Asp Glu Lys Leu Tyr
            20                  25                  30

Asn His Ile Ile Arg His Gly Val Gly Cys Trp Ser Thr Val Pro Lys
        35                  40                  45

Leu Ala Gly Leu Gln Arg Cys Gly Lys Ser Cys Arg Leu Arg Trp Ile
    50                  55                  60

Asn Tyr Leu Arg Pro Asp Leu Lys Arg Gly Ser Phe Ser Gln Gln Glu
65                  70                  75                  80

Glu Asp Leu Ile Val Ala Leu His Glu Ile Leu Gly Asn Arg Trp Ser
                85                  90                  95

Gln Ile Ala Ser His Leu Pro Gly Arg Thr Asp Asn Glu Ile Lys Asn
            100                 105                 110

Phe Trp Asn Ser Cys Leu Lys Lys Lys Leu Arg Gln Arg Gly Ile Asp
        115                 120                 125

Pro Ala Thr His Lys Pro Val Ala Ala Glu Ala Ser Ala Ala Leu
    130                 135                 140

Pro Asp Ala Arg Asp His Asp Arg Glu Pro Gly Gly Ala Gly Ala Gly
145                 150                 155                 160

Ala Asp Ala Asp Gly Leu Ala Gln Gln Ser Lys Gln Pro Ala Ala Ala
                165                 170                 175

Val Phe Asp Pro Phe Pro Val Val Asp Phe Gly Phe Asp Leu Ser Gly
            180                 185                 190

Gly Gly Gly Val Ala Ala Leu Tyr Gly Gly Pro Tyr Asp Ala Ala Ala
        195                 200                 205

Gly Lys Ala Ser Ala Asp Asp Gly Gly Phe Val Ala Asp Tyr Ser Ser
    210                 215                 220

Val Leu Asp Val Ser Glu Asn Leu Gly Tyr Gly Glu Ser Ser Ser Asn
225                 230                 235                 240

Ser Ser Asn Trp Gly Asn Gly Ala Glu Met Gly Asn Ala Ala Ala Ala
                245                 250                 255

Val Leu Asp Gly Glu Val Leu His Trp Ala Lys Pro Glu Pro Tyr Thr
            260                 265                 270

Glu Leu Glu Gln Arg Ser Ala Gly Gln Ala Ala Ala Asp Asp Asp Ala
        275                 280                 285

Leu His His Arg Phe Leu Leu Pro Cys Gly Gln Glu Gln Ser Leu Ala
    290                 295                 300

His Leu Asp Phe Gly Leu Glu Tyr Phe
305                 310

<210> SEQ ID NO 31
<211> LENGTH: 362
<212> TYPE: PRT
<213> ORGANISM: Sorghum bicolor

<400> SEQUENCE: 31

Met Gly Arg Glu Ala Ala Ala Thr Arg Pro Pro Lys Leu Arg Arg Gly
1               5                   10                  15

Leu Trp Ser Pro Glu Asp Glu Lys Leu Tyr Asn His Ile Ile Arg
              20                  25                  30

Tyr Gly Val Gly Cys Trp Ser Val Pro Lys Leu Ala Gly Leu Glu
          35                  40                  45

Arg Cys Gly Lys Ser Cys Arg Leu Arg Trp Ile Asn Tyr Leu Arg Pro
     50                  55                  60

Asp Leu Lys Arg Gly Ser Phe Ser Gln Gln Glu Asp Leu Ile Val
65                   70                  75                  80

Ser Leu His Lys Ile Leu Gly Asn Arg Trp Ser Gln Ile Ala Ser Gln
                 85                  90                  95

Leu Pro Gly Arg Thr Asp Asn Glu Ile Lys Asn Phe Trp Asn Ser Cys
             100                 105                 110

Ile Lys Lys Lys Leu Arg Gln Gln Gly Ile Asp Pro Ala Thr His Lys
         115                 120                 125

Pro Leu Asn Asp Asp Asn Ala Ala Ala Ala Ala Ala Ala Asp Asn
        130                 135                 140

Asp Ala Ala Val Ala Pro His His His Arg Arg His Gln Asp Asp His
145                 150                 155                 160

Cys Gly Ala Ala Asn Ile Asp Asn Asn Asn Asn Asn Asn Asn Asn
                165                 170                 175

Asn Asn Arg Gln Leu Pro Ser Ala Asp Asp His Cys Phe Ala Met Ser
            180                 185                 190

Ser Asp Pro Leu Ala Pro His Ser Pro Thr Val Ser Phe Asp Pro
        195                 200                 205

Leu Ser Val Thr Asn Val Pro Thr Ala Met Gln Gln Gly Ser Tyr Gly
    210                 215                 220

Ser Phe Arg Ser Asp Asn Asp His Leu Cys Asp Tyr Gly Gly Gly
225                 230                 235                 240

Val Asp Val Ser Asp Ala Ala Thr Ala Tyr Ser Ala Pro Tyr Thr
                245                 250                 255

Gly Gly Gly Gly Gly Gly Asp Ser Ser Ser Asn Ser Asn Gly Asn
            260                 265                 270

Gly Thr Trp Ala Cys Ser Gly Gly Glu Pro Met Pro Pro His Val Ala
        275                 280                 285

Met Phe Gly Arg Asp Ala Ala Gln Ala Ala Ala Tyr His Gln Phe Val
    290                 295                 300

Asp Pro Ala Lys Tyr Ser Pro Trp Gln Gln His Pro Ala Ala Arg Leu
305                 310                 315                 320

His Asp His Asn Val Gly Gly Ala Ala Ala Gly Phe Pro Ile Arg Ser
                325                 330                 335

Met Ser Arg Asp Leu Pro Gly Ser Cys Phe Asp Leu Ala Arg Ser Ala
            340                 345                 350

Leu Glu Asp Glu Phe Ser Val Asp Phe Leu
        355                 360

<210> SEQ ID NO 32
<211> LENGTH: 48
<212> TYPE: DNA
<213> ORGANISM: Artificial Sequence
<220> FEATURE:
<223> OTHER INFORMATION: A synthetic oligonucleotide

<400> SEQUENCE: 32
acaagtttgt acaaaaaagc aggctctatg gggcggcacg cgggcact                    48

<210> SEQ ID NO 33
<211> LENGTH: 48
<212> TYPE: DNA
<213> ORGANISM: Artificial Sequence
<220> FEATURE:
<223> OTHER INFORMATION: A synthetic oligonucleotide

<400> SEQUENCE: 33
accactttgt acaagaaagc tgggtatcaa aagtactcga ggttgaag           48

<210> SEQ ID NO 34
<211> LENGTH: 44
<212> TYPE: DNA
<213> ORGANISM: Artificial Sequence
<220> FEATURE:
<223> OTHER INFORMATION: A synthetic oligonucleotide

<400> SEQUENCE: 34
acaacttttg tatacaaagt tgtaaagtac tcgaggttga agtc               44

<210> SEQ ID NO 35
<211> LENGTH: 58
<212> TYPE: DNA
<213> ORGANISM: Artificial Sequence
<220> FEATURE:
<223> OTHER INFORMATION: A synthetic oligonucleotide

<400> SEQUENCE: 35
ggggacaact ttgtatacaa aagttgctgt tgatcttgat cttgaattga gattgggt    58

<210> SEQ ID NO 36
<211> LENGTH: 48
<212> TYPE: DNA
<213> ORGANISM: Artificial Sequence
<220> FEATURE:
<223> OTHER INFORMATION: A synthetic oligonucleotide

<400> SEQUENCE: 36
ggggaccact tgtacaaga aagctgggta tcaagcaaaa cccaatct            48

<210> SEQ ID NO 37
<211> LENGTH: 49
<212> TYPE: DNA
<213> ORGANISM: Artificial Sequence
<220> FEATURE:
<223> OTHER INFORMATION: A synthetic oligonucleotide

<400> SEQUENCE: 37
ggggacaact ttgtatacaa aagttgctat ggtgagcaag ggcgaggag          49

<210> SEQ ID NO 38
<211> LENGTH: 54
<212> TYPE: DNA
<213> ORGANISM: Artificial Sequence
<220> FEATURE:
<223> OTHER INFORMATION: A synthetic oligonucleotide

<400> SEQUENCE: 38
ggggaccact ttgtacaaga aagctgggta tcacttgtac agctcgtcca tgcc    54

<210> SEQ ID NO 39
<211> LENGTH: 50
<212> TYPE: DNA
<213> ORGANISM: Artificial Sequence
<220> FEATURE:
<223> OTHER INFORMATION: A synthetic oligonucleotide

<400> SEQUENCE: 39
ggggacaagt tgtacaaaa aagcaggctc tatggtgagc aagggcgagg    50

<210> SEQ ID NO 40
<211> LENGTH: 23
<212> TYPE: DNA
<213> ORGANISM: Artificial Sequence
<220> FEATURE:
<223> OTHER INFORMATION: A synthetic oligonucleotide

<400> SEQUENCE: 40
aatatagcgc gctgcatgtc ctc    23

<210> SEQ ID NO 41
<211> LENGTH: 23
<212> TYPE: DNA
<213> ORGANISM: Artificial Sequence
<220> FEATURE:
<223> OTHER INFORMATION: A synthetic oligonucleotide

<400> SEQUENCE: 41
aatatagcgc gctgcatgtc ctc    23

<210> SEQ ID NO 42
<211> LENGTH: 23
<212> TYPE: DNA
<213> ORGANISM: Artificial Sequence
<220> FEATURE:
<223> OTHER INFORMATION: A synthetic oligonucleotide

<400> SEQUENCE: 42
aggaaacagg tggtcgcaga ttg    23

<210> SEQ ID NO 43
<211> LENGTH: 24
<212> TYPE: DNA
<213> ORGANISM: Artificial Sequence
<220> FEATURE:
<223> OTHER INFORMATION: A synthetic oligonucleotide

<400> SEQUENCE: 43
gcttcttctt gaggcagctg ttcc    24

<210> SEQ ID NO 44
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 44
ggaggcacct caggtcattt    20

<210> SEQ ID NO 45
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 45
atagcggtca ttgtcttgcg    20

<210> SEQ ID NO 46
<211> LENGTH: 20

```
<212> TYPE: DNA
<213> ORGANISM: Artificial Sequence
<220> FEATURE:
<223> OTHER INFORMATION: A synthetic oligonucleotide

<400> SEQUENCE: 46
ttgctctcca gagcgatgac                                                    20

<210> SEQ ID NO 47
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 47
ctccacgaca taatcggcac                                                    20

<210> SEQ ID NO 48
<211> LENGTH: 22
<212> TYPE: DNA
<213> ORGANISM: Artificial Sequence
<220> FEATURE:
<223> OTHER INFORMATION: A synthetic oligonucleotide

<400> SEQUENCE: 48
aggatagaat gggcagcatc gc                                                 22

<210> SEQ ID NO 49
<211> LENGTH: 24
<212> TYPE: DNA
<213> ORGANISM: Artificial Sequence
<220> FEATURE:
<223> OTHER INFORMATION: A synthetic oligonucleotide

<400> SEQUENCE: 49
atcttcaggg cctgtcttcc tgag                                               24

<210> SEQ ID NO 50
<211> LENGTH: 23
<212> TYPE: DNA
<213> ORGANISM: Artificial Sequence
<220> FEATURE:
<223> OTHER INFORMATION: A synthetic oligonucleotide

<400> SEQUENCE: 50
tggagagctg gtactacctg aag                                                23

<210> SEQ ID NO 51
<211> LENGTH: 22
<212> TYPE: DNA
<213> ORGANISM: Artificial Sequence
<220> FEATURE:
<223> OTHER INFORMATION: A synthetic oligonucleotide

<400> SEQUENCE: 51
cgacatcccg tatgccttgt tg                                                 22

<210> SEQ ID NO 52
<211> LENGTH: 22
<212> TYPE: DNA
<213> ORGANISM: Artificial Sequence
<220> FEATURE:
<223> OTHER INFORMATION: A synthetic oligonucleotide

<400> SEQUENCE: 52
```

-continued gcgtttcgca tacaccaaca cc                                         22

<210> SEQ ID NO 53
<211> LENGTH: 23
<212> TYPE: DNA
<213> ORGANISM: Artificial Sequence
<220> FEATURE:
<223> OTHER INFORMATION: A synthetic oligonucleotide

<400> SEQUENCE: 53
actcgctagg ttgttcagtg tgg                                        23

<210> SEQ ID NO 54
<211> LENGTH: 22
<212> TYPE: DNA
<213> ORGANISM: Artificial Sequence
<220> FEATURE:
<223> OTHER INFORMATION: A synthetic oligonucleotide

<400> SEQUENCE: 54
gcgattcgcc tacatcaaca cc                                         22

<210> SEQ ID NO 55
<211> LENGTH: 22
<212> TYPE: DNA
<213> ORGANISM: Artificial Sequence
<220> FEATURE:
<223> OTHER INFORMATION: A synthetic oligonucleotide

<400> SEQUENCE: 55
ggctggcaaa tgtgctaatc gg                                         22

<210> SEQ ID NO 56
<211> LENGTH: 22
<212> TYPE: DNA
<213> ORGANISM: Artificial Sequence
<220> FEATURE:
<223> OTHER INFORMATION: A synthetic oligonucleotide

<400> SEQUENCE: 56
caaagcacaa gttccgcctg tg                                         22

<210> SEQ ID NO 57
<211> LENGTH: 24
<212> TYPE: DNA
<213> ORGANISM: Artificial Sequence
<220> FEATURE:
<223> OTHER INFORMATION: A synthetic oligonucleotide

<400> SEQUENCE: 57
tggctcgtat gcatctgtca aatc                                       24

<210> SEQ ID NO 58
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 58
aaggcttgaa catgacagca                                            20

<210> SEQ ID NO 59
<211> LENGTH: 20
<212> TYPE: DNA
<213> ORGANISM: Artificial Sequence

```
<220> FEATURE:
<223> OTHER INFORMATION: A synthetic oligonucleotide

<400> SEQUENCE: 59
atgaaatggg cacctgaaaa                                                        20

<210> SEQ ID NO 60
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 60
tgcaaaaggc ctcagctaat                                                        20

<210> SEQ ID NO 61
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 61
tggtggcata caaaacctca                                                        20

<210> SEQ ID NO 62
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 62
cttcacgctc actcaccatc                                                        20

<210> SEQ ID NO 63
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 63
cggaagacca agaatgaagc                                                        20

<210> SEQ ID NO 64
<211> LENGTH: 19
<212> TYPE: DNA
<213> ORGANISM: Artificial Sequence
<220> FEATURE:
<223> OTHER INFORMATION: A synthetic oligonucleotide

<400> SEQUENCE: 64
cttgctctca ccgtcctga                                                         19

<210> SEQ ID NO 65
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 65
ggtttcgaag cgaaggtgac                                                        20
```

<210> SEQ ID NO 66
<211> LENGTH: 23
<212> TYPE: DNA
<213> ORGANISM: Artificial Sequence
<220> FEATURE:
<223> OTHER INFORMATION: A synthetic oligonucleotide

<400> SEQUENCE: 66
ttcctattgc aagtacatca tgc                                              23

<210> SEQ ID NO 67
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 67
tatcgtgtgc tgcccatcta                                                  20

<210> SEQ ID NO 68
<211> LENGTH: 24
<212> TYPE: DNA
<213> ORGANISM: Artificial Sequence
<220> FEATURE:
<223> OTHER INFORMATION: A synthetic oligonucleotide

<400> SEQUENCE: 68
aaactgtttg aaaatcaaat ctgc                                             24

<210> SEQ ID NO 69
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 69
ggaagttgtc gtgggatcag                                                  20

<210> SEQ ID NO 70
<211> LENGTH: 22
<212> TYPE: DNA
<213> ORGANISM: Artificial Sequence
<220> FEATURE:
<223> OTHER INFORMATION: A synthetic oligonucleotide

<400> SEQUENCE: 70
tcgagaaata atggttcaga cg                                               22

<210> SEQ ID NO 71
<211> LENGTH: 22
<212> TYPE: DNA
<213> ORGANISM: Artificial Sequence
<220> FEATURE:
<223> OTHER INFORMATION: A synthetic oligonucleotide

<400> SEQUENCE: 71
agatatactt gttgtcgcga ag                                               22

<210> SEQ ID NO 72
<211> LENGTH: 24
<212> TYPE: DNA
<213> ORGANISM: Artificial Sequence
<220> FEATURE:
<223> OTHER INFORMATION: A synthetic oligonucleotide

```
<400> SEQUENCE: 72
agaatctcgt gctttcagct tcga                                          24

<210> SEQ ID NO 73
<211> LENGTH: 24
<212> TYPE: DNA
<213> ORGANISM: Artificial Sequence
<220> FEATURE:
<223> OTHER INFORMATION: A synthetic oligonucleotide

<400> SEQUENCE: 73
tcaagaccaa tgcggagcat atac                                          24

<210> SEQ ID NO 74
<211> LENGTH: 24
<212> TYPE: DNA
<213> ORGANISM: Artificial Sequence
<220> FEATURE:
<223> OTHER INFORMATION: A synthetic oligonucleotide

<400> SEQUENCE: 74
gcatggcgca ttttgacttc aacc                                          24

<210> SEQ ID NO 75
<211> LENGTH: 26
<212> TYPE: DNA
<213> ORGANISM: Artificial Sequence
<220> FEATURE:
<223> OTHER INFORMATION: A synthetic oligonucleotide

<400> SEQUENCE: 75
ctacacaatg ttcacattcc tatacc                                        26
```

PLANT BIOMASS YIELD INCREASE BY MODIFIED SWAM1 GENE EXPRESSION

CLAIM OF PRIORITY

This application claims the benefit of priority of U.S. Provisional Patent Application No. 62/186,801, filed 30 Jun. 2015, the benefit of priority of which is claimed hereby, and which is incorporated by reference herein in its entirety.

GOVERNMENT GRANT SUPPORT

This invention was made with government support under DE-FG02-08ER64700DE and DE-SC0006641 awarded by the Office of Science, Biological and Environmental Research, Department of Energy. The government has certain rights in the invention.

SEQUENCE LISTING

This document incorporates by reference herein an electronic sequence listing text file, which is filed in electronic format via EFS-Web. The text file is named "1593751.txt," is 86,016 bytes, and was created on Jun. 28, 2016.

BACKGROUND

Plant biomass offers a sustainable low cost alternative to fossil fuels and grasses such as miscanthus, sorghum and switchgrass can provide biofuel feedstocks.

SUMMARY OF THE INVENTION

One embodiment provides a transgenic plant, including, but not limited to, transgenic miscanthus, switchgrass, sorghum, poplar, wheat, lye, corn, barley, oat, rapeseed, potatoes, rice, soybean, *Brachypoclium distachyon* plant, plant cell, plant part or seed, wherein the transgenic plant, plant cell, plant part or seed comprises a heterologous promoter which increases expression of SWAM1, other genes related to SWAM1 (see FIG. 7), or GNRF, as compared to a non-transgenic plant.

Another embodiment provides a method to increase plant biomass, with respect to a control plant, the method comprising transforming a plant, including, but not limited to, miscanthus, switchgrass, sorghum, poplar, wheat, rye, corn, barley, oat, rapeseed, potatoes, rice, soybean, *Brachypodium distachyon* plant with a recombinant polynucleotide that encodes a heterologous promoter that increases the expression of SWAM1, other genes related to SWAM1 (see FIG. 7), or GNRF, wherein increased expression of SWAM1, other genes related to SWAM1 (see FIG. 7), or GNRF in the transgenic plant, results in a transgenic plant with increased biomass.

Another embodiment provides a method to produce a transgenic plant with increased biomass comprising introducing a nucleic acid encoding a SWAM1 transcription factor, other genes related to SWAM1 (see FIG. 7), or GNRF under the control of a heterologous promoter into a plant cell including, but not limited to, transgenic miscanthus, switchgrass, sorghum, poplar, wheat, rye, corn, barley, oat, rapeseed, potatoes, rice, soybean, *Brachypodium distachyon* plant cell.

BRIEF DESCRIPTION OF THE DRAWINGS

FIGS. 5A-F. SWAM1 is an activator of interfascicular fibers secondary cell wall thickening. Representative transmission electron micrographs illustrating the cell wall thickness of cells in the interfascicular fiber region of the first internode of inflorescence stems of control (A,D), SWAM1-OE (B,E) and SWAM1-DR (C,F). D-F are 5× magnified images of A-C. Black and white lines indicate the thickness of secondary and primary walls, respectively. Scale bars=5 μm (A-C) and 1 μm (D-F).

FIGS. 6A-D. SWAM1 directly interacts with an AC-like sequence motif to activate cell wall gene expression. Relative expression of SWAM1 (A) and secondary cell wall genes (B) in control, SWAM1-OE and SWAM1-DR stems.

The tallest stem was collected from developmentally equivalent plants when the inflorescence was first visible from the flag leaf Nine individuals from three independent events were analyzed in triplicate using QRT-PCR and normalized relative to two housekeeping genes, BdUBC18 and BdGct-pDH, β-galactosidase activity illustrating a preferential interaction between the AC-II element and SWAM1 protein in yeast (C). Values are mean of three independent yeast transformations. Relative fold enrichment of cell wall promoter fragments (D). Three biological samples were analyzed for control and SWAM1:GFP in triplicate using QRT-PCR and normalized to input DNA. *$p<0.05$.

Figure 7A:
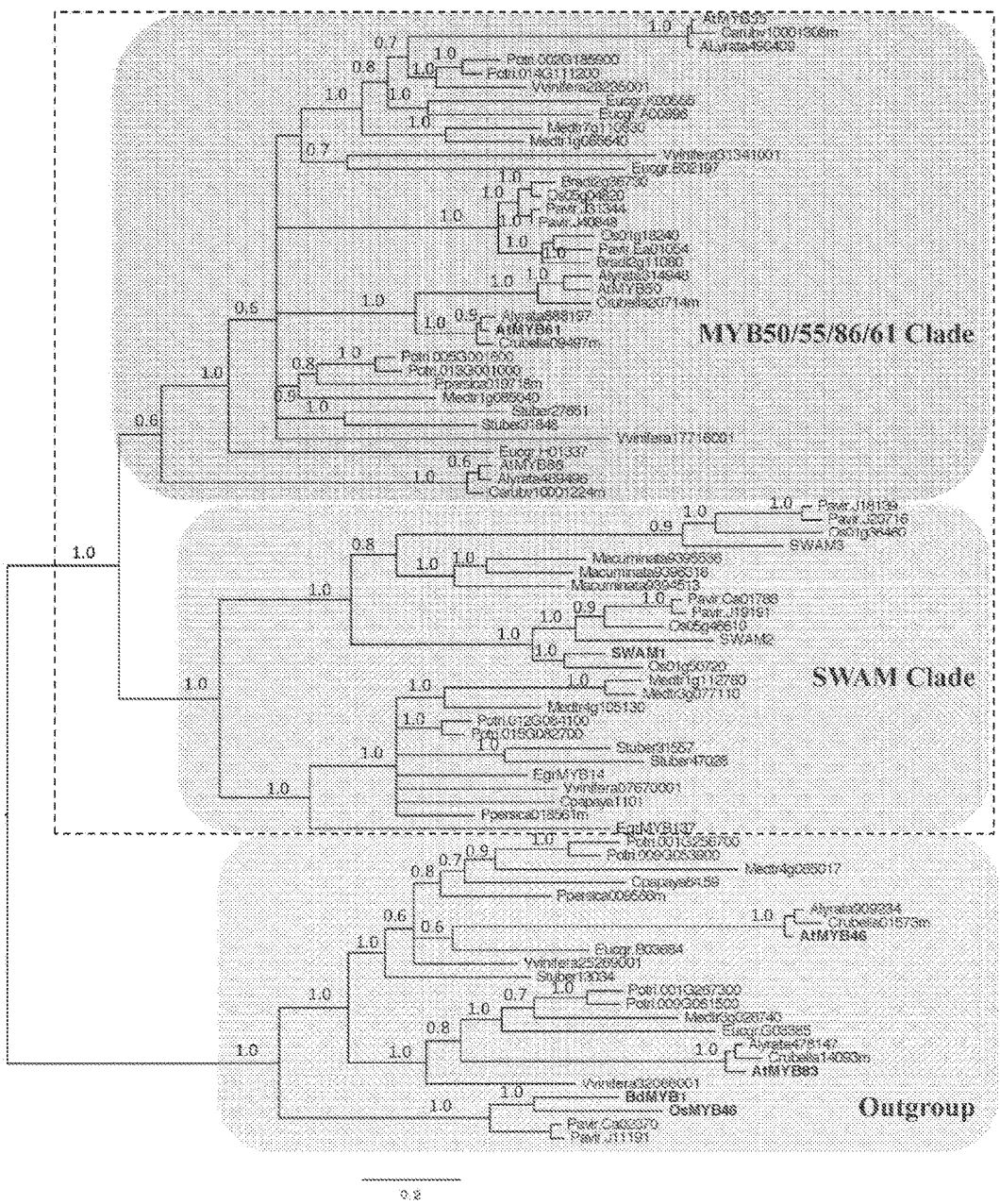

FIG. 7A. Group of genes related to SWAM1 are depicted.

FIGS. 7B-L. Provides the gene names and the predicted protein sequences of those genes listed in 7A (SEQ ID NOs: 2-31).

Figure 8:
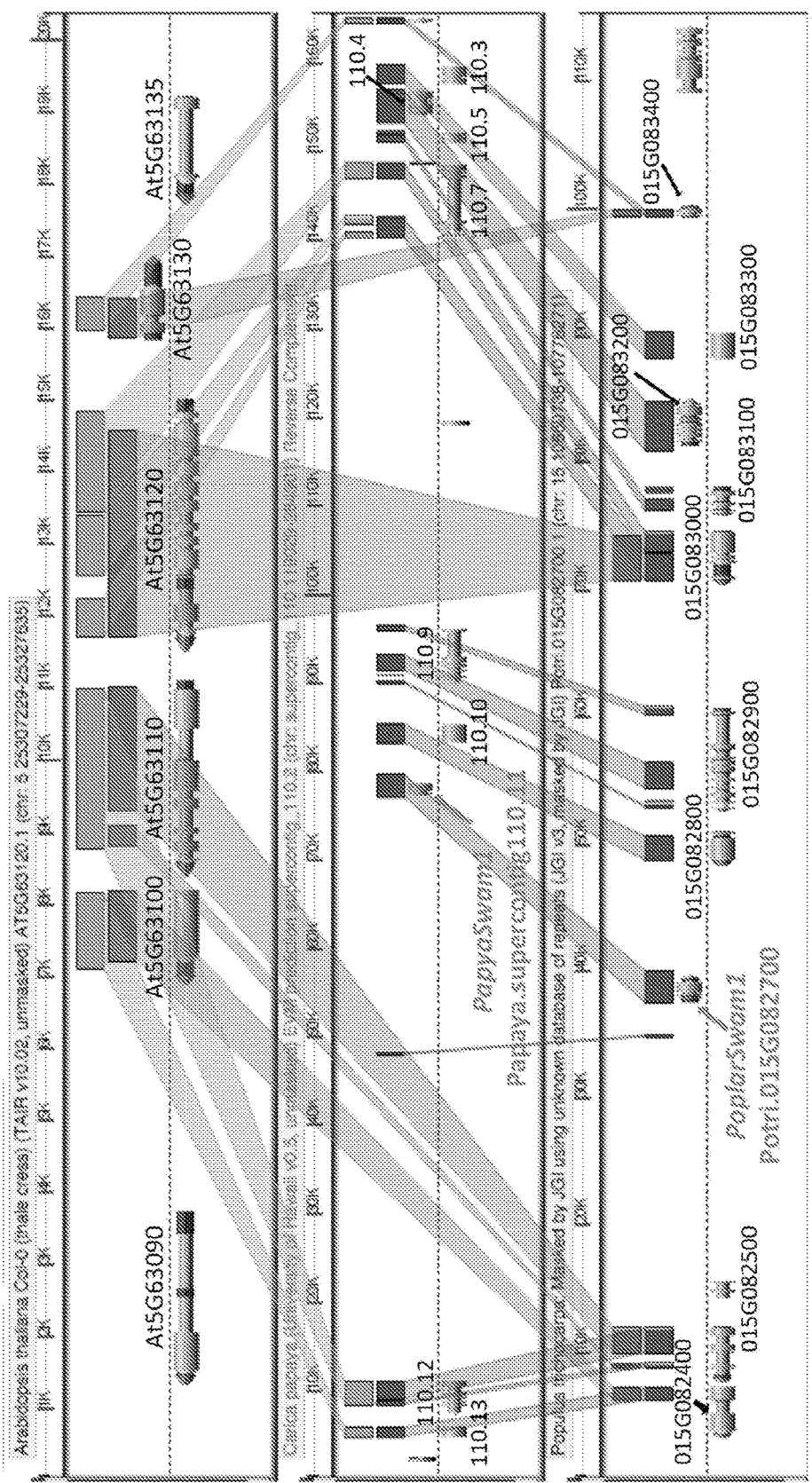

FIG. 8. Synteny analysis of the SWAM1 regions of papaya (Papaya.sugercontig110) and poplar (Potri Chr 15) suggests loss of this and two adjacent loci in *Arabidopsis thaliana*. Syntenically conserved papaya and poplar loci in the region are marked, with the prefixes Papaya.supercontig and Potri. omitted for clarity. The figure was generated with SynFind, which is incorporated into CoGe (genomevolution.org/CoGe/).

Figure 9:
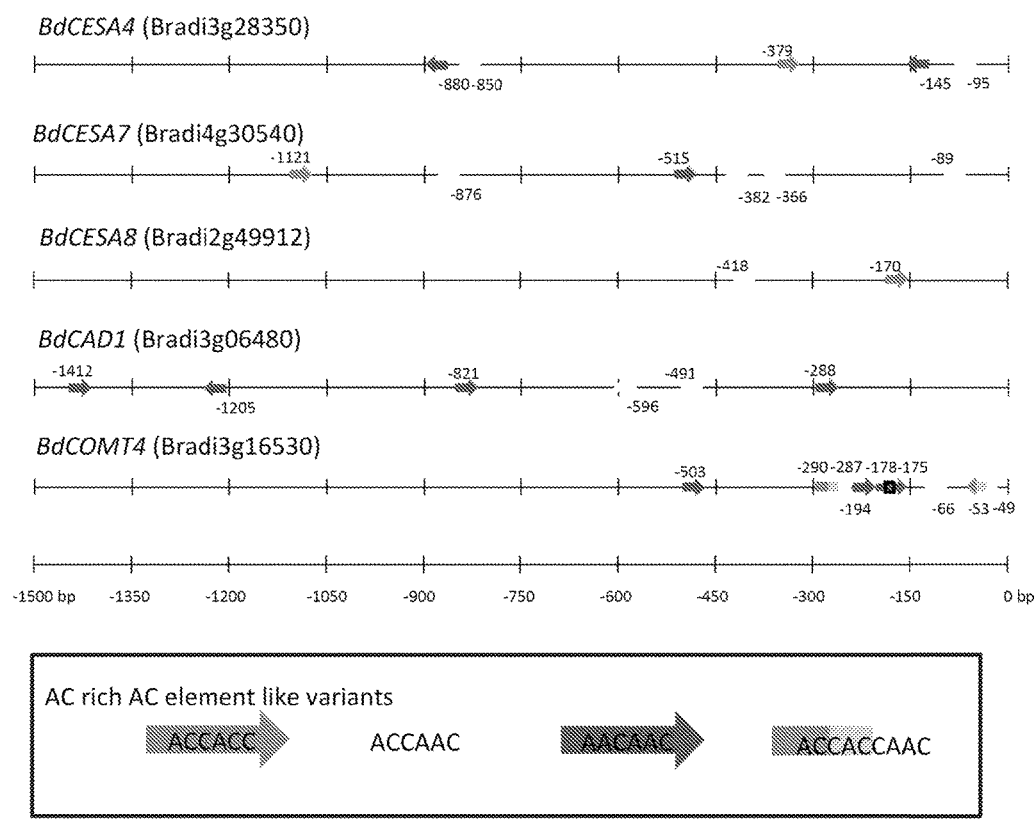

FIG. 9. Variants of the AC element are present in *Brachypodium distachyon* cellulose and lignin gene promoters. 1500 bp upstream of the transcription start site was analyzed for the presence of the AC-like elements.

Figure 10:
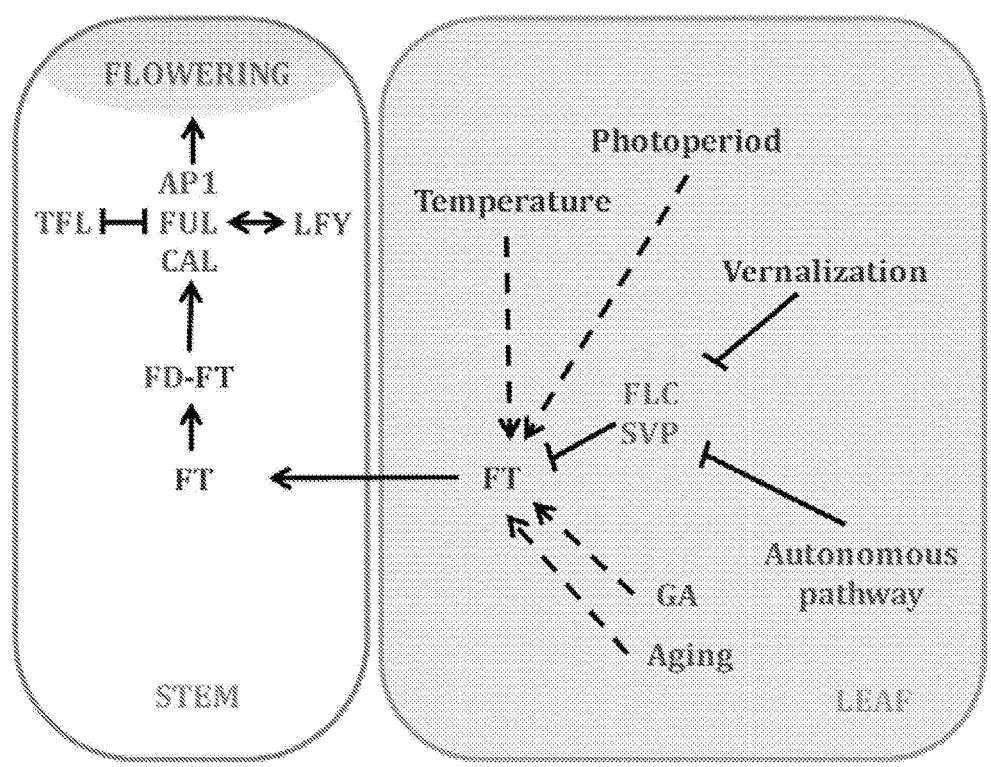

FIG. 10. A simplified model for flowering in *Arabidopsis thaliana*. FLOWERING LOCUS T(FT) is activated by temperature, photoperiod, clock, hormones and aging. FLOWERING LOCUS C (FLC) and SHORT VEGETATIVE PHASE (SVP) are the main repressors of FT. FLC is activated by FRIGID A (FRI) and is repressed by the autonomous pathway and cold. When the timing is suitable for flowering FT protein moves through the phloem to the stem and interacts with the FD. FT-FD complex is responsible for activating the floral integrator gene SUPPRESSOR OF OVEREXPRESSION OF CONSIANSI (SOC1) and the floral meristem identity genes APETALA 1 (AP1), CAULIFLOWER (CAL), FRUITFUL (FUL) and LEAFY (LFY) which results in the vegetat8ive reproductive transition.

Figure 11:
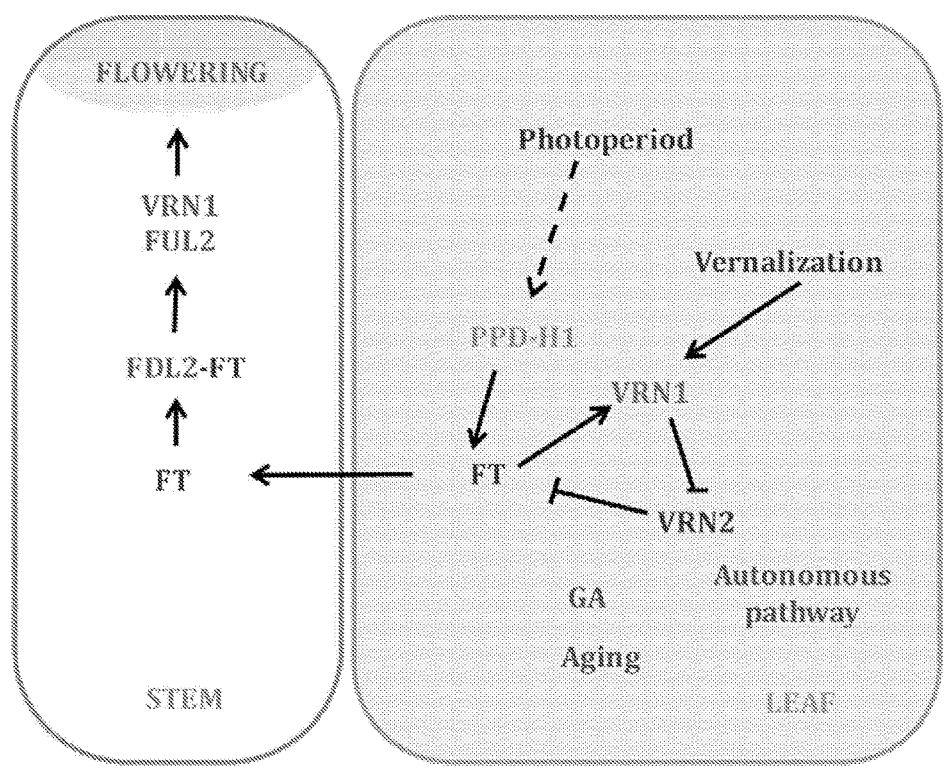

FIG. 11. Proposed model for flowering in grasses. FLOWERING LOCUS T (FT) is activated by long days via PHOTOPERIOD1-H1 (PPD-H1) and is replaced by VERNALIZATION 2 (VRN2). During winter VRN1 is activated and represses VRN2 to initiate flowering in spring. Once activated FT moves through the phloem into the stem where it complexes with FLOWERING LOCUS D LIKE2 (FLDL2) to activate the floral meristem identity gene VRN1.

Figure 12A:
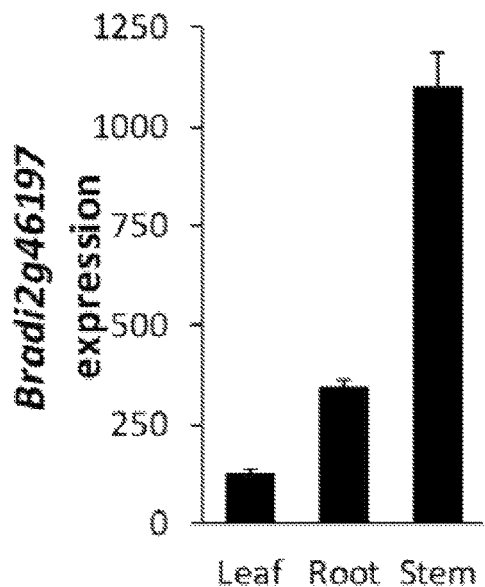
Figure 12B:
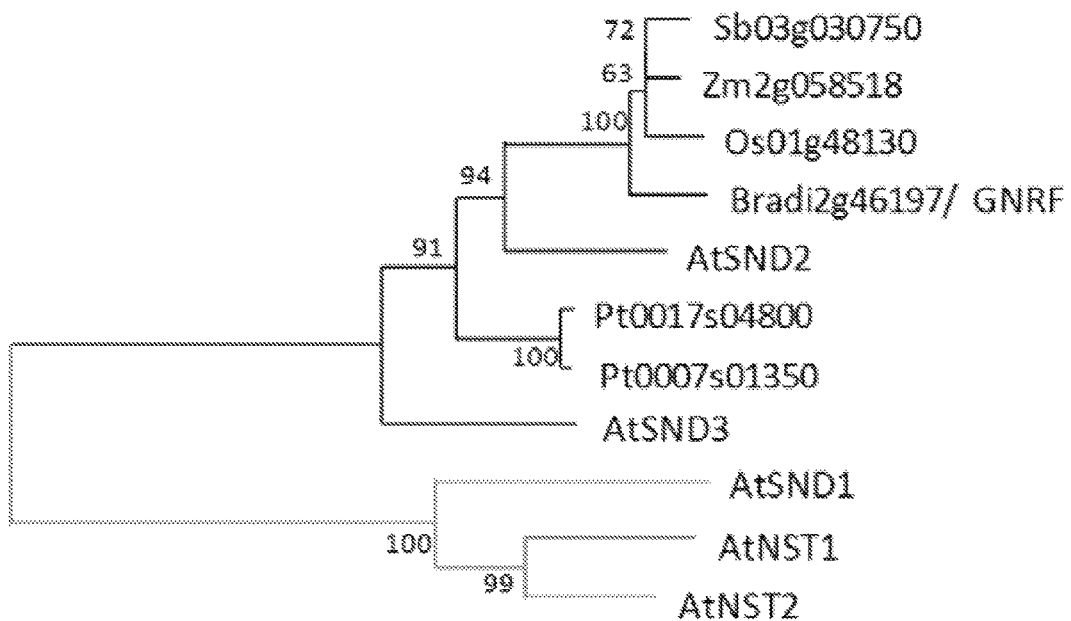

FIGS. 12A-B. Relative expression and phylogeny of Bradi2g4617. (A) Relative transcript abundance of Bradi2g4617 in leaf, root and stem tissue measured with a microarray. Mean±standard deviation of three biological replicates. (B) A subclade fo the NAC phylogeny illustrating amino acid sequence similarity between *Arabidopsis thaliana*, *Brachypodium distachyon*, *Oryza sativa*, *Zea maize*, *Populus trichocarpa* and *Sorghum biocolor*. A rooted neighbor-joining phylogeny was constructed using MEGA5 with 1000 bootstrap permutations. Numbers on each branch indicate bootstrap support. Branches indicate in blue were used as an out group.

Figure 13:
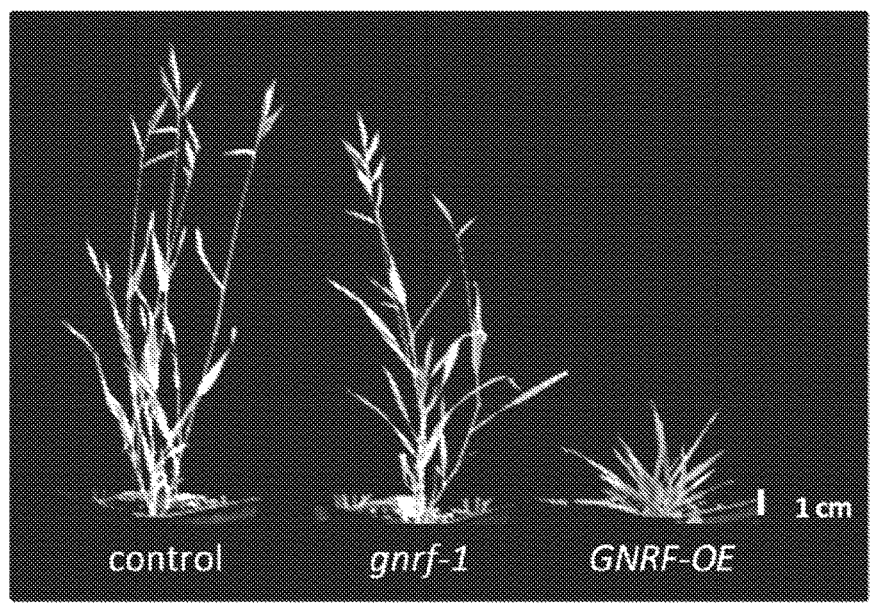

FIG. 13. Plant phenotypes of control (left), gnrf-1 (center) and GNRF-OE (right) at flowering stage images were captured at the time of control plant flowering. Scale bar=1 cm.

Figure 14A:
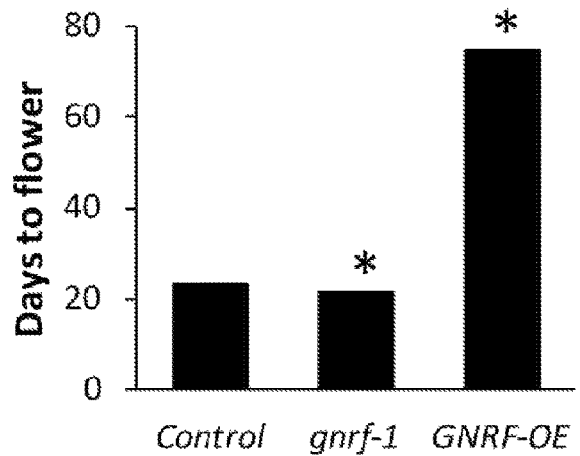
Figure 14B:
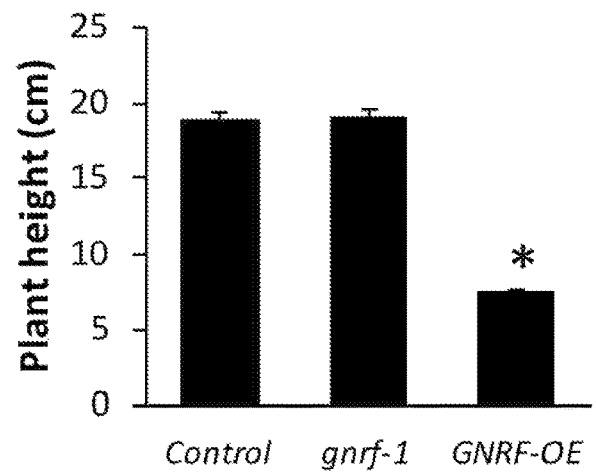
Figure 14C:
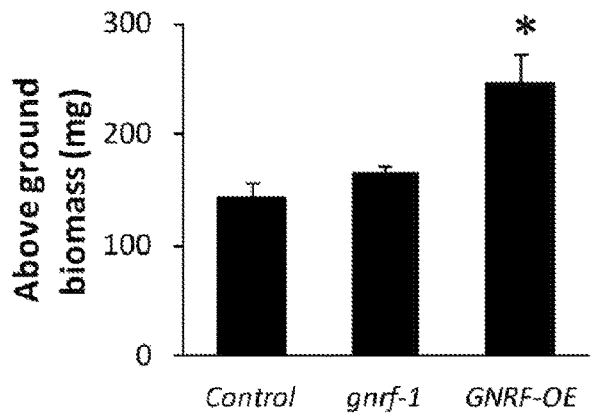

FIGS. 14A-C. Whole plant phenotypes. (A) Days taken for the first flower to be visible from the flag leaf Fifteen to forty eight individuals were analyzed for each line. Note that GNRF-OE remained vegetative even after 75 days, (B) Plant height at complete maturity, (C) Total above ground biomass at complete senescence. Fifteen to twenty one individuals were analyzed for each line. *$p<0.05$.

Figure 15:
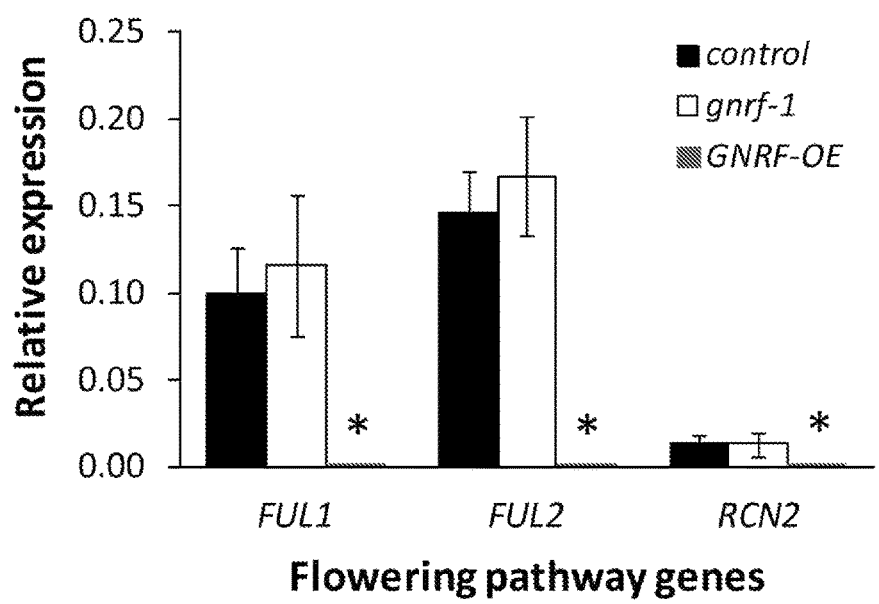

FIG. 15. Transcript abundance of flowering pathway genes in stems. Relative expression of FUL1, FUL2, and RCN2 gene in control, gnrf-1 and GNRF-OE stems. Tallest stem was collected from developmentally equivalent plants when the inflorescence was first visible from the flag leaf. Eight to ten individuals from each line were analyzed in triplicate using QRT-PCR and normalized against two housekeeping genes. *$p<0.05$.

FIGS. 16A-D. Relative expression of flowering pathway genes in leaves (A) FT, (B) MADS37, (C) ODDSOC1, and (D) ODDSOC2 Fourth leaf from the base of the tallest stem was collected from developmentally equivalent plants when the inflorescence was first visible from the flag leaf. Seven to nine individuals were analyzed in triplicate using QRT-PCR and normalized against two housekeeping genes. *$p<0.05$.

Figure 17:
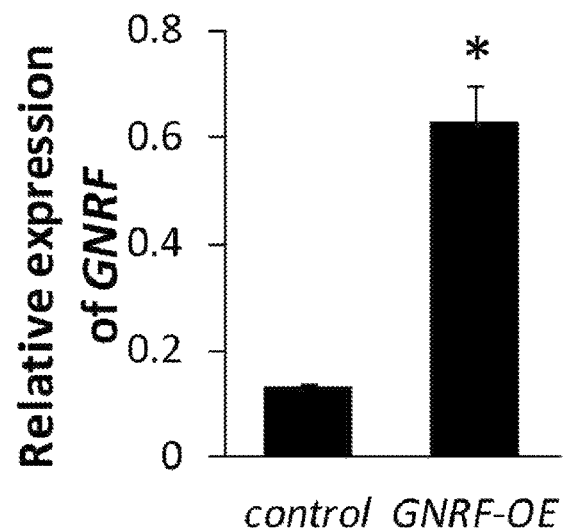

FIG. 17. Transcript abundance of GNRF in control and GNRF-OE stems. Relative expression of GNRF was measured in the stem tissue of the tallest stem when the inflorescence was just visible from the flag leaf of the control plants. Ten individuals were analyzed in triplicate using QRT-PCR and normalized against two housekeeping genes. *$p<0.05$.

Figure 18:
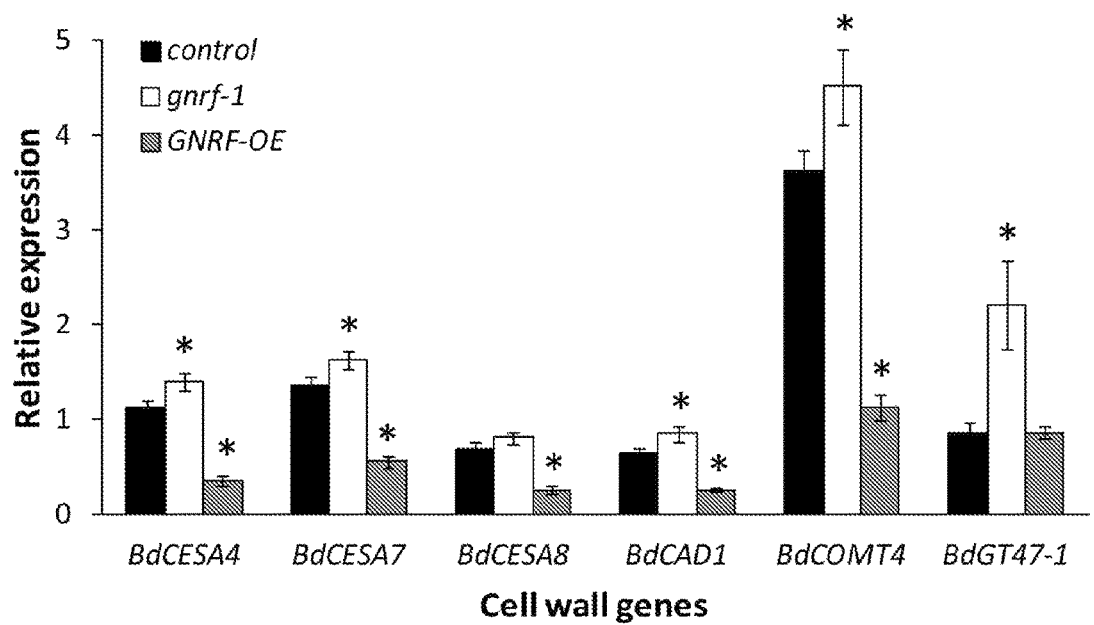

FIG. 18. Target cell wall gene expression in stems. Relative expression of secondary cell wall genes in control, gnrf-1 and GNRF-OE stems. Tallest stem was collected from developmentally equivalent plants when the inflorescence was first visible form the flag leaf. Eight to ten individuals were analyzed in triplicate using QRT-PCR and normalized against two housekeeping genes.

Figure 19A:
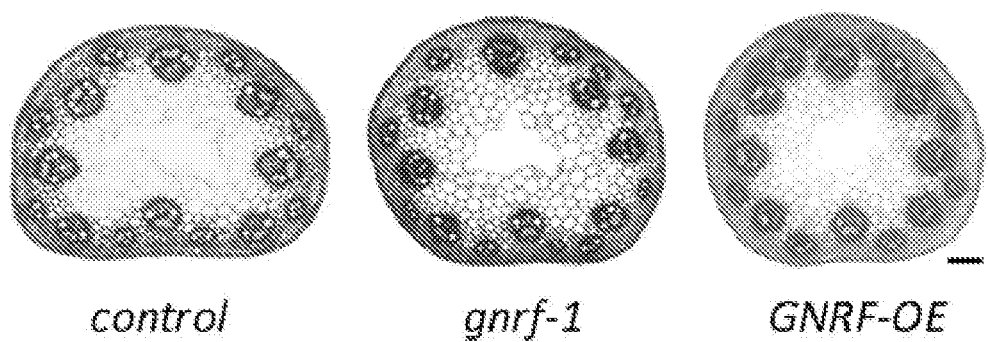
Figure 19B:
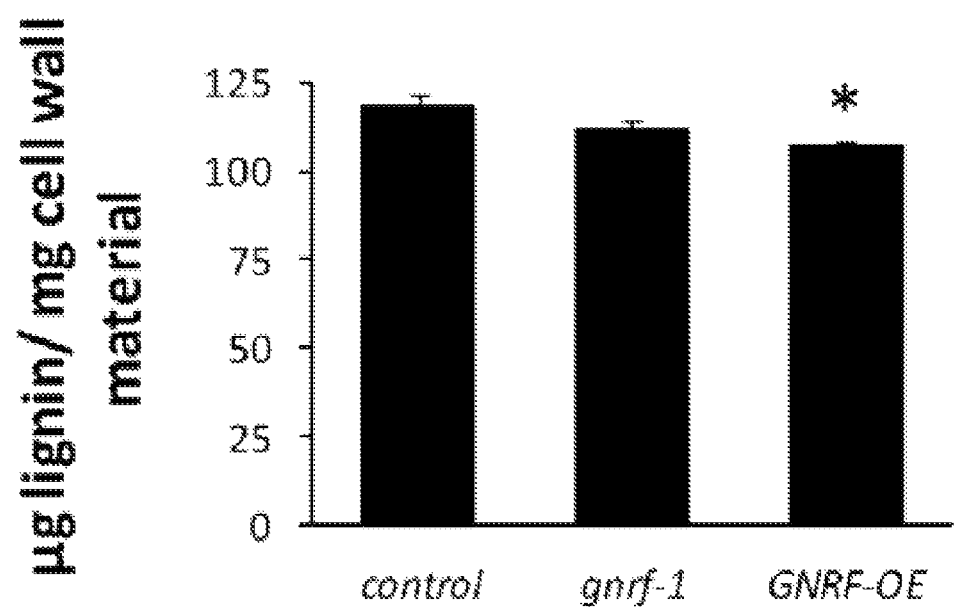

FIGS. 19A-B. Histo-chemical and compositional analysis of stem lignification. (A) Lignin staining of stem cross sections. First internodes of fully senesced plants were hand sectioned and stained with phloroglucinol-HCl to visualize lignin. Representative images were illustrated. Scale bar=50 μm. (B) Acetyl bromide soluble lignin content in senesced stems. Three to six individuals from each line were analyzed for the ASBL lignin content. *$p<0.05$.

DETAILED DESCRIPTION OF THE INVENTION

Several MYB proteins have been reported to regulate plant cell wall synthesis, but none has been shown to function as an activator in a grass. *Brachypodium distachyon* SECONDARY WALL ASSOCIATED MYB1 (SWAM1) was identified herein as a regulator of secondary cell wall biosynthesis based on gene expression and phylogeny. SWAM1 protein interacts with cellulose and lignin gene promoters in vitro and in vivo with preferential binding to AC-rich sequence motifs commonly found in cell wall gene promoters. Gain-of-function lines had greater above ground biomass without a change in flowering time while SWAM1-DR plants were severely dwarfed with a striking reduction in schierenchyma fiber lignin. Cellulose, hemicellulose, and lignin genes were significantly down-regulated in SWAM1-DR plants and up-regulated in SWAM1-OE plants. Considering lignin is inversely correlated with bioconversion efficiency phenotypes, ethanol yield was measured after culturing stems with *Clostridium phytolermentans*. While no effect in ethanol yield was observed for SWAM1-OE, yield was and a significantly increase for SWAM1-DR samples.

Interestingly, the analysis of phylogeny and synteny strongly suggests that the SWAM1 clade was present in the last common ancestor between eudicots and grasses, but is no longer present in the Brassicaceae. Collectively the data suggests that SWAM1 a transcriptional activator of secondary cell wall thickening and biomass accumulation in *B. distachyon* and potentially in food and energy crop species.

Thus, the present invention provides for the production of plants with increased biomass and their use in bio-ethanol or other biofuel production or as animal feed (e.g., as a silage or silage-type feed for animals, such as ruminants).

In describing and claiming the invention, the following terminology will be used in accordance with the definitions set forth below. Unless defined otherwise, all technical and scientific terms used herein have the same meaning as commonly understood by one of ordinary skill in the art to which this invention belongs. Any methods and materials similar or equivalent to those described herein can be used in the practice or testing of the present invention. Specific and preferred values listed below for radicals, substituents, and ranges are for illustration only; they do not exclude other defined values or other values within defined ranges for the radicals and substituents.

As used herein, the articles "a" and "an" refer to one or to more than one, i.e., to at least one, of the grammatical object of the article. By way of example, "an element" means one element or more than one element.

The term "about," as used herein, means approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 20%.

As used herein, "heterologous" in reference to a nucleic acid is a nucleic acid that originates from a foreign species, or, if from the same species, is modified from its native form in composition and/or genomic locus by deliberate intervention. For example, a promoter operably linked to a heterologous structural gene is from a species different from that from which the structural gene was derived or, if from the same species, one or both are modified from their original form. A heterologous protein may originate from a foreign species or, if from the same species, is modified from its original form by deliberate intervention.

Any method to increase expression/activity of the target gene is contemplated in the methods described herein. The term "introduced" in the context of inserting a nucleic acid into a cell, means "transfection" or "transformation" or "transduction" and includes reference to the incorporation of a nucleic acid into a eukaryotic or prokaryotic cell where the nucleic acid may be incorporated into the genome of the cell (e.g., chromosome, plasmid, plastid or mitochondrial DNA), converted into an autonomous replicon, or transiently expressed.

The term "isolated" refers to a factor(s), cell or cells which are not associated with one or more factors, cells or one or more cellular components that are associated with the factor(s), cell or cells in vivo.

As used herein, "nucleic acid" includes reference to a deoxyribonucleotide or ribonucleotide polymer in either single- or double-stranded form, and unless otherwise stated, encompasses known analogues having the essential nature of natural nucleotides in that they hybridize to single-stranded nucleic acids in a manner similar to naturally occurring nucleotides (e.g., peptide nucleic acids). Unless otherwise indicated, the term includes reference to the specified sequence as well as the complementary sequence thereof. Thus, DNAs or RNAs with backbones modified for stability or for other reasons are "polynucleotides" as that term is intended herein. Moreover, DNAs or RNAs comprising unusual bases, such as inosine, or modified bases, such as tritylated bases, to name just two examples, are "polynucleotides" as the term is used herein. It will be appreciated that a great variety of modifications have been made to DNA and RNA that serve many useful purposes known to those of skill in the art. The term polynucleotide as it is employed herein embraces such chemically, enzymatically or metabolically modified forms of polynucleotides.

The term "residue" or "amino acid residue" or "amino acid" are used interchangeably herein to refer to an amino acid that is incorporated into a protein, polypeptide, or peptide (collectively "protein"). The amino acid may be a naturally occurring amino acid and, unless otherwise limited, may encompass known analogs of natural amino acids that can function in a similar manner as naturally occurring amino acids.

The terms "polypeptide," "peptide," and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers.

As used herein "operably linked" includes reference to a functional linkage between a first sequence, such as a promoter and a second sequence, wherein the promoter sequence initiates and mediates transcription of the DNA sequence corresponding to the second sequence. Generally, operably linked means that the nucleic acid sequences being linked are contiguous and, where necessary to join two protein coding regions, contiguous and in the same reading frame.

As used herein "promoter" includes reference to a region of DNA upstream from the start of transcription and involved in recognition and binding of RNA polymerase and other proteins to initiate transcription. A "plant promoter" is a promoter capable of initiating transcription in plant cells. Exemplary plant promoters include, but are not limited to those that are obtained from plants, plant viruses, and bacteria which comprise genes expressed in plant cells such *Agrobacterium* or *Rhizobium*. Examples are promoters that preferentially initiate transcription in certain tissues, such as leaves, roots, seeds, fibers, xylem vessels, tracheids, or sclerenchyma. Such promoters are referred to as "tissue preferred." A "cell type" specific promoter primarily drives expression in certain cell types in one or more organs, for example, vascular cells in roots or leaves. An "inducible" or "regulatable" promoter is a promoter, which is under environmental/external signal control (e.g., chemically inducible promoter, such as alcohol inducible promoter). Examples of environmental conditions that may affect transcription by inducible promoters include anaerobic conditions or the presence of light. Additional examples of inducible promoters are the Adh1 promoter, which is inducible by hypoxia or cold stress, the Hsp70 promoter, which is inducible by heat stress, the PPDK promoter, which is inducible by light, and the promoter inducible by alcohol. Another type of promoter is a developmentally regulated promoter, for example, a promoter that drives expression during pollen development or senescence (see, for example, FIG. 6). Tissue preferred, cell type specific, developmentally regulated, and inducible promoters constitute "non-constitutive" promoters. A "constitutive" promoter is a promoter, which is active under most environmental conditions.

As used herein "recombinant" includes reference to a cell or vector, that has been modified by the introduction of a heterologous nucleic acid or that the cell is derived from a cell so modified. Thus, for example, recombinant cells express genes that are not found in identical form within the native (non-recombinant) form of the cell or express native genes that are otherwise abnormally expressed, under expressed or not expressed at all as a result of deliberate intervention.

As used herein, "vector" or "plasmid" includes reference to a nucleic acid used in transfection of a host cell and into which can be inserted a polynucleotide. Vectors are often replicons. Expression vectors permit transcription of a nucleic acid inserted therein. Typical vectors useful for expression of genes in higher plants are well known in the art and include vectors derived from the tumor-inducing (Ti) plasmid of *Agrobacterium tumefaciens* described by Rogers, et al., (1987) Meth. Enzymol. 153:253-77. These vectors are plant integrating vectors in that on transformation, the vectors integrate a portion of vector DNA into the genome of the host plant. Exemplary *A. tumefaciens* vectors are plasmids pKYLX6 and pKYLX7 of Schardl, et al., (1987) Gene 611-11, and Berger, et al., (1989) Proc. Natl. Acad. Sci. USA, 86:8402-6.

As used herein, a "recombinant expression cassette" is a nucleic acid construct, generated recombinantly or synthetically, with a series of specified nucleic acid elements, which permit transcription of a particular nucleic acid in a target cell. The recombinant expression cassette can be incorporated into a plasmid, chromosome, mitochondrial DNA, plastid DNA, virus, or nucleic acid fragment. Typically, the recombinant expression cassette portion of an expression vector includes, among other sequences, a nucleic acid to be transcribed, and a promoter. For example, plant expression vectors may include (1) a pre-selected sequence under the transcriptional control of 5° and 3' regulatory sequences and (2) a dominant selectable marker. Such plant expression vectors may also contain, if desired, a promoter regulatory region (e.g., one conferring inducible or constitutive, environmentally- or developmentally-regulated, or cell- or tissue-specific/selective expression), a transcription initiation start site, a ribosome binding site, an RNA processing signal, a transcription termination site, and/or a polyadenylation signal.

Expression cassettes, vectors and in vitro culture methods for plant cell or tissue transformation and regeneration of plants are known and available to the art. See, e.g., Gruber, et al., "Vectors for Plant Transformation," in METHODS IN PLANT MOLECULAR BIOLOGY AND BIOTECHNOLOGY, supra, pp. 89-119.

As used herein, the term "plant" includes reference to whole plants, plant organs (e.g., leaves, stems, roots, etc.), seeds and plant cells and progeny of same. Plant cell, as used herein includes, without limitation, seeds, cultures, embryos, meristematic regions, callus tissue, leaves, roots, shoots, gametophytes, sporophytes, pollen, and/or microspores.

As used herein, "transgenic plant" includes reference to a plant, which comprises within its genome a heterologous polynucleotide. Generally, the heterologous polynucleotide is stably integrated within the genome such that the polynucleotide is passed on to successive generations. The heterologous polynucleotide may be integrated into the genome alone or as part of a recombinant expression cassette. "Transgenic" is used herein to include any cell, cell line, callus, tissue, plant part or plant, the genotype of which has been altered by the presence of heterologous nucleic acid including those transgenics initially so altered as well as those created by sexual crosses or asexual propagation from the initial transgenic.

"Bio-alcohols," such as "bio-ethanol," are biologically produced alcohols, most commonly ethanol, and less commonly propanol, butanol and methyl butenol, which are generally produced by the action of microorganisms and enzymes through the fermentation of sugars or starches, or cellulose. Ethanol fuel is the most common biofuel worldwide. Alcohol fuels are produced by fermentation of sugars derived from wheat, corn, sugar beets, sugar cane, molasses and any sugar or starch that alcoholic beverages can be made from (like potato and fruit waste, etc.). The ethanol production methods used are enzyme digestion (to release sugars from stored starches), fermentation of the sugars, distillation and drying. The distillation process requires energy input for heat (often unsustainable natural gas fossil fuel, but cellulosic biomass, such as the waste left after sugar cane is pressed to extract its juice, can also be used more sustainably). Ethanol can be used in engines as a replacement for gasoline.

"Biomass" or "biofuel" is material derived from recently living organisms. This includes plants, animals and their by-products. For example, manure, garden waste and crop residues are all sources of biomass. It is a renewable energy source based on the carbon cycle, unlike other natural resources such as petroleum, coal, and nuclear fuels. It is used to produce power, heat and steam and fuel, through a number of different processes. "Agrofuels" are "biofuels" which are produced from crops. There are two common strategies of producing liquid and gaseous agrofuels. One is to grow crops high in sugar (sugar cane, sugar beet, and sweet sorghum) or starch (corn/maize), and then use yeast fermentation to produce alcohol (e.g., ethanol). The second is to grow plants that contain high amounts of vegetable oil, such as oil palm, soybean, algae, jatropha, or pongamia pinnata. When these oils are heated, their viscosity is reduced, and they can be burned directly in a diesel engine, or they can be chemically processed to produce fuels such as biodiesel. Wood and its byproducts can also be converted into biofuels such as woodgas, methanol or ethanol fuel. It is also possible to make cellulosic ethanol from non-edible plant parts.

Numerous methods for introducing foreign genes into plants (e.g., plant cells) are available to an art worker, including biological and physical plant transformation protocols. See, e.g., Miki, et al., "Procedure for Introducing Foreign DNA into Plants," in METHODS IN PLANT MOLECULAR BIOLOGY AND BIOTECHNOLOGY, Glick and Thompson, eds., CRC Press, Inc., Boca Raton, pp. 67-88 (1993). The methods chosen vary with the host plant, and include chemical transfection methods such as calcium phosphate, microorganism-mediated gene transfer such as *Agrobacterium* mediated transformation (Horsch, et al., (1985) Science 227:1229-31), microprojectile-mediated transformation, electroporation (Riggs, et al., (1986) Proc. Natl. Acad. Sci. USA 83:5602-5606), micro-injection (Crossway, et al., (1986) Biotechniques 4:320-334; and U.S. Pat. No. 6,300,543), direct gene transfer (Paszkowski, et al., (1984) EMBO J. 3:2717-2722), sonication (Zang, et al., (1991) BioTechnology 9:996), liposome or spheroplast fusions (Deshayes, et al., (1985) EMBO J. 4:2731; and Christou, et al., (1987) Proc. Natl. Acad. Sci. USA 84:3962), protoplast transformation, macroinjection, DNA uptake by germinating pollen and DNA uptake in embryos by swelling (Potrykus, *Physiol. Plant* (1990), 269-273), and biolistic bombardment (see, for example, Sanford, et al., U.S. Pat. No. 4,945,050; WO 91/10725; and McCabe, et al., (1988) Biotechnology 6:923-926; Tomes, et al., Direct DNA Transfer into Intact Plant Cells Via Microprojectile Bombardment. pp. 197-213 in Plant Cell, Tissue and Organ Culture, Fundamental Methods eds. O. L. Gamborg & G. C. Phillips, Springer-Verlag Berlin Heidelberg New York, 1995).

Once the DNA introduced is integrated into the genome of the plant cell, it is generally considered stable and is also retained in the progeny of the originally transformed cell. It can contain a selection marker Which mediates, for example, resistance to a biocide such as phosphinothricin or an antibiotic such as kanamycin, G 418, bleomycin or hygromycin, to the transformed plant cells or which permits selection via the presence or absence of certain sugars or amino acids. The marker chosen should therefore allow the selection of transformed cells over cells which lack the DNA introduced.

Once transformed, these cells can be used to regenerate transgenic plants in any manner available to the art. Seeds may be obtained from the plant cells. Two or more generations can be grown in order to ensure that the phenotype characteristic is stably retained and inherited. Also, seeds can be harvested in order to ensure that the phenotype in question or other characteristics have been retained.

The invention also relates to propagation material of the plants according to the invention, for example fruits, seeds, tubers, rootstocks, seedlings, cuttings, calli, protoplasts, cell cultures, tissues and the like.

As used herein, "an increase" in yield or growth is about 1% to about 10%, or less than about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, or about 30% or higher such as less than about 35%, about 40% about 45%, or about 50% increase in yield (e.g., grain/crop yield) or growth, as compared to a wild-type plant.

"Increase expression" refers to an increase in expression of protein or RNA. This increase can be from about 0.5% to 100% increase of expression of the gene, including about 1% to about 10%, or about 20%, about 25%, about 30%, about 35%, about 40%, about 45%, about 50%, about 55%, about 60%, about 65%, about 70%, about 75%, about 80%, about 85%, about 90%, about 95%, or about 100% as compared to a wild-type plant.

In one embodiment, the sequences mentioned herein also comprise variations that are at least about 50% or about 60% or about 70%, about T1%, about 72%, about 73%, about 74%, about 75%, about 76%, about 77%, about 78%, or about 79%, or at least about 80%, about 81%, about 82%, about 83%, about 84%, about 85%, about 86%, about 87%, about 88%, or about 89%, or at least about 90%, about 91%, about 92%, about 93%, or about 94%, or at least about 95%, about 96%, about 97%, about 98%, or about 99% sequence identity, compared to the sequences provided herein using one of alignment programs available in the art using standard parameters. In one embodiment, the differences in sequence are due to conservative amino acid. changes. In another embodiment, the protein sequence has at least 80%, or at least 85%, at least 90% or at least 95% sequence identity with the sequences provided herein and can be bioactive.

Methods of alignment of sequences for comparison are available in the art. Thus, the determination of percent identity between any two sequences can be accomplished using a mathematical algorithm. Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters.

The terms "comprises," "comprising," and the like can have the meaning ascribed to them in U.S. Patent Law and can mean "includes," "including" and the like. As used herein, "including" or "includes" or the like means including, without limitation.

The following examples are intended to further illustrate certain particularly preferred embodiments of the invention and are not intended to limit the scope of the invention in any way.

EXAMPLES

Example I

*Brachypodium distachyon* SWAM1 is a positive regulator of secondary cell wall synthesis and biofuel feedstock attributes and is not found in the Brassicaceae Introduction A large portion of plant biomass consists of secondary cell walls rich in cellulose, hemicelluloses, and lignin. It was the innovation of such walls and vascular cells that allowed plants to grow large and colonize areas further inland away from bodies of water. Diversification of vascular systems included the appearance of numerous arrangements of vasculature and the most advanced and varied are the angiosperms (Worsdell, 1902). Among the many distinctions between eudicotyledons and grasses are vascular patterning and the function and composition of cells with secondary walls (Esau, 1977; Kellogg, 2001; Vogel, 2008). Those aspects profoundly influence plant form and function as a food source for humans and animals, a raw material in the pulp and paper industry, and a biofuel feedstock. As with agronomic food crops, yield is the foremost energy crop trait and cultivation should demand few inputs (Jessup, 2009). Energy crop quality can be gauged by the type and relative quantity of fuel that can be derived from a unit of raw material. The transcriptional regulation of each secondary wall polymer and the manner in which they interact influences function as well as industrial feedstock quality (Carroll and Somerville, 2009).

The transcriptional network that governs the regulation of secondary cell wall thickening in eudicots consists of numerous MYB family transcription factors (Zhong et al., 2010; Hussey et al., 2013; Schuetz et al., 2013). MYB proteins are present in all eukaryotes and are generally encoded by large gene families (Katiyar et al., 2012; Du et al., 2013). For example, *Arahidopsis thaliana* and rice (*Oryza sativa*) have an estimated 197 and 155 MYBs, respectively. In addition to overall sequence similarity, the sub-families are categorized based on the number and type of DNA-binding domains in each protein, which ranges from one to four copies. The majority of plant MYB proteins harbor two DNA-binding domains and the so called R2R3-

MYB group is extensively described in several plant species including *A. thaliana*, *Populus*, orange (*Citrus sinensis*), maize (*Zea mays*), and rice (Wilkins et al., 2009; Katiyar et al., 2012; Du et al., 2013; Liu et al., 2014). The *A. thaliana* MYB proteins known to regulate the cell wall transcription network include AtMYB46/83/58/63/85/20/52/54/69/103/4/32/75 (Hussey et al., 2013; Zhao and Bartley, 2014). Among these, AtMYB46 and AtMYB83 are regulators capable of activating downstream transcription factors and cell wall genes (Ko et al., 2014). Over-expression of AtMYB46 or AtMYB83 resulted in thicker secondary cell walls in the xylem vessels and dominant repression resulted in thinner walls (Thong et al., 2007; McCarthy et al., 2009). Other proteins specifically regulate the biosynthesis of a single component of the cell wall. For instance, AtMYB58 and AtMYB63 directly bind the promoters of lignin genes to activate lignin biosynthesis (Zhou et al., 2009). Dominant repression of these two proteins resulted in a reduction of secondary wall thickening and lignin content. As a result, these plants were unable to grow upright. On the other hand, over-expression resulted in increased lignin pathway gene expression and ectopic deposition of lignin in cells that are normally not lignified. However, over-expression of either AtMYB58 or AtMYB63 did not result in thicker secondary cell walls (Zhou et al., 2009). Several other MYBs including AtMYB20/54/69/85/103 are highly expressed in stem tissue and activate secondary wall thickening (Hussey et al., 2013). AtMYB85 can activate genes in the lignin pathway and dominant repression resulted in a significant reduction in thickness of interfascicular and xylary fiber walls and over-expression resulted in ectopic deposition of secondary cell walls in stem epidermis and cortex (Zhong et al., 2008). Dominant repression AtMYB103/52/54/69 transgenes also reduced secondary wall thickening in interfascicular and xylary fiber cells; however, none had a significant effect on the vessels (Zhong et al., 2008). The research conducted on *A. thaliana* MYB proteins implies they play crucial regulatory roles as activators and repressors of cell wall biosynthesis.

The three variants of the AC element, AC-I (ACCTACC), AC-II (ACCAACC), and AC-III (ACCTAAC), present in promoters of many lignin pathway genes have been shown to interact with MYB protein to influence transcription (Lois et al., 1989; Hatton et al., 1995; Raes et al., 2003). The AC element was further described to have four more variations by interchanging the T with a C at the last base position, ACC(T/A)A(A/C)(C/T) and named the secondary wall MYB responsive element (SMRE) or the AtMYB46 responsive cis-element (M46RE) (Kim et al., 2012; Zhong and Ye, 2012). This element was over represented in the promoters of genes up regulated by the over-expression of AtMYB46 under an inducible promoter. The representation was greatest among cellulose, hemicellulose, and lignin genes associated with AtMYB46 regulated secondary cell wall biosynthesis (Kim et al., 2012; Kim et al., 2013). Interestingly, interactions between MYB proteins and AC element like motifs can result in either transcriptional activation or repression (Rats et al., 2003).

Unlike *A. thaliana* and *Populus*, the current transcriptional regulatory network for grass secondary cell wall biosynthesis is rather lacking (Handakumbura and Hazen, 2012). To date, the function of two MYB transcription factors has been demonstrated in a grass. ZmMYB31 and PvMYB4 are two transcriptional repressors characterized in maize and switchgrass, respectively. Like their close homologs in *A. thaliana* (AtMYB4) and *Eucalyptus gunnii* (EgMYB1) they directly repress lignin gene expression by binding to the AC elements found in the promoters of these genes and subsequently regulate cell wall biosynthesis (Jin et al., 2000; Legay et al., 2007; Fornalé et al., 2010; Shen et al., 2012). Rice and maize orthologs of AtMYB46 and AtMYB83 are the only grass MYB activators characterized thus far. These proteins are capable of activating secondary cell wall biosynthetic pathways when over-expressed in *A. thaliana* (Thong et al., 2011). However, no MYB activators have been functionally characterized and shown to directly activate cell wall genes in grasses. Herein candidate genes are identified for the positive regulation of secondary cell wall biosynthesis based on co-expression analysis and protein phylogenies in the model monocot *Brachypodium distachyon*. The function of a MYB transcription factor that has no orthologous counterpart in *A. thaliana* and other Brassicaceae, SECONDARY WALL ASSOCIATED MYB1 (Bradi2g47590), is demonstrated herein via overexpression and dominant repressor lines. In addition, it is shown that SWAM1 protein directly activates cell wall gene promoters to regulate wall thickening.

Materials and Methods

Phylogenetic Analysis

The following genome annotation versions were mined, which were current at the time of this analysis: *S. lycopersicum*, iTAG 2.3, *P. persica*, v1.0, *M. truncatula*, Phytozome v4.1, *P. trichocarpa*, Phytozome v3.0, *C. rubella*, Phytozome v1.0, *A. thaliana*, TAIR10, *A. lyrata*, Phytozome v1.0, *C. papaya* ASGPBv0.4, rice, *B. distachyon*, Phytozome v2.1, MSU v7.0 *P. virgatum*, Phytozome v1.1. Two different processes were used to identify SWAM1 homologs and related proteins from different genomes. To establish BLASTP criteria for quickly identifying specific proteins from diverse genomes, a global analysis was conducted with a small number of species using HMMFR 3.0 (Finn et al., 2011) to identify the putative R2R3 MYB protein sequences in *O. sativa*, *S. lycopersicum*, *P. persica* and *M. truncatula* with an in-house Hidden Markov Model profile based on the 126 R2R3 MYB proteins in *A. thaliana* (Dubos et al., 2010). From these five species and the *B. distachyon* MYBs, identified previously (International *Brachypodium* Initiative, 2010), a phylogenetic tree was built with the whole R2R3-type MYB family using a Neighbor-joining algorithm and 500 bootstraps in MEGA v.5.2.2 (Tamura et al., 2011). Homologs of SWAM1 were selected if they were included in the same clade and supported by a bootstrap score≥50. To identify the homologs of SWAM1 in more species, BLASTP was used to search the following species: *P. virgatum*, *P. trichocarpa*, *A. Lyrata*, *C. papaya* and *C. rubella*. Sequences were included with E values≤E-60, which recalled all of the SWAM1 homologs identified based on the topology of the R2R3-type MYB phylogeny described above. Then the SWAM1 homologs were finalized from all species by further phylogenetic analysis with MrBayes. To identify homologs of AtMYB50, AtMYB61, AtMYB46 and AtMYB83 in poplar, rice and switchgrass, the recent publication of Zhao (2014) was used. To identify these proteins in the other species, the best BLASTP hit was included for AtMYB50, AtMYB61, AtMYB46 and AtMYB83. There was no evidence of gene family expansion in these groups, since the top two BLASTP hits for each target had obviously lower E values. Supplementary Table 2 contains the names and protein sequences used for the phylogenetic study of SWAM1. The protein sequences were aligned with MAFFT with the L-INS-I model, which allows local iterative refinement and shows better performance than CLUSTAL or MUSCLE, in general (Katoh et al., 2002; Thompson et al., 2011). To calculate the protein sequence similarity, the MUSCLE alignment incorporated into Geneious v.6 (Biomatters, Aukland, NZ) was used. The phylogeny for SWAM1 and related sequences in the AtMYB50 clade with the AtMYB83 clade as the outgroup was constructed using MrBayes v3.2. Two million generations yielded an average standard deviation of the split frequency of 0.0128, which indicates a relatively high confidence topology (Ronquist et al., 2012).

Synteny Analysis

The syntenic region of the Swam1 in the genomes of papaya, poplar, and *A. thaliana* was analyzed with the SynFind, which is incorporated within CoGe: Comparative Genomics (genomevolution.org/CoGe/) (Lyons et al., 2008).

Yeast One-Hybrid Screens

Yeast one-hybrid screens were conducted as previously reported (Pruneda-Paz et al., 2009). Two synthetic promoters were generated for the AC-like element (ACCAAC) and the mutated AC-like element (TTTAAC) by fusing four copies of the sequence in tandem. A spacer sequence of tttagatatcataa (SEQ ID NO: 1) was included at the 3'end of the synthetic promoters. Sequence confirmed clones were recombined with pLacZi plasmid (Clonetech) containing the LacZ reporter gene and stably integrated into the YM4271 yeast strain. SWAM1 was fused in frame with GAL4 activation domain in pDEST22 destination vector.

Plant Material and Growth Conditions

*B. distachyon* (L.) line Bd21-3 was used as the genetic background. Wild type, control, and mutant seeds were imbibed on moist paper towels for seven days at 4° C. and planted in potting mix (#2; Conrad Fafard Inc. Agawam, Mass.). Plants were grown at control conditions in a growth chamber at 20° C. in 20 h: 4 h light: dark cycles at a fluence rate of 220 $\mu mol \cdot m^{-2} s^{-1}$ and relative humidity of 68%.

Plasmid Construction and Plant Transformation

The full-length coding region of SWAM1 (Bradi2g47590) was PCR amplified from Bd21-3 stem cDNA to include the stop codon using Phusion high-fidelity DNA polymerase (New England BioLabs) and cloned into pENTR/D-TOPO vector (Invitrogen). Sequence confirmed plasmid was recombined with pOL001 ubigate ori1 destination vector (modified from pOL001, described in (Vogel et al., 2006)) to generate the MYB48 gain-of-function construct (SWAM1-OE). A 39 nucleotide dominant repressor CRES sequence (Mitsuda et al., 2011) was synthesized using overlapping oligonucleotides with attB2 and attB5 flanking sites and cloned into pDONR 221 P5-P2. Full-length coding region of SWAM1 without the stop codon (MYB48NS) was cloned into pDONR 221 P1-P5r. CRES and MYB48NS entry clones were recombined with pOL001 ubigate ori1 destination vector to generate the MYB48 dominant repressor construct (SWAM1-DR). All constructs were transformed into *Agrobaterium tumefaciens* strain AGL1 via electroporation for calli transformations. *Brachypodium distachyon* calli transformations were carried out with minor modifications as previously described (Handakumbura et al., 2013). Primary transgenic were PCR confirmed for the hygromycin resistance gene and propagated for three subsequent generations and the resulting $T_4$ progeny were PCR confirmed for presence of the hygromycin phosphotransferase II gene using a Phire Plant Direct PCR Kit (Thermo Scientific) according to manufactures specifications. PCR confirmed transgenics were used for subsequent experiments.

Measurements of Transcript Abundance and Localization

Total RNA was extracted using a kit (Plant RNaeasy, Qiagen, Valencia, Calif.) according to the manufactures instructions. First, second, and third nodes and internodes of the tallest stem were frozen in liquid nitrogen from developmentally comparable individuals at inflorescence immergence, stage 51 on the *B. distachyon* BBCH-scale (Hong et al., 2011). On-column DNA digestions were performed using RNase-free DNase I (Qiagen). First strand cDNA was synthesized using oligo dT primers (Invitrogen) and QRT-PCR reactions were performed in triplicate as previously described (Handakumbura et al., 2013). Values were normalized against two housekeeping genes, BdUBC18 (UBIQUITIN-CONJUGATING ENZYME 18) and BdGapDH (Hong et al., 2008). Primers were designed using QuantiPrime primer design tool (Arvidsson et al., 2008).

RNA in situ hybridization was performed as previously described (Handakumbura et al., 2013) using stem cross sections of the first internode of the tallest stem at the completion of flowering, stage 65 on the *B. distachyon* BBCH-scale.

Microscopy

First internode of the tallest stem at complete senescence was used for histochemical analysis. Hand-cut stem cross sections were stained with phloroglucinol-HCl and observed under an Eclipse E200MV R microscope (Nikon) and imaged using a PixeLINK 3 MP camera. Images captured at 4× magnification were used for area measurements by freehand tracing of a perimeter in ImageJ (rsb.info.nih.gov/ij/). First internode of the tallest stem of mutant and vector control plants were excised when the inflorescence was first visible from the flag leaf and fixed in 2% glutaraldehyde in 50 mM phosphate buffer (33 mM Na2HPO4, 1.8 mM NaH2PO4 and 140 mM NaCl, pH 7.2) at room temperature for 2 hours. Next, samples were post-fixed in phosphate buffered OsO4 under same conditions. Samples were rinsed thrice with water and dehydrated in a graded ethanol series. Fixed tissue was infiltrated with 30%, 50%, 70% and 10 0% Spurr's resin for 1 hour each. Samples were infiltrated overnight in 100% resin, embedded in fresh resin and allowed to solidify in an oven. Embedded samples were sectioned using an ultra-cut microtome; post-fixed with uranyl acetate and lead citrate, and observed with an electron microscope.

Acetyle Bromide Soluble Lignin Measurements

Acetyl bromide soluble lignin content was measured as previously described (Foster et al., 2010). Briefly, 1.5 mg of senesced ground stem tissue was incubates with 100 µl of freshly made acetyl bromide solution (25% v/v acetyl bromide in glacial acetic acid) and incubated at 50° C. for 2 hours followed by an additional hour of incubation with vortexing every 15 min. Next, samples were cooled on ice to room temperature, and mixed with 400 µl of 2 M HaOH and 70 µl of freshly prepared 0.5 M hydroxylamine hydrochloride. A total volume of 2 ml was obtained by adding 1.43 ml glacial acetic acid. Absorbance was measured at 280 nm wavelength using a plate reader. Six to sixteen individuals from three events were analyzed for each transgene and percent acetyl bromide soluble lignin was calculated as previously described (Foster et al., 2010).

Cell Wall Digestibility Measurements

Fully senesced stems were washed with 70% ethanol at 70° C. for 1 h to remove soluble cell wall material and was air dried overnight. Next they were ground using a ball mill and weighed into individual wells in 20 mg duplicated and fermented with *Clostridium phytophementans* as previously described (Lee et al., 2012; Lee et al., 2012). Nine individuals from three independent events were analyzed in duplicate for each transgene.

Chromatin Immunoprecipitation

About 2 g of whole stems tissue was harvested from three week old plants and treated for 15 min under vacuum with cross-linking buffer (10 mM Tris, pH 8.0, 1 mM EDTA, 250 mM sucrose, 1 mM PMSF and 1% formaldehyde). Cross-linking was quenched using 125 mM glycine, pH 8.0, under vacuum for 5 min, followed by three washing steps in double-distilled water. Next the tissue was rapidly frozen in liquid nitrogen, ground to a fine power using a mortar and pestle and stored at −80° C. Chromatin was extracted using a kit (Zymo-spin) according to the manufacturer specification. Cross-linked samples were washed with the provided Nuclei prep buffer, resuspended in chromatin shearing buffer and sonicated on ice for four cycles using 40% amptitude. 100 μl of the sheared chromatin was incubated with the anti-GFP antibody overnight at 4° C. Samples were recovered using ZymoMag Protein A beads, washed thrice with the chromatin wash buffers and eluted using the chromatin elusion buffer. Eluted DNA was treated with 5M NaCl at 75° C. for 5 min and incubated with Proteinase K at 65° C. for 30 min, ChiP DNA was purified using the provide columns and eluted using 8 μl of elusion buffer. Triplicate QRT-PCR reactions were performed for three biological replicates using Quantifast SYBR Green PCR Kit (QIAGEN), with 2 ng of DNA with the following cycler conditions: 2 min at 95° C., followed by 40 cycles of 15 s at 95° C., 20 s at 55° C. and 20 s at 68° C. Results were normalized to the input DNA, using the following equation: $100 \times 2^{(Ct\ input\cdot 3.32 - Ct\ ChIP)}$.

Statistical Analysis

For each measurement three different $T_4$ families were analyzed for each transgene. Student's t-tests were performed in R v2.15.0. Significance was set a $P<0.05$.

Accession Numbers

AS1 (At2G37630), AtMYB1 (At3G09230), AtMYB3R4 (At5g11510), AtMYB3R-1 (At4g32730), AtMYB4 (At4G38620), AtMYB7 (At2G16720), AtMYB16 (At5G15310), AtMYB20 (At1G66230), AtMYB32 (At4G34990), AtMYB36 (At5G57620), AtMYB37 (At5G23000), AtMYB42 (At4G12350), AtMYB43 (At5G16600), AtMYB46 (At5G12870), AtMYB48 (At3G46130), AtMYB50 (At1G57560), AtMYB55 (At4G01680), AtMYB58 (At1G16490), AtMYB59 (At5G59780), AtMYB61 (At1G09540), AtMYB63 (At1G79180), AtMYB71 (AT3G24310), AtMYB79 (AT4G13480), AtMYB83 (At3G08500), AtMYB85 (At4G22680), AtMYB86 (At5G26660), AtMYB91 (At2G37630), AtMYB103 (At1G63910), AtMYB106 (At3G01140), AtMYB109 (At3G55730), BdCAD1 (Bradi3g17920), BdCESA4 (Bradi4g28350), BdCESA7 (Bradi2g30540), BdCESA8 (Bradi2g49912), BdCOMT4 (Bradi3g16530) BdGapDH (Bradi3g14120), BdGT47D3 (Bradi2g59400), BdUBC18 (Bd4G00660), EgMYB1 (CAE09058), OsMYB46 (Os12g33070), PvMYB4 (JF299185), ZmMYB31 (GRMZM2G050305), ZmMY1346 (GRMZM2G052606). See Table 1 for BdMYB accession numbers.

TABLE 1

Secondary cell wall associated R2R3-type MYB transcription factors. *Brachypodium distachyon* MYBs co-regulated with BdCESA4/7/8 and BdCAD1, and BdCOMT4 were identified based on a correlation coefficient cut off of 0.8 for either BdCESA4/7/8 or BdCAD1 and BdCOMT4. Orthologs of the majority of the tightly co-regulated MYB transcription factors have already been implicated in secondary cell wall processes in *A. thaliana* and are listed below.

| Locus | Name | Most similar *A. thaliana* proteins | CESA4/7/8 correlation coefficient | CAD1/COMT4 correlation coefficient | References describing function in *A. thaliana* |
|---|---|---|---|---|---|
| Bradi4g06317 | BdMYB1 | AtMYB46/83 | 0.99 | 0.92 | (Zhong et al., 2007; McCarthy et al., 2009) |
| Bradi2g47590 | BdMYB48 | AtMYB50/61 | 0.99 | 0.96 | |
| Bradi3g17165 | BdMYB110 | AtMYB103 | 0.99 | 0.92 | (Öhman et al., 2013) |
| Bradi2g17982 | BdMYB31 | AtMYB50/61 | 0.99 | 0.87 | |
| Bradi5g20130 | BdMYB104 | AtMYB58/63 | 0.97 | 0.95 | (Zhou et al., 2009) |
| Bradi1g10470 | BdMYB2 | AtMYB52/54 | 0.97 | 0.89 | (Cassan-Wang et al., 2013) |
| Bradi3g56917 | BdMYB76 | AtMYB20/43 | 0.96 | 0.95 | (Ehlting et al., 2005; Zhong et al., 2008; Cui et al., 2013) |
| Bradi3g42430 | BdMYB69 | AtMYB42/85 | 0.96 | 0.88 | (Zhong et al., 2008) |
| Bradi5g15246 | BdMYB101 | AtMYB71/79 | 0.95 | 0.92 | |
| Bradi2g28910 | BdMYB39 | AtMYB71/79 | 0.95 | 0.82 | |
| Bradi2g17280 | BdMYB30 | AtMYB36/37 | 0.94 | 0.85 | (Muller et al., 2006) |
| Bradi3g36660 | BdMYB64 | AtMYB16/106 | 0.93 | 0.75 | (Folkers et al., 1997; Oshima et al., 2013) |
| Bradi4g29796 | BdMYB90 | AtMYB20/43 | 0.92 | 0.92 | (Ehlting et al., 2005; Zhong et al., 2008; Cui et al., 2013) |
| Bradi2g40620 | BdMYB44 | AtMYB50/61 | 0.92 | 0.72 | |
| Bradi4g04050 | BdMYB80 | AtMYB48/59 | 0.91 | 0.73 | (Mu et al., 2009) |
| Bradi4g36210 | BdMYB93 | AtMYB42/85 | 0.90 | 0.79 | (Zhong et al., 2008) |
| Bradi1g61397 | BdMYB18 | AtMYB50/61 | 0.90 | 0.68 | (Liang et al., 2005) |
| Bradi2g36730 | BdMYB41 | AtMYB50/61 | 0.89 | 0.98 | (Liang et al., 2005) |
| Bradi4g23967 | BdMYB109 | AtMYB4/7/32 | 0.88 | 0.99 | (Jin et al., 2000; Preston et al., 2004; Fornalé et al., 2014) |
| Bradi4g36460 | BdMYB94 | AtMYB4/7/32 | 0.84 | 0.97 | (Jin et al., 2000; Preston et al., 2004; Fornalé et al., 2014) |
| Bradi2g31887 | BdMYB40 | AtMYB3R4/3R-1 | 0.81 | 0.94 | (Haga et al., 2007; Haga et al., 2011) |
| Bradi1g51961 | BdMYB15 | AtMYB92 | 0.80 | 0.56 | |
| Bradi2g07677 | BdMYB25 | AtMYB3R4/3R-1 | 0.80 | 0.94 | (Haga et al., 2007; Haga et al., 2011) |
| Bradi4g03970 | BdMYB79 | AtMYB91; AS1 | 0.77 | 0.86 | (Ori et al., 2000) |
| Bradi2g37377 | BdMYB111 | AtMYB48/59 | 0.74 | 0.91 | (Mu et al., 2009) |
| Bradi2g55040 | BdMYB53 | AtMYB1/109 | 0.71 | 0.91 | |
| Bradi1g44070 | BdMYB12 | AtMYB20/43 | 0.71 | 0.86 | (Ehlting et al., 2005; Zhong et al., 2008; Cui et al., 2013) |
| Bradi1g20250 | BdMYB4 | AtMYB55/86 | 0.69 | 0.81 | |
| Bradi3g10067 | BdMYB112 | AtMYBR4/3R-1 | 0.62 | 0.80 | (Haga et al., 2007; Haga et al., 2011) |

TABLE S3

List of oligonucleotides used

| Primer Name | Sequence |
|---|---|
| attB1MYB48_F | ACAAGTTTGTACAAAAAAGCAGGCTCTATGGGGCGGCACGCGGGCACT (SEQ ID NO: 32) |
| attB2MYB48_R | ACCACTTTGTACAAGAAAGCTGGGTATCAAAAGTACTCGAGGTTGAAG (SEQ ID NO: 33) |
| attB5rMYB48_NS | RACAACTTTTGTATACAAAGTTGTAAAGTACTCGAGGTTGAAGTC (SEQ ID NO: 34) |
| attB5CRES_F | GgggACAACTTTGTATACAAAAGTTGCTGTTGATCTTGATCTTGAATTGAGATTGGGT (SEQ ID NO: 35) |
| attB2CRES_R | GgggACCACTTTGTACAAGAAAGCTGGGTATCAAGCAAAACCCAATCT (SEQ ID NO: 36) |
| attB5GFP_F | ggggACAACTTTGTATACAAAAGTTGCTATG GTG AGC AAG GGC GAG GAG (SEQ ID NO: 37) |
| attB2GFP_R | ggggACCACTTTGTACAAGAAAGCTGGGTATCA CTT GTA CAG CTC GTC CAT GCC (SEQ ID NO: 38) |
| attB1GFP_F | GgggACAAGTTTGTACAAAAAAGCAGGCTCTATGGTGAGCAAGGGCGAGG (SEQ ID NO: 39) |
| qPCRGT47-1_F | AATATAGCGCGCTGCATGTCCTC (SEO ID NO: 40) |
| qPCRGT47-1_R | AATATAGCGCGCTGCATGTCCTC (SEQ ID NO: 41) |
| qPCRMYB48CDS_F | AGGAAACAGGTGGTCGCAGATTG (SEQ ID NO: 42) |
| qPCRMYB48CDS_R | GCTTCTTCTTGAGGCAGCTGTTCC (SEQ ID NO: 43) |
| qPCRUBC18_F | GGAGGCACCTCAGGTCATTT (SEQ ID NO: 44) |
| qPCRUBC18_R | ATAGCGGTCATTGTCTTGCG (SEQ ID NO: 45) |
| qPCRGAPDH_F | TTGCTCTCCAGAGCGATGAC (SEQ ID NO: 46) |
| qPCRGAPDH_R | CTCCACGACATAATCGGCAC (SEQ ID NO: 47) |
| qPCRCAD1_F | AGGATAGAATGGGCAGCATCGC (SEQ ID NO: 48) |
| qPCRCAD1_R | ATCTTCAGGGCCTGTCTTCCTGAG (SEQ ID NO: 49) |
| qPCRCOMT4_F | TGGAGAGCTGGTACTACCTGAAG (SEQ ID NO: 50) |
| qPCRCOMT4_R | CGACATCCCGTATGCCTTGTTG (SEQ ID NO: 51) |
| qPCRCESA4_F | GCGTTTCGCATACACCAACACC (SEQ ID NO: 52) |
| qPCRCESA4_R | ACTCGCTAGGTTGTTCAGTGTGG (SEQ ID NO: 53) |
| qPCRCESA7_F | GCGATTCGCCTACATCAACACC (SEQ ID NO: 54) |
| qPCRCESA7_R | GGCTGGCAAATGTGCTAATCGG (SEQ ID NO: 55) |

TABLE S3-continued

List of oligonucleotides used

| Primer Name | Sequence |
|---|---|
| qPCRCESA8_F | CAAAGCACAAGTTCCGCCTGTG (SEQ ID NO: 56) |
| qPCRCESA8_R | TGGCTCGTATGCATCTGTCAAATC (SEQ ID NO: 57) |
| qUBC18p_F | AAGGCTTGAACATGACAGCA (SEQ ID NO: 58) |
| qUBC18p_R | ATGAAATGGGCACCTGAAAA (SEQ ID NO: 59) |
| qCESA4p-1_F | TGCAAAAGGCCTCAGCTAAT (SEQ ID NO: 60) |
| qCESA4p-1_R | TGGTGGCATACAAAACCTCA (SEQ ID NO: 61) |
| qCESA4p-2_F | CTTCACGCTCACTCACCATC (SEQ ID NO: 62) |
| qCESA4p-2_R | CGGAAGACCAAGAATGAAGC (SEQ ID NO: 63) |
| qCESA8p-2_F | CTTGCTCTCACCGTCCTGA (SEQ ID NO: 64) |
| qCESA8p-2_R | GGTTTCGAAGCGAAGGTGAC (SEQ ID NO: 65) |
| qCADp-1_F | TTCCTATTGCAAGTACATCATGC (SEQ ID NO: 66) |
| qCADp-1_R | TATCGTGTGCTGCCCATCTA (SEQ ID NO: 67) |
| qCADp-3_F | AAACTGTTTGAAAATCAAATCTGC (SED ID NO: 68) |
| qCADp-3_R | GGAAGTTGTCGTGGGATCAG (SEQ ID NO: 69) |
| qCOMTp-2_F | TCGAGAAATAATGGTTCAGACG (SEQ ID NO: 70) |
| qCOMTp-2_R | AGATATACTTGTTGTCGCGAAG (SEQ ID NO: 71) |
| Hpt_F | AGAATCTCGTGCTTTCAGCTTCGA (SEQ ID NO: 72) |
| Hpt_R | TCAAGACCAATGCGGAGCATATAC (SEQ ID NO: 73) |
| Myb48_probe_aF | GCATGGCGCATTTTGACTTCAACC (SEQ ID NO: 74) |
| Myb48_probe_aR | CTA CAC AAT GTT CAC ATT CCT ATA CC (SEQ ID NO: 75) |

Results

Co-Expression Analyses Reveal a Suite of Secondary Cell Wall Associated MYB Transcription Factors Microarray and co-expression analyses have aided in the understanding of gene function in a variety or organisms both in terms of intraspecific as well as interspecific comparisons (Brown et al., 2005; Persson et al., 2005; Mutwil et al., 2011). Not surprisingly, regulators of secondary cell wall biosynthesis are commonly highly expressed in tissues containing secondary cell walls and are co-expressed with the downstream genes they activate. Therefore, co-expression analyses was performed with secondary cell wall related cellulose genes BdCESA4, BdCESA7, BdCESA8 and the lignin-related genes BdCAD1 and BdCOMT4 to identify candidate MYB transcription factors that putatively regulate secondary cell wall biosynthesis (Table 1) using a previously described microarray data set (d'Yvoire et al., 2012; Dalmais et al., 2013; Handakumbura et al., 2013; Trabucco et al., 2013). 26 BdMYB transcription factors that are co-regulated with BdCESA4/7/8 and BdCAD1, and BdCOMT4 were identified. Many these are part of sub-clades described as having an association with secondary cell wall biosynthesis based on genes characterized in *A. thaliana* (Zhao and Bartley, 2014). BdMYB48 (Bradi2g47590), hereby referred to as SWAM1, was further characterized.

Figure 1A:
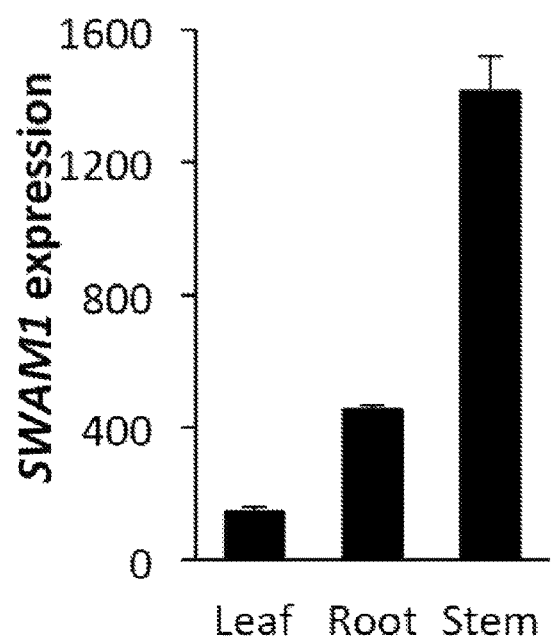
FIGS. 1A-C. Phylogenetic analysis of SWAM1 and related sequences suggests that the SWAM clade is present in diverse dicots, but absent from the Brassicaceae. Relative transcript abundance of SWAM1 in leaf, root and stem tissue measured with a microarray. Mean±standard deviation of three biological replicates (A). RNA in situ hybridization illustrating SWAM1 transcript localization in stem cross sections six weeks post germination (B) Sections were taken through the first internode and probed with anti-sense probes and imaged at 20× magnification. ep; epidermis, if; interfascicular fiber cells, xy; xylem, ph; phloem, pi; pith. A subclade of the MYB family illustrating amino acid sequence similarity between *Arabidopsis thaliana* (red), rice (blue) and *Brachypodium distachyon* (black). Red labels represent monocot species, including *Brachypodium dystachyon* (Bradi), rice (*Oryza sativa*, Os) and switchgrass (*Panicum virgatum*, Pavir). The black labels represent Brassicaceae species, including *Arabidopsis thaliana* (At), *Arabidopsis lyrata* (Alyrata), and *Capsella rubella* (Crubella). The blue labels represent other dicotyledonous species, including poplar (Potri), potato (Ltuber), peach (Ppersica), papaya (Cpapaya), and *Medicago truneatula* (Medtr). We constructed the phylogeny using MrBayes v3.2. The MYB46/83 clade members from all the species were chosen as the outgroup.
Figure 1B:
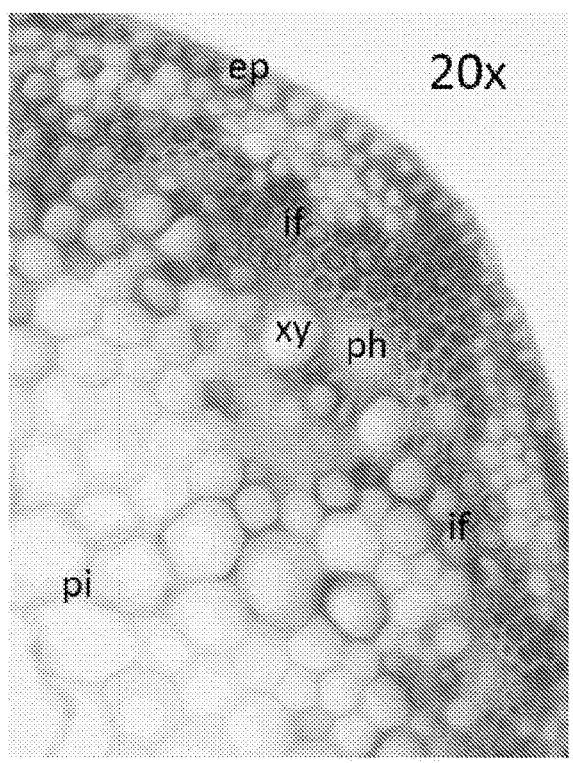

SWAM1 is Highly Expressed in Stein and is Localized to the Interfascicular Fibers To investigate SWAM1 transcript abundance in leaf, stem and root, the previously described *B. distachyon* microarray data set (Handakumbura et al., 2013) was used. SWAM1 transcript abundance in stems was approximately six and three-fold greater relative to leaf and root, respectively (FIG. 1A). Grass stems are substantially enriched for secondary cell walls (Matos et al., 2013) and account for a larger proportion of above ground plant biomass. However, not all cell types in the stem undergo secondary wall development. To confirm that SWAM1 gene expression is associated with those cells undergoing secondary wall thickening, RNA in situ hybridization was carried out on stem cross sections at inflorescence immergence (FIG. 1B). Similar to what was reported for BdCESA4 and BdCESA7 (Handakumbura et al., 2013), SWAM1 transcripts were localized to cell types with thickened secondary walls at this stage of development. They were mainly localized to the epidermis, sclerenchyma fibers, and xylem cells in both small and large vascular bundles. No hybridization was detected in the parenchyma cells and phloem fibers. Hybridization with control SWAM1 sense probe showed no labeling as expected (data not shown).

Figure 1C:
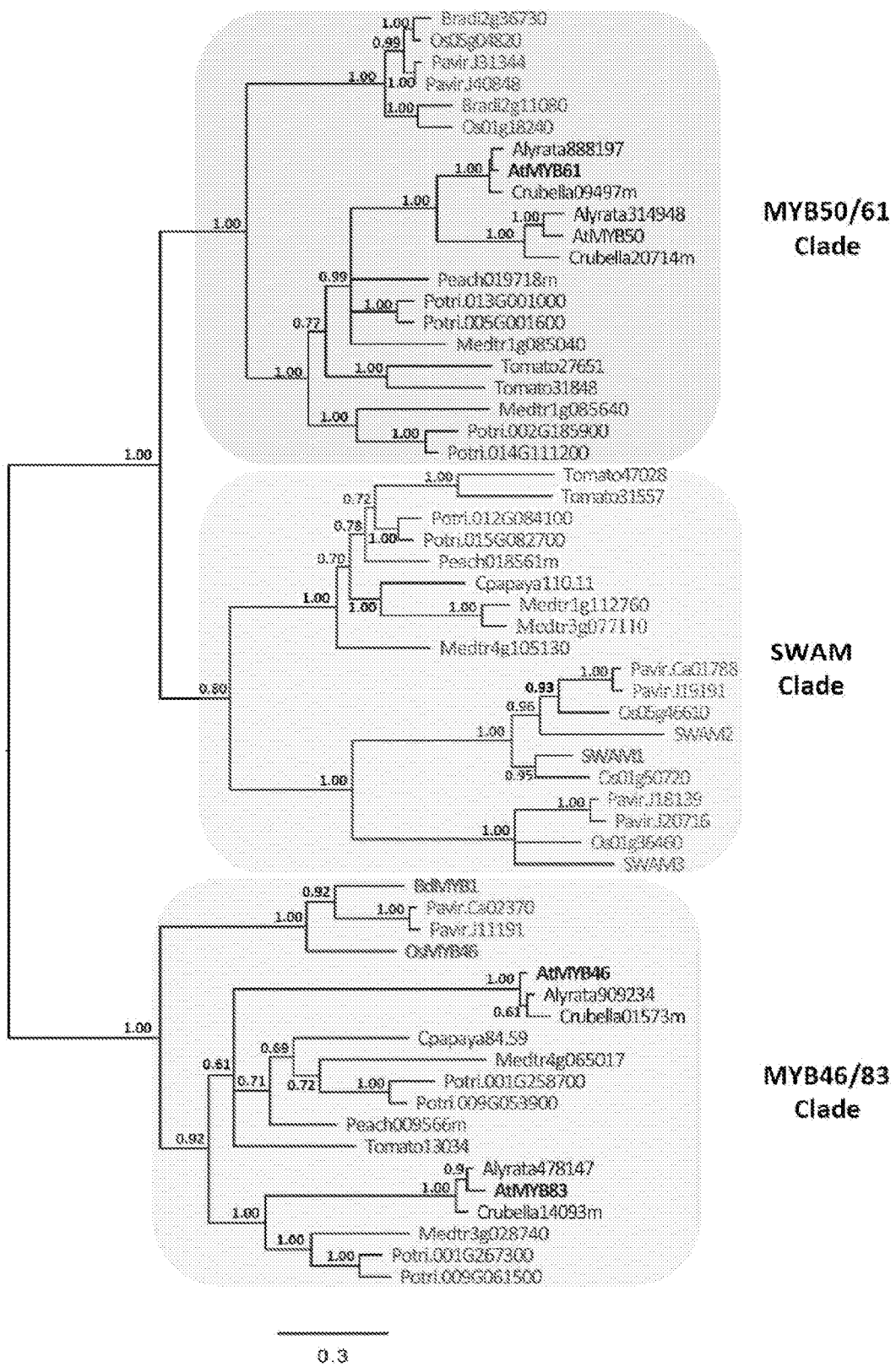

SWAM1 Belongs to a Sub-Clade without Representation from the Brassicaceae Family MYB proteins are involved in a variety of processes during growth and development including cell wall thickening, cell cycle, and defense. Many of the *A. thaliana* MYB proteins such as AtMYB46 and AtMYB83 directly regulate cell wall thickening. To determine the protein similarity between SWAM1 and functionally characterized MYBs, a phylogeny was reconstructed using MYB protein sequences from *A. thaliana*, *B. distachyon* and rice (data not shown). While the previously described OsMYB46 and BdMYB1 (Zhong et al., 2011; Valdivia et al., 2013) are orthologs of the well-characterized *A. thaliana* MYBs, AtMYB46 and AtMYB83, no *A. thaliana* protein was part of the SWAM1 clade that also includes Bradi2g17982 (SWAM2) and Bradi2g40620 (SWAM3). To evaluate if SWAM1 is indeed specific to grasses, the grass *Panicum virgatum*, the asterid *Solanum tuberosum*, and six more rosids were added to the phylogenetic analysis including two more members of the Brasicaceae family: *A. lyrata* and *Capsella rubella* (FIG. 1C). An outgroup of the phylogenetically distinct AtMYB46 and AtMYB83 clade was also included. While *A. thaliana* AtMYB50 and AtMYB61 proteins are the most similar to SWAM1/2/3, there is an additional clade more phylogenetically similar that includes proteins from the other eudicot species. However, this relationship between the eudicot and grass SWAM clades is not well resolved due to the relatively low likelihood. score support in the Bayesian tree. The dicot SWAM sequences are sister to the AtMYB50 and AtMYB61 clade in a Maximum-likelihood tree with 1000 bootstraps, but with week support (54%). However, based on the protein sequence alignment in MUSCLE, the eudicot SWAMs show higher similarity to the grass SWAMs than sequences included in the AtMYB50 and AtMYB61 clade. No protein from the represented species from the Bracicaceae family is part of the SWAM1 sub-clade. To further confirm that the SWAM1 gene lineage is missing from the Brassicaceae the local genome synteny was compared between *A. thaliana* and *Carica papaya*, and a more distantly related rosid, *Populus trichocarpa*. Using the SWAM1 clade genes, a region syntenic among *C. papaya* and *P. trichocarpa* was identified. The regions flanking the SWAM1 orthologs were used to identify a syntenic region in *A. thaliana*. There is clear micro-synteny with no rearrangements between several consecutive (FIG. 8). While the SWAM1 clade representative from each one of these species lies within this syntenic region, it is conspicuously absent in *A. thaliana*. The analysis of phylogeny and synteny strongly suggest that the SWAM clade was present in the last common ancestor between eudicots and grasses, but was lost in the Brassicaceae during evolution.

Figure 2A:
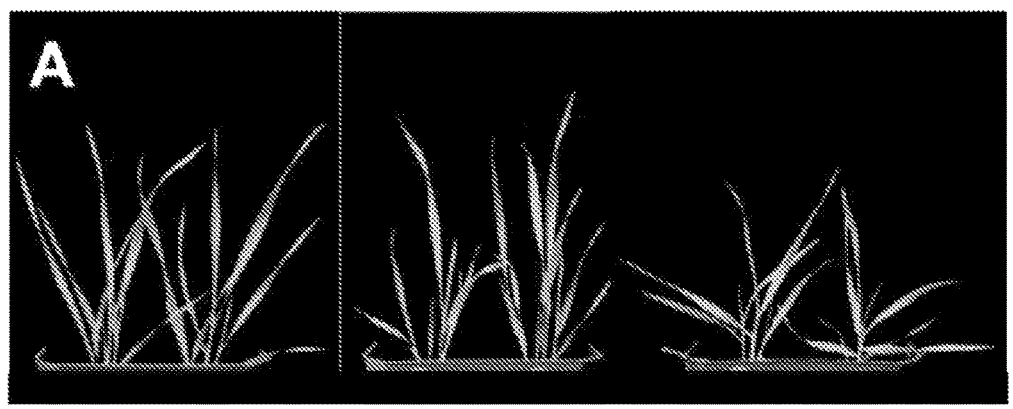
FIGS. 2A-F. SWAM1 is an activator of plant above ground biomass accumulation. Vector control (left), SWAM1-OE (center), and SWAM1-DR (right) plants were planted at the same time. All three lines appeared similar two weeks following germination (A). When completely senesced, SWAM1-DR lines remained dwarf (B). Number of days before the first inflorescence was visible (C). Total above ground biomass (D), plant height (E), and stem cross section area of the first internode (F) at complete senescence. Twelve to sixteen individuals from three independent events were analyzed for each trait. *p<0.05.
Figure 2B:
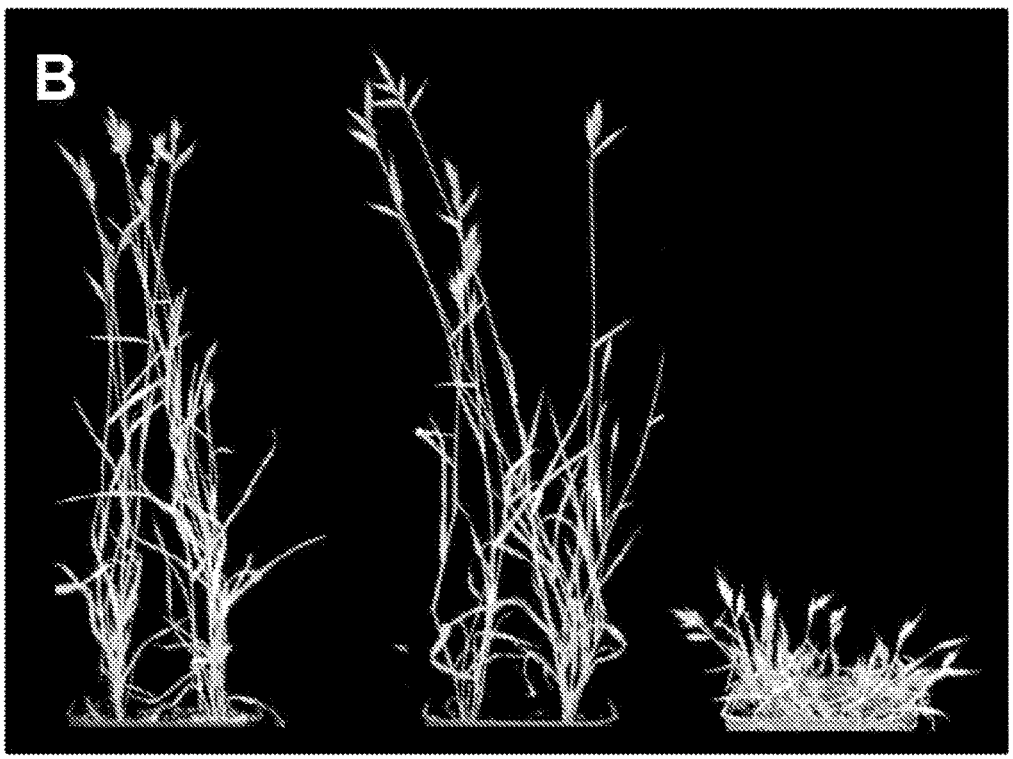
Figure 2C:
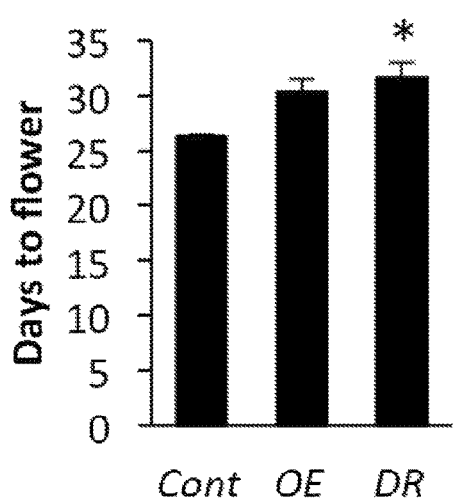
Figure 2D:
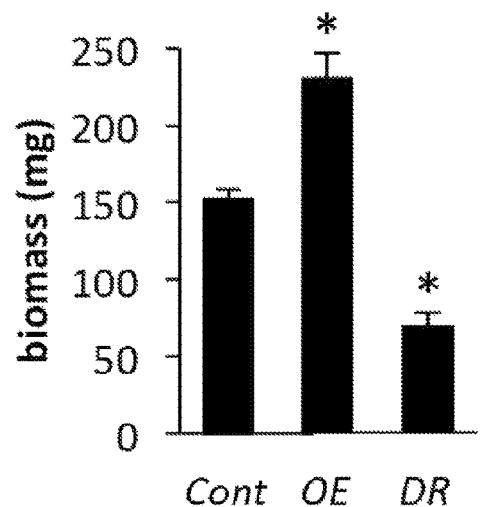
Figure 2E:
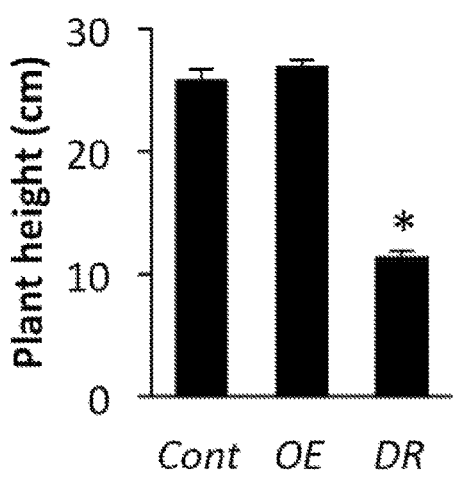
Figure 2F:
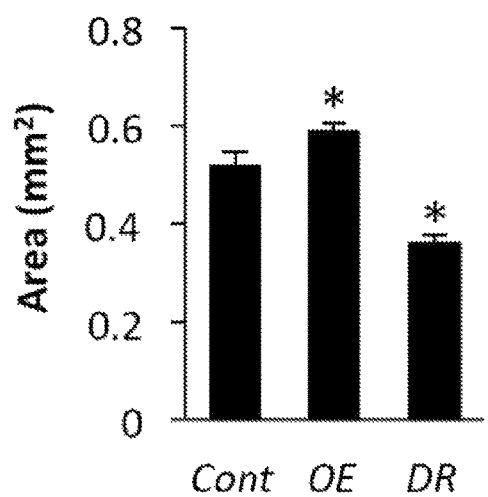
Figure 3A:
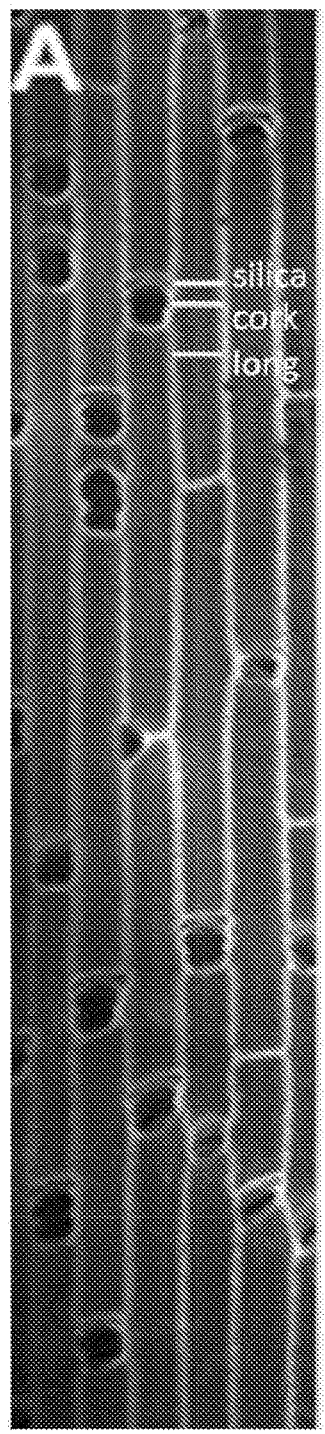
FIGS. 3A-E. SWAM1-DR plants are dwarf due to non-elongated stem cells. Longitudinal stem sections illustrating the cell length of control (A), SWAM1-OE (B), and SWAM1-DR (C). Confocal images of propidium iodide stained longitudinal stem sections of the first internode of flowering stems. Scale bar=50 μm. Stem internode epidermal cell count (D), and Stem epidermal cell length (E) of the first internode of flowering stems.
Figure 3B:
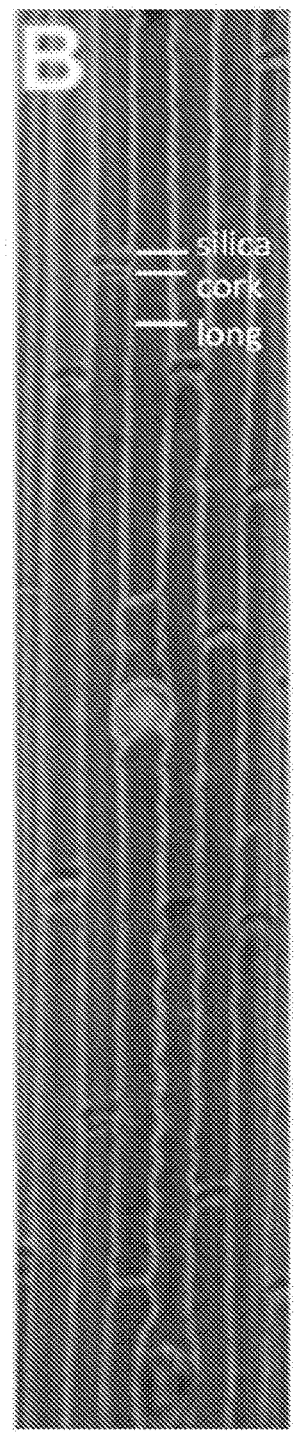
Figure 3C:
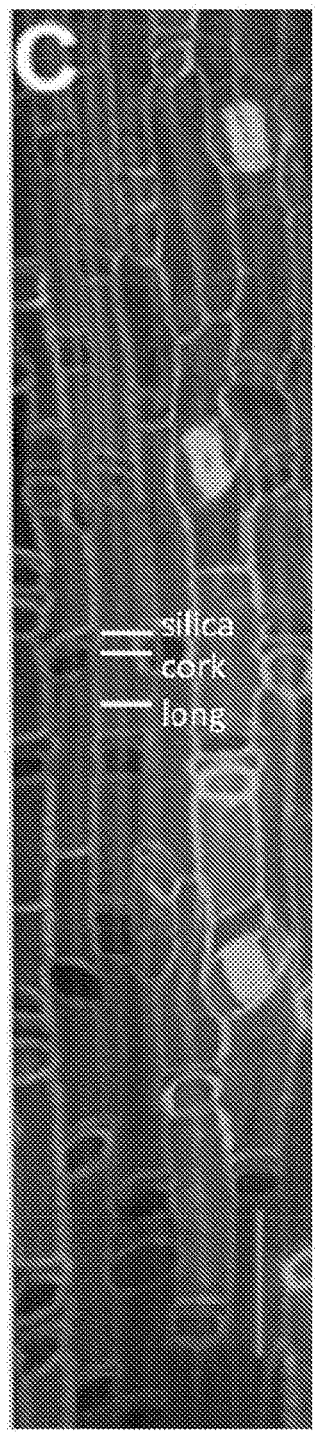
Figure 3D:
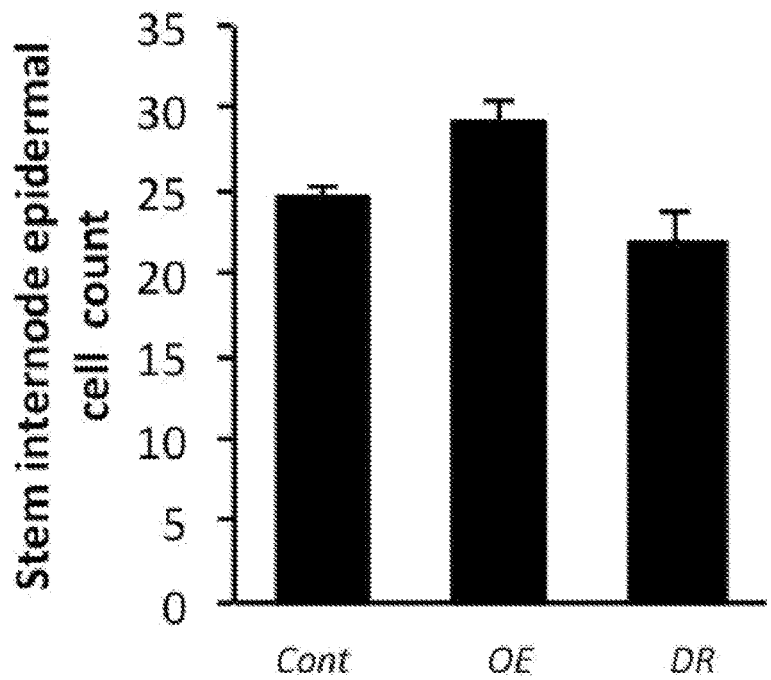
Figure 3E:
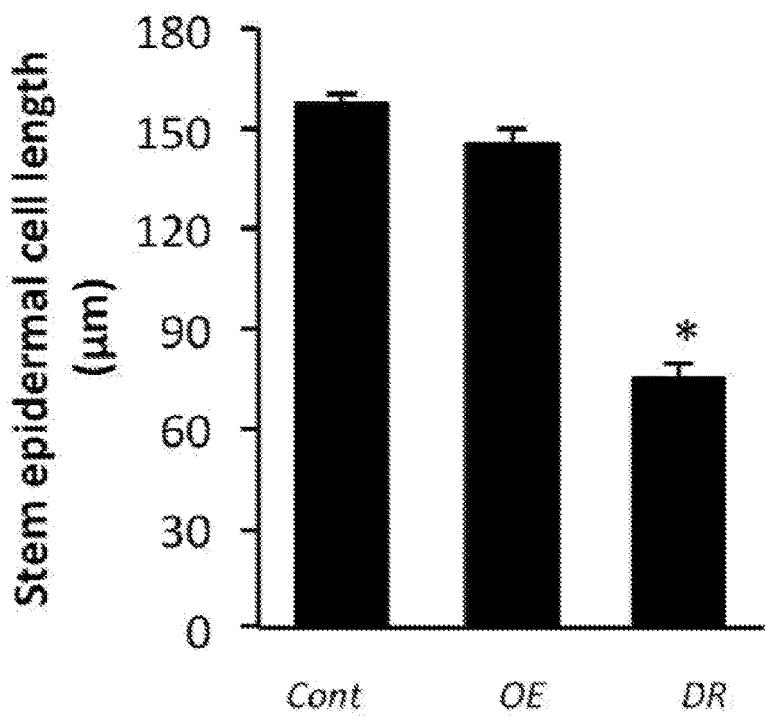

Gain-of-Function and Dominant Repression of SWAM1 Results in Reciprocal Whole Plant Phenotypes To investigate the function of SWAM1, gain-of-function lines were developed by over-expressing the full-length coding region under the maize ubiquitin promoter; SWAM1-OE. Similarly, dominant repressor lines were generated by over-expressing the full-length coding region fused to a 39-base pair dominant repressor sequence; SWAM1-DR. Multiple independent events were generated and tested for each transgene. In general, the SWAM1 gain-of-function and dominant repressor plants exhibited reciprocal phenotypes. Two weeks after germination, both lines had similar stature, but phenotypically diverged when stem internodes began to elongate (FIG. 2A). When the inflorescence emerged from the flag leaf, SWAM1-OE lines were slightly taller than the control lines and the dominant repressor lines were significantly shorter. These phenotypes persisted throughout development until plants completely senesced (FIG. 2B). Inflorescence emergence was significantly delayed by about 5 days in both lines compared to the controls (FIG. 2C). Moreover, they differed significantly in above ground biomass. At complete senescence, above ground biomass yield was significantly greater for SWAM1-OE plants and reduced for SWAM1-DR plants (FIG. 2D). While there was no significant difference in plant height between control and SWAM1-OE lines, SWAM1-DR lines were dramatically shorter (FIG. 2E). Leaf, stem node, and internode count were unchanged; however, the internodes were not fully elongated in SWAM1-DR plants. Possible explanations for a short internode include fewer cells, shorter cells, or both. To test these possibilities propidium iodide treated longitudinal sections of the first internode was examined using confocal microscopy (FIG. 3A-C). An equivalent number of long cells was observed among the three lines (FIG. 3D), but the SWAM1-DR long cells were not as elongated (FIG. 3E). In addition, the transverse stem cross section area differed among the three lines at senescence. Relative to control, SWAM1-OE plants had a larger transverse stem area and SWAM1-DR plants had a significantly smaller area (FIG. 2F). This observation may account for some of the differences observed in above ground biomass.

Figure 4A:
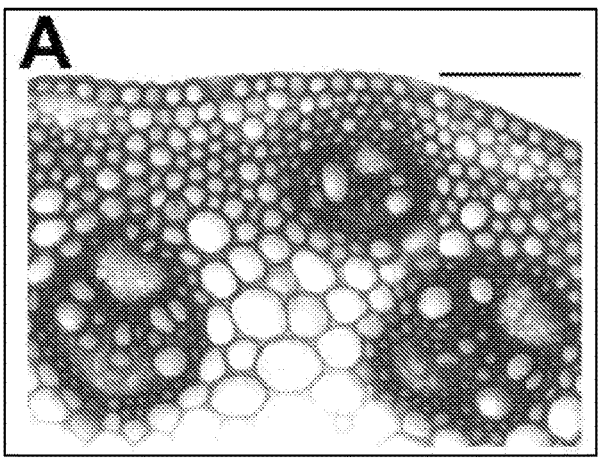
FIGS. 4A-E. SWAM1 is an activator of stem lignin accumulation. First internodes of fully senesced plants were hand sectioned and stained with phloroglucinol-HCl and representative images are illustrated (A-C). Compared to the control (A) SWAM1-OE stem sections (B) stained a dark orange red color and SWAM1-DR stem sections (C) were stained yellow in the interfascicular region and a less intense red color in the vascular bindles. Scale bar=0.1 mm. Acetyl bromide soluble lignin content (D) and Ethanol yield (E) of completely senesced stem tissue. Pulverized stem tissue from six to sixteen individuals from three independent events were analyzed for each line. *p<0.05.
Figure 4B:
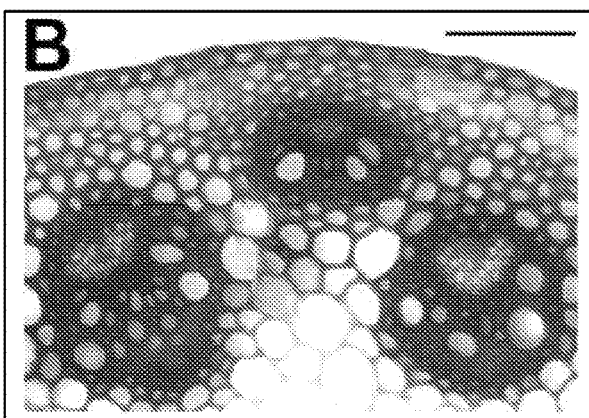
Figure 4C:
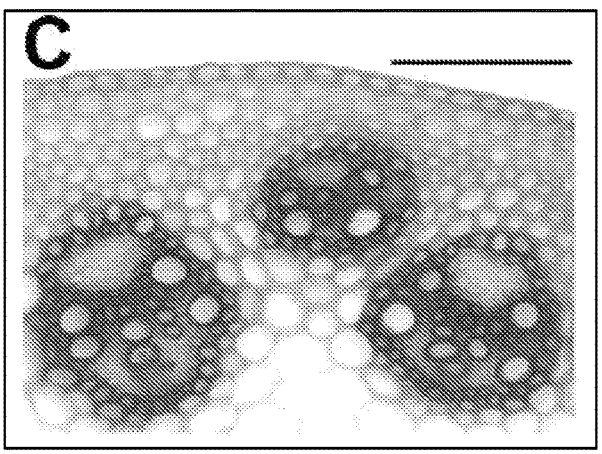
Figure 4D:
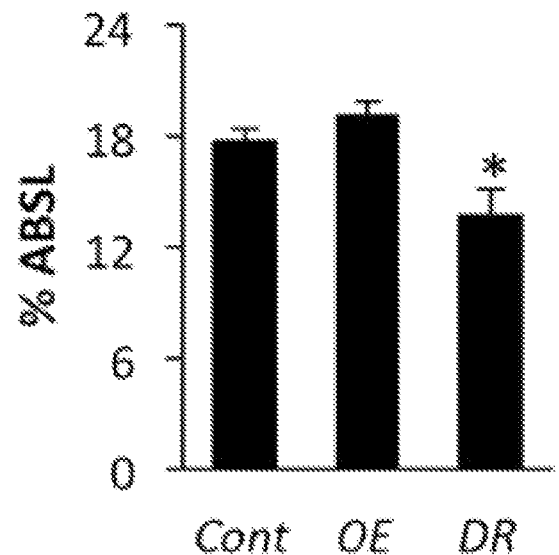
Figure 4E:
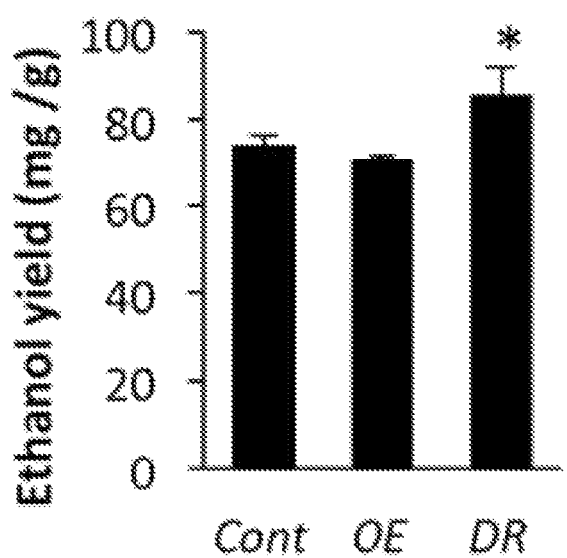

SWAM1 Regulates Secondary Cell Wall Lignification and Biofuel Conversion Efficiency To further investigate the function of SWAM1, stem cross sections were analyzed using bright field light microscopy for changes in vascular patterning and composition. Vascular bundle shape and arrangement appeared similar in all three transgenic lines; however, a striking difference was observed in the cells between the vascular bundles when stained with a lignin-indicator dye, phloroglucinol-HCl (FIG. 4A-C). The interfascicular fiber regions of SWAM1-OE sections were bright red and the SWAM1-DR sections were yellow relative to the control sections indicating the presence of very little lignin. However, the color intensity of the vascular bundles was similar among the three transgenic lines. The striking change in histochemical staining led to the investigation of the lignin content in these lines. Fully senesced pulverized stem tissue was assayed for acetyl bromide soluble lignin content. There was a slight increase in lignin content in SWAM1-OE stems and a significant decrease in SWAM1-DR stems (FIG. 4D). Considering lignin content is generally inversely correlated with bioconversion efficiency phenotypes, ethanol yield was measured after culturing senesced stems with *Clostridium phytofermentans*. As expected, a decrease in ethanol yield was observed for SWAM1-OE lines and conversely a significant increase for SWAM1-DR lines (FIG. 4E).

SWAM1 is an Activator of Secondary Cell Wall Biosynthesis and a Regulator of Cell Wall Thickening The interfascicular fiber walls were examined in greater detail using transmission electron microscopy due to the striking changes observed in lignin staining and overall stem area. The first internode of the tallest stem when the inflorescence had just emerged from the flag leaf was fixed and sectioned using an ultra-cut microtome (FIG. 5). In comparison to the cell wall thickness of the control samples, SWAM1-OE walls were thicker and SWAM1-DR walls noticeably thinner. These results suggest that changes in secondary wall thickness may account for the overall differences observed in stem area and the above ground biomass (FIG. 5D-F). Based on these results it is evident that SWAM1 plays an important role in activating secondary wall thickening.

SWAM1 Regulates Cellulose and Lignin Associated Gene Expression

To investigate the transcriptional function of SWAM1, gene expression was measured in SWAM1 transgenic mutants. The tallest stem from developmentally equivalent plants was collected and flash frozen when the inflorescence was just visible from the flag leaf. Quantitative real time PCR (QRT-PCR) was utilized to examine transcript abundance of the transgenes and cell wall genes. Presence of the SWAM1-OE transgene resulted in a slight increase in the abundance of the SWAM1 transcript and the SWAM1-DR transgene resulted in a significant increase in the total SWAM1 transcript (FIG. 6A). Three cellulose genes, two lignin genes and one hemicellulose gene was analyzed using QRT-PCR. Among the three CELLULOSE SYNTHASE A genes, BdCESA4 and BdCESA7 were significantly up regulated in SWAM1-OE plants. All three CESA genes were significantly down regulated in SWAM1-DR plants (FIG. 6B). A similar expression pattern was observed for the lignin gene, BdCOMT4, a significant up regulation in SWAM1-OE plants and a significant down regulation in SWAM1-DR plants. The second lignin gene BdCAD1 exhibited no significant change in the transcript level in SWAM1-OE plants however it was significantly down regulated in SWAM1-DR plants (FIG. 6B). The transcript levels of the hemicellulose gene BdGT47D3 was moderately increased in the SWAM1-OE plants and significantly decreased in SWAM1-DR plants. As demonstrated above, SWAM1 influences the expression of cellulose, hemicellulose and lignin gene expression. Changes in BdCESA4/7/8, BdGT47D3, BdCOMT4 and BdCAD1 transcript levels along with the changes observed in cell wall thickness and composition implies SWAM1 activates the transcription of secondary cell wall biosynthetic genes. It is reasonable to predict there will be transcriptional changes associated with other cell wall genes that are functional in a similar capacity in cellulose and lignin biosynthesis. The cis-regulatory regions of BdCESA4/7/8, BdCOMT4 and BdCAD1 were searched for known regulatory elements. A sequence similar to the AC-11 element (Hatton et al., 1995)(ACCAAC) is upstream of the lignin genes BdCAD1 and BdCOMT4 and the cellulose genes BdCESA4/7/8 (FIG. 9). A heterologous system was used to test for an affinity between this common motif and SWAM1 protein. Four adjacent copies of the identified AC-II were fused to the GAL4 activation domain and stably integrated into the yeast genome. A similar strain was developed using a mutated motif (TTTAAC) as a negative control. SWAM1 preferentially bound the promoter containing the AC-II element, but not the mutated version (FIG. 6C).

SWAM1 Directly Interacts with Secondary Cell Wall Biosynthetic Genes In Vivo

Altogether these results support the notion that SWAM1 directly activates cellulose and lignin gene expression by direct interaction with their cis-regulatory regions. To investigate these interactions in vivo, transgenic lines were generated with a GFP-tagged SWAM1 (SWAM1-GFP-OE). These lines were used for chromatin immunoprecipitation along with control plants (GU-OE). Immunoprecipitated chromatin was used as template for QRT-PCR to assay for enrichment of specific cell wall gene cis-regulatory regions. The results revealed a SWAM1 specific enrichment of BdCESA4, BdCESA8, BdCAD1 and BdCOMT4 promoter fragments (FIG. 6D). Moreover, all the enriched fragments contain an AC-like element (FIG. 9). This provides evidence for direct binding of SWAM1 to cell wall gene promoters.

Discussion

A co-transcriptional analysis coupled with protein phylogenies with a focus on MYB transcription factors was used and resulted in the identification of SWAM1 as a potential candidate regulator of cell wall thickening. The SWAM1 transcript was abundant in stem, mirroring the expression profile of characterized *A. thaliana* cell wall regulators involved in promoting secondary cell wall biosynthesis (Ko et al., 2004; Brown et al., 2005; Kubo et al., 2005; Persson et al., 2005). The SWAM1 transcript was mainly localized in the interfascicular fibers, xylem and somewhat to the epidermis. The SWAM1 protein shares some homology to AtMYB46 and AtMYB83, which are mainly expressed in xylem fibers (Zhong et al., 2007; McCarthy et al., 2009), but BdMYB1 is the closest ortholog (Valdivia et al., 2013). All of the characterized cell wall related *A. thaliana* MYB proteins are localized to the xylem and fibers and none have been reported with interfascicular fiber specific localization. Interestingly, SWAM1 has a strong localization pattern in the interfascicular fiber cells. The difference observed in tissue specific localization between SWAM1 and AtMYB46 and AtMYB83 could be attributed to the phylogenetic separation or species-specific differences. Indeed, SWAM1 is part of a phylogenetic clade that includes grasses and eudicots, but not the Brassicaceae, namely *A. thaliana, A. lyrata,* and *C. rubella*. As was observed in *B. distachyon*, the poplar and potato SWAM1 clade genes are most highly expressed in the available gene expression dataset for potato and poplar (Winter et al., 2007), which suggests these genes may have a conserved function.

SWAM1 over-expression and dominant repression transgenes were used for in planta functional characterization. The timing of inflorescence emergence was the only trait that exhibited a similar and significant effect. The whole plant phenotypes were dramatically different; SWAM1-OE resulted in a larger plant with greater biomass. This has not been reported for the over-expression of AtMYB46/83/58 or 63 (Zhong et al., 2007; Ko et al., 2009; McCarthy et al., 2009; Zhou et al., 2009). The increase in above ground biomass appears to be in part the product of larger stems with thicker secondary cell walls. Thicker secondary cell walls were also observed in AtMYB46 and AtMYB83 over-expression lines (Zhong et al., 2007; McCarthy et al., 2009). Conversely, SWAM1-DR resulted in severely dwarf plants with significantly diminished above ground biomass. Dwarfism in SWAM1-DR plants was mainly attributed to the internode cell length, but not the cell count. SWAM1-DR stem cells were significantly shorter compared to the control stem cells resulting in a significantly dwarfed plant. These plants also had significantly smaller stems with thinner interfascicular fiber cell walls. AtMYB46 and AtMYB83 dominant repressors were also shown to have significantly thinner secondary cell walls in vessels and fibers resulting in a pendent phenotype (Zhong et al., 2007; McCarthy et al., 2009). However unlike SWAM1, dominant repression of AtMYB46 and AtMYB83 did not cause dwarfism. The difference seen between SWAM1 and AtMYB46 and AtMYB83 plant height phenotypes under dominant repression could be the result of a functional difference between these MYB proteins.

Another striking observation was the differences in lignification in stem cross sections. Senesced plants were used for histochemical analysis and lignin composition analysis. Over-expression of SWAM1 resulted in a moderate increase in the lignin content in whole stems and dominant repression resulted in a significant decrease. Based on phloroglucinol-HCl staining it is evident that SWAM1 has a profound impact on the interfascicular fiber cell wall lignification. SWAM1 transcripts were also localized to the same cell types in stem cross sections mainly to the interfascicular fibers and somewhat to the xylem and epidermis. Transcript localization and histochemical analysis of stems further supports an important role for SWAM1 in interfascicular fiber cell wall regulation. Reciprocal lignification patterns have been observed in histochemical studies performed on AtMYB46/83 transverse stem cross sections, where over expression of the genes resulted in ectopic lignification in parenchyma cells and dominant repression results in the absence of secondary cell wall lignification (Zhong et al., 2007; McCarthy et al., 2009). Even though reciprocal phenotypes for total stem lignin were observed, the prominent effect of SWAM1 dominant repression on interfascicular fiber cells is a unique observation. As expected, over-expression of SWAM1 upregulated secondary cell wall biosynthesis genes. Moreover, dominant repression resulted in a significant down regulation of the same cell wall genes. These findings argue that SWAM1 is an activator of secondary cell wall biosynthesis. Some MYB proteins are known to interact with AC-like elements and either activate or repress the transcription of downstream targets (Lois et al., 1989; Hatton et al., 1995; Raes et al., 2003; Kim et al., 2012; Zhong and Ye, 2012). Next, the promoters of genes involved in secondary cell wall biosynthesis for over represented cis-regulatory elements were investigated. As suspected BdCESA4/7/8, BdCAD1, and BdCOMT4 genes all harbor AC-like elements in their promoter regions. In yeast, SWAM1 preferentially bound the AC rich element relative to a mutated version. Therefore, it is plausible that SWAM1 activates the downstream secondary cell wall genes via a protein-DNA interaction facilitated through AC elements found in their promoter regions. This was further supported by the enrichment of cell wall gene promoters such as BdCESA4, BdCESA8 and BdCOMT4 in SWAM1 immunoprecipitated chromatin. This provides in planta evidence for a direct interaction between SWAM1 protein and the cell wall gene promoters. AtMYB46 has also been shown to interact with the AtCESA4/7/8 promoters in planta (Kim et al., 2013). Therefore, based on the in silico predictions, synthetic AC element analysis and chromatin immunoprecipitation, it is evident SWAM1 is a direct activator of secondary cell wall biosynthesis in *B. distachyon.*

As might be expected for plants with a significant reduction in total lignin, a moderate reduction in ethanol yield was observed following incubation of pulverized SWAM1-DR stems with *Clostridium phytolermentans*. On the other hand SWAM1-OE resulted in larger plants with greater above ground biomass without increasing recalcitrance making SWAM1 a candidate for energy crop improvement. In conclusion, it was herein demonstrated that SWAM1 is a activator capable of regulating secondary cell wall biosynthesis. This protein has a greater impact on the interfascicular fiber cell walls, which is ideal in manipulating energy crops without causing drastic effects to the vascular system.

Example 2

Grass NAC Repressor of Flowering Suppresses Floral Transition and Secondary Wall Synthesis in *Brachypodium Distachyon*
Introduction The large NAC (NAM, ATAF1/2, and CUC2) transcription factor family is comprised of plant-specific proteins. Several are well characterized with respect to the regulation of secondary cell wall biosynthesis and are thought of as key regulators in this process. SECONDARY WALL ASSOCIATED NAC DOMAIN PROTEIN1 (SND1; also known as NST3) is a fiber specific *Arabidopsis thaliana* secondary cell wall regulator. SND1 is the most extensively characterized among these NAC proteins that activate the expression of cellulose and lignin genes. Over-expression of SND1 results in ectopic deposition of secondary cell walls in parenchymatous cells. Conversely, dominant repression results in a significant reduction in secondary cell wall deposition in fibers (Zhong et al., 2006). NAC SECONDARY WALL THICKENING PROMOTING FACTOR1 and 2 (NST1/2) regulate secondary cell wall deposition in *A. thaliana* anther endothecium (Mitsuda et al., 2005). NST1 and SND1 are thought to play redundant regulatory roles and the double mutant causes a drastic reduction in the expression of secondary cell wall genes and a significant reduction in cellulose, xylan and lignin biosynthesis (Mitsuda et al., 2007; Zhong et al., 2007). VASCULAR RELATED NAC DOMAIN6 and 7 (VND6/7) specifically expressed in protoxylem and metaxylem are required for vessel development in *A. thaliana* roots (Kubo et al., 2005; Demura and Fukuda, 2007). Moreover, over-expression of VND6/7 results in ectopic vessel development and dominant repression results in the loss of protoxylem and metaxylem development (Kubo et al., 2005). Collectively these five NAC proteins are considered master regulators capable of activating the entire secondary cell wall biosynthesis process by interacting and activating downstream transcription factors including SND2, SND3, MYB46, MYB54, MYB42, MYB103, MYB85, MYB52, MYB69 and KNAT7 (Zhong et al., 2007; Zhong et al., 2008).

To date, very little functional characterization has been done for the two wall biosynthesis associated NAC transcription factors SND2 and SND3. These two proteins are distantly related to the previously described proteins when considering DNA-binding and transcriptional activation domain sequences (Hu et al., 2010; Wang et al., 2011). Even though SND1, SND2, and SND3 share the same identifier, SND1 is closely related to NST1 and NST2 and distantly related to SND2 and SND3. In a recent study NAC protein from 19 plant species were analyzed to understand the evolutionary relationship among NST, SND and VND sub groups. In this comparison, SND2 orthologs were found in both dicot and monocot species. However, SND3 was only found within dicot species suggesting it is a dicot specific regulator (Yao et al., 2012). Both SND2 and SND3 are highly expressed in *A. thaliana* stems mirroring a similar expression profile of many characterized cell wall regulators (Yao et al., 2012). Over-expression of SND2 increases the secondary wall thickness in interfascicular and xylary fibers in *A. thaliana* (Zhong et al., 2008). Conversely, dominant repression results in a drastic reduction of secondary wall thickness in fibers. Moreover, SND2 has been shown to regulate cellulose, hemicellulose, and lignin biosynthesis genes (Hussey et al., 2011). SND2 orthologous proteins have also been characterized in poplar. Over-expression of the SND2 ortholog PopNAC154 in poplar reduced plant height; however, unlike in *A. thaliana*, over-expression had no effect on secondary cell wall thickness (Grant et al., 2010). On the other hand, dominant repression of the SND2 ortholog (PtSND2) resulted in a significant reduction of secondary cell wall thickness in xylary fibers (Wang et al., 2013). These diverging results between *A. thaliana* and poplar suggest differing regulatory functions by the various SND2 orthologs in different plant species. This contrasts with SND1, where the rice and maize counterparts were able to complement the snd1/nst1 double mutant and cause similar over-expression phenotypes in *A. thaliana* (Zhong et al., 2011; Yoshida et al., 2013).

Secondary cell walls, by weight, represent the majority of biomass in stem tissue. While grasses can produce abundant stem before flowering, *A. thaliana* grows as a rosette of leaves and only elongates stem following floral induction. The transition from vegetative to reproductive growth is an important phenomenon that is achieved through the integration of developmental and environmental cues such as day length and temperature. The molecular mechanisms of flowering have been well characterized in the model dicot *A. thaliana*. The mobile signal responsible for this transition is florigen, which is encoded by FLOWERING LOCUS T (FT). It moves from leaves to the shoot apical meristem to activate meristem identity genes, including APETALA1 (AP1), CAULIFLOWER (CAL) and FRUITFUL (FUL), to transition the shoot apical meristem into a flower bud (FIG. 10) (Ream et al., 2014). FT is expressed following exposure to cold through epigenetic repression of repressors of flowering: FLOWERING LOCUS C (FLC) and SHORT VEGETATIVE PHASE (SVP) (Michaels and Amasino, 1999; Alexandre and Hennig, 2008; Gu et al., 2010). Long day photoperiod can also induce flowering through CONSTANS induction of FT expression (Imaizumi and Kay, 2006). Once activated, the mobile signal can complex with the bZIP transcription factor FD to form an FT-FD complex in the stem (Jaeger and Wigge, 2007). This complex is responsible for initiating the transcription of meristem identity genes.

Many of these same components have been identified as having a role in the control of flowering in grasses. Similar to *A. thaliana*, FT (also known as VERNALIZATION3 in barley and wheat) is the main floral integrator of developmental and environmental cues and turning on floral meristem identity genes including VRN1 (Greenup et al., 2010; Wu et al., 2013; Lv et al., 2014; Ream et al., 2014). In temperate cereals, FT expression is induced under long days and VRN2 is repressed in response to vernalization (Greenup et al., 2010). VRN1 is the cereal AP1 ortholog, but contrary to *A. thaliana* AP1, VRN1 is expressed in both leaves and in the floral meristem (Trevaskis et al.; Alonso-Peral et al., 2011). VRN1 is activated by low temperatures and as a result represses VRN2 during winter allowing flowering in spring (Greenup et al., 2009). PHOTOPERIOD1-H1 (PPD-H)1 is another component responsible for activating FT under reduced levels of VRN2. Once activated, FT protein binds FLOWERING LOCUS D LIKE2 (FDL2), the FD ortholog found in cereals and initiates VRN1 transcription in the meristem (Li and Dubcovsky, 2008) triggering the transition to flowering (FIG. 11). Regardless of the similarities and distinctions for the signal transduction pathways that govern floral induction between *A. thaliana* and grasses, fundamental differences in how that regulation relates to stem formation are expected. Here we describe the function of a NAC transcription factor, GRASS NAC REPRESSOR OF FLOWERING (GNRF), using over-expression and loss-of-function mutant lines.

Material and Methods

Phylogenetic Analysis

Amino acid sequences of *A. thaliana* NAC proteins SND2 and SND3 and the orthologous proteins from *O. sativa, Z. maize, P. trichocarpa* and *Sorghum biocolor* were downloaded from plant transcription factor data base (P1nTFDB; plntfdb.bio.uni-potsdam.de/v3.0). *B. distachyon* NAC sequences were downloaded from phytozome (phytozome.net/). A neighbor-joining phylogeny was constructed with 1000 bootstrap permutations using MEGA 5.0. An outgroup including *A. thaliana* NST1, NST2 and SND1 were also included in this analysis.

GNRF-OE Plasmid Construction

Full-length coding region of Bradi2g46197 (GNRF) was PCR amplified using Bd21-3 cDNA with the stop codon using Phusion high-fidelity DNA polymerase (New England Bio Labs) and cloned into pENTR/D-TOPO vector (Invitrogen). Sequence-confirmed entry clone was recombined with pOL001 ubigate ori1 destination vector (modified from pOL001, described in (Vogel et al., 2006) to generate the GNRF gain-of-function construct (GNRF-OE). Above construct was transformed into *Agrobacterium tumefaciens* strain AGL1 via electroporation for *B. distachyon* calli transformations.

Plant Material, Growth Conditions and Calli Transformation

*Brachypodium distachyon* (L.) line Bd21-3 was used as the genetic background. Seeds were imbibed a week and planted as previously described by Handakumbura et al., 2013. *Brachypodium distachyon* calli transformation was carried out as described by (Vogel and Hill, 2008) with minor modifications described in Handakumbura et al., 2013. Once shoots and roots were established primary transgenics were transplanted to soil. Primary transgenic were PCR confirmed by the amplification of the hygromycin resistance gene and were propagated for two subsequent generations to obtain T3 individuals.

gnrf-1 Mutant Allele Isolation

A homozygous gnrf-1 mutant allele was isolated from the TILLING (Targeting Induced Local Lesions in Genomes) mutant population generated at INRA-Versailles by restriction enzyme digestions. Leaf genomic DNA was isolated from each individual using the method described by Handakumbura et al., 2013. A 614 bp fragment spanning the region with the mutations was PCR amplified using Taq DNA polymerase and the purified amplicons were digested with BaeGI at 37° C. The digestion results in two fragments of 141 bp and 473 bp for the wild-type allele and a single undigested fragment for the mutant allele.

Genotyping and Phenotyping

Genomic DNA was extracted from T3 generation GNRF-OE plants and M2 generation gnrf-1 plants as previously described (Handakumbura et al., 2013). GNRF-OE plants were PCR confirmed for the hygromycin selectable marker gene and were used in subsequent experiments. Flowering was induced in about five percent of the GNRF-OE plants with excessive fertilizer treatment with a N-P-K 10:30:20 fertilizer. Homozygous gnrf-1 mutants were confirmed by restriction enzyme digestion as described previously. Phenotypic data such as flowering time, plant height, above ground biomass at senescence were manually recorded.

RNA Extraction and QRT-PCR

Total RNA was extracted from the first, second, and third internodes of the tallest stem at BBCH stage 5 and from the fourth leaf from the base of the tallest stem at BBCH stage 4.5 (Hong et al.) (Plant RNaeasy, Qiagen, Valencia, Calif.) as previously described by Handakumbura et al., 2013. First strand cDNA was synthesized from 1 μg of DNase (Qiagen) treated total RNA using Superscript III reverse transcriptase with oligo dT primers (Invitrogen, Grand Island, N.Y.). Triplicate quantitative PCR reactions were performed as described in Chapter 3. BdUBC18 (ubiquitin-conjugating enzyme 18) and GapDH were used as reference genes for normalization (Hong et al., 2008). QuantiPrime primer design tool was used for qPCR primer design (Arvidsson et al., 2008).

Microarray Analysis

For the microarray analysis, three stem samples at BBCH stage 5 (Hong et al., 2011) were pooled for each biological replicate and hybridized in triplicate for each line. RNA was extracted using a kit (Plant RNaeasy, Qiagen, Valencia, Calif.) as described above. Samples were hybridized to a *B. distachyon* BradiAR1b520742 whole genome tiling array (Affymetrix, Santa Clara, Calif.). Based on the hybridization signals a significantly differentially expressed gene list was generated using a modified t-test (Tusher et al., 2001).

Histo-Chemical Analysis of Stem Lignification

Histo-chemical assays were performed on the first internode of tallest stem at complete maturity. Hand cut sections were stained with phloroglucinol-HCl as described in Chapter 3 for total lignin. Stained sections were observed under an Eclipse E200MV R microscope (Nikon) and imaged using a PixeLINK 3 MP camera.

Acetyl Bromide Soluble Lignin Measurement

Fully senesced pulverized stem tissue was used for acetyl bromide soluble lignin (ABSL) measurements as previously described (Foster et al., 2010) and briefly specified in Chapter 3. Three to six individuals were analyzed in triplicate for each line.

Results

Bradi2g46197 Transcript is Abundant in Stem Tissue

The secondary cell wall regulators characterized to date exhibit the signature expression profile of being highly expressed in tissues abundant in secondary cell walls relative to other tissues. To investigate Bradi2g46197 transcript abundance in leaf, stem, and root, a *B. distachyon* microarray data set was utilized (Handakumbura et al., 2013). Bradi2g46197 transcript abundance was approximately nine and three-fold greater in stem, relative to leaf and root, respectively (FIG. 12A). Grass stems are substantially enriched for secondary cell walls (Matos et al., 2013). Therefore, based on annotation and expression analysis, Bradi2g46197 is a potential candidate regulator of grass secondary cell wall biosynthesis.

Bradi2g46197 is the Closest Ortholog to SND2

Bradi2g46197 belongs to the plant specific NAC transcription factor family that is involved in a variety of processes. Some of the *A. thaliana* NAC proteins such as NST1/2, SND1/2/3 are specifically involved in the regulation of cell wall biosynthesis. To determine the protein similarity between Bradi2g46197 and the functionally characterized NACs, a phylogeny was constructed between the NAC protein sequences from *A. thaliana*, *B. distachyon*, *O. sativa*, *Z. maize*, *P. trichocarpa* and *Sorghum bicolor* using the MEGA 5.0 software. NST1, NST2 and SND1 were used as an out-group in order to better understand the relationship of Bradi2g46197 to the other dicot and monocot NAC orthologs (FIG. 12B). Based on protein similarity, Bradi2g46197 is a grass ortholog to both SND2 and SND3. Both dicots included in this analysis, *A. thaliana* and poplar, have two orthologous proteins in this clade while the grasses have only one.

Over-Expression of Bradi2g46197 Results in Persistent Vegetative Growth

To investigate the function of Bradi2g46197, gain-of-function lines were developed by over-expressing the full-length coding region under the maize Ubiqutin promoter. Multiple independent events were generated for this construct and at least three events were used in the subsequent experiments. A homozygous line with a nonsynonymous point mutation that modifies the fiftieth amino acid from a proline (P) to a leucine (L) was isolated from a TILLING (Targeting Induced Local Lesions in Genomes, (Dalmais et al., 2013) population to investigate the loss-of-function phenotypes. The aforementioned point mutation lies within the DNA binding domain in the N-terminus and predicted to alter protein function. Surprisingly, over-expression construct harboring transgenics remained vegetative until senescence (FIG. 13). These plants exhibited a branched and bushy phenotype and did not transition from vegetative to reproductive growth. We therefore named the Bradi2g46197 locus GRASS NAC REPRESSOR OF FLOWERING (GNRF). From here on, the gain-of-function mutant will be referred to as GNRF-OE and the loss-of-function mutant gnrf-1. Unlike GNRF-OE plants, which did not flower and were considerably shorter than control plants, gnrf-1 plants flowered significantly earlier than the control plants by approximately 1.5 d (FIG. 14A) and were similar to control plants in stature (FIG. 14B). Moreover, the above ground biomass was significantly greater for GNRF-OE plants whereas no significant difference was observed between gnrf-1 plants and the controls (FIG. 14C).

GNRF is a Repressor of Genes Associated with Cell Wall, Transport, and Flowering Considering the dramatic pleiotropic effects of the gain-of-function lines, a microarray experiment was performed using RNA from pooled stems from control, GNRF-OE and gnrf-1 plants in order to isolate the potential effected pathways. Samples were hybridized to the *B. distachyon* BradiAR1b520742 whole genome tiling arrays and differentially expressed genes were identified using a modified t-test. No significant differences in gene expression were detected between control and gnrf-1. Some rather dramatic changes were observed within the GNRF-OE plants. While only 23 genes were up-regulated by GNRF over-expression, 372 genes were significantly down-regulated. One of the largest categories of repressed genes was transporters of numerous substrates: amino acids, ammonium, arsenite, carboxylate, lipids, peptides, potassium, silicon, sucrose, and sulfate (Table 4.1). Polysaccharide synthesis genes, lignin and lignin related genes, and lipid transfer genes were also abundant among the repressed genes. The most striking observation was the >50 fold repression of two floral meristem identity associated genes VRN1/FUL1/MADS33 (Bradi1g08340) and FUL2/MADS10 (Bradi1g59250). These two genes are the two closest orthologs to *A. thaliana* AP1 and FUL. Apart from the above two genes, several other MADS-box, bHLH, WRKY, HB, NAC and MYB transcription factors were repressed in GNRF-OE stems. Another interesting observation is the 3-fold reduction of BdMYB48 (Bradi2g47590). As previously described (Chapter 3) BdMYB48 is a direct activator of secondary cell wall biosynthesis genes. The repression of the cellulose genes CESA4, CESA7, and COMT4, 4CL1, 4CL3, CCoAMT lignin genes in the GNRF-OE stems could be an indirect effect due to the repression of BdMYB48. As a result of the repression of many cellulose and hemicellulose synthesis genes, GNRF-OE stems should show a significant reduction in the polysaccharide composition. Apart from lignin genes, many laccasses and peroxidases were also repressed in these mutants. These genes are necessary for the polymerization of lignin monomers and their subsequent polymerization within the cell wall (Boerjan et al., 2003). Moreover, several copper ion transporter genes were repressed. Copper ions act as a catalyst in the lignin polymerization process (Boerjan et al., 2003). Down regulation of many lignin and lignin associated genes along with the necessary catalysts should result in a significant reduction in cell wall lignification in GNRF-OE mutants.

TABLE 4.1

Genes repressed by GNRF in GNRF-OE stems

| Gene name | Gene description | Fold change |
|---|---|---|
| Transcription factors | | |
| Bradi1g08340 | MADS33/VRN1/FUL1 | 53.8 |
| Bradi1g59250 | MADS10/FUL2 | 51.3 |
| Bradi1g08326 | MADS1 | 33.6 |
| Bradi2g00280 | WRKY47 | 7.7 |
| Bradi3g26690 | BEL-like Homeobox | 7.0 |
| Bradi1g48520 | MADS7 | 6.1 |
| Bradi1g69890 | MADS11 | 5.7 |
| Bradi1g26720 | SBP family | 4.6 |
| Bradi1g57607 | KNOX6 Homeobox | 4.5 |
| Bradi3g56290 | bZip family | 4.7 |
| Bradi5g10640 | NAC family, XND1-like | 3.6 |
| Bradi1g63690 | MYB-like family | 3.7 |
| Bradi1g51960 | MYB15 | 4.5 |
| Bradi2g48690 | MADS19 | 4.3 |
| Bradi3g21480 | Homeobox family | 3.8 |
| Bradi4g27720 | bZIP70 | 4.4 |
| Bradi3g34567 | WRKY13 | 2.5 |
| Bradi2g05700 | NAC28 | 2.9 |
| Bradi2g47590 | MYB48/SWAM1 | 3.0 |
| Bradi3g51800 | MADS28 | 2.8 |
| Bradi5g11270 | MADS36 | 2.7 |
| Bradi1g12690 | KNOX4 Homeobox | 3.0 |
| Bradi1g10047 | KNOX2 Homeobox | 3.2 |
| Bradi2g09720 | C2C2-Dof family | 3.4 |
| Bradi1g73710 | C2C2-Dof family | 2.6 |
| Bradi1g12780 | bHLH family | 3.4 |
| Bradi1g71990 | bHLH family | 3.2 |
| Bradi3g15440 | bHLH family | 2.7 |
| Bradi3g16515 | MYB59/LHY | 2.9 |
| Bradi3g03407 | ARF family | 3.1 |
| Bradi4g33370 | WRKY60 | 2.2 |
| Bradi2g59110 | SBP family | 2.3 |
| Bradi5g22920 | bHLH family | 2.2 |
| Bradi2g23530 | BEL-like Homeobox | 2.3 |
| Bradi5g17640 | AP2 family | 2.2 |
| Cell wall polysaccharide synthesis | | |
| Bradi2g60557 | Glycosylhydrolase, GH17, β-1,3-glucanase 1 | 12.4 |
| Bradi2g34650 | Fasciclin-like arabinogalactan protein | 8.1 |
| Bradi1g64560 | Glycosyltransferase, GT34 family, xylosyltransferase | 7.6 |
| Bradi2g08310 | Glycosyltransferase, GT1 family, UDP-glucosyl transferase | 7.1 |
| Bradi1g12290 | Glycosyltransferase, GT47 family | 6.8 |
| Bradi4g13697 | Glycosyltransferase, GT37 family fucosyltransferase 1 | 6.2 |
| Bradi2g61230 | Glycosyltransferase, GT61 family | 5.5 |
| Bradi1g25117 | Cellulose synthase-like F | 3.8 |
| Bradi1g33827 | Glycosylhydrolase, GH6, xyloglucan endotransglycosylase 6 | 4.9 |
| Bradi1g21990 | Glycosyltransferase, GT75 family | 4.8 |
| Bradi1g12710 | Glycosyl hydrolase, GH10 family | 4.8 |
| Bradi2g00220 | Fasciclin-like arabinoogalactan protein | 4.6 |
| Bradi1g22030 | COBRA | 4.5 |
| Bradi3g04080 | Glycosylhydrolase, GH9 family glycosyl hydrolase 9B8 | 4.0 |
| Bradi5g04120 | Glycoside hydrolase, α-Expansin | 3.9 |
| Bradi2g53580 | Glycoside hydrolase, α-Expansin | 3.8 |
| Bradi4g33490 | Fasciclin-like arabinoogalactan protein | 3.8 |
| Bradi4g29640 | Glycosylhydrolase, GH9 family | 3.8 |
| Bradi4g21240 | Pfam: 04669 Polysaccharide biosynthesis | 3.7 |

TABLE 4.1-continued

Genes repressed by GNRF in GNRF-OE stems

| Gene name | Gene description | Fold change |
|---|---|---|
| Bradi2g02320 | Glycosylhydrolase, GH10 family | 3.7 |
| Bradi2g59410 | Glycosyltransferase, GT47 family | 3.6 |
| Bradi1g59880 | COBRA-like | 3.6 |
| Bradi3g33130 | Glycoside hydrolase, β-Expansin | 3.6 |
| Bradi3g28350 | Glycosyltransferase, GT2 family, CESA4 | 3.0 |
| Bradi4g30540 | Glycosyltransferase, GT2 family, CESA7 | 2.8 |
| Bradi3g33140 | Glycosylhydrolase, β-Expansin | 2.7 |
| Bradi3g19087 | Glycosyltransferase, GT2 family, CSLC | 2.6 |
| Bradi4g28260 | Glycosyltransferase, GT77 family, Extensin | 2.5 |
| Bradi1g10347 | Glycosylhydrolase, GH17 family | 2.3 |
| Lignin synthesis | | |
| Bradi2g23370 | Laccase | 12.6 |
| Bradi1g66720 | Laccase | 12.3 |
| Bradi3g58560 | Copper ion binding | 11.6 |
| Bradi1g27910 | Peroxidase | 11.3 |
| Bradi2g09690 | Peroxidase | 6.9 |
| Bradi2g20840 | Peroxidase | 5.9 |
| Bradi1g27920 | Peroxidase | 5.3 |
| Bradi3g30590 | Ferulic acid 5-hydroxylase 1 (FAH1) | 5.1 |
| Bradi2g54680 | Laccase | 4.7 |
| Bradi4g44810 | Laccase | 4.3 |
| Bradi3g38540 | Copper ion binding | 4.5 |
| Bradi1g24880 | Laccase | 4.3 |
| Bradi4g11850 | Laccase | 4.3 |
| Bradi4g28920 | Copper transporter protein ATOX1-related | 4.3 |
| Bradi1g43680 | Peroxidase | 4.0 |
| Bradi1g38297 | Peroxidase | 3.2 |
| Bradi3g05750 | 4-coumarate-CoA ligase 3 (4CL3) | 3.1 |
| Bradi1g32870 | Peroxidase | 3.1 |
| Bradi1g45790 | Copper ion binding protein | 2.9 |
| Bradi1g68900 | Peroxidase | 2.9 |
| Bradi3g39420 | Caffeoyl CoA 3-O-methyltransferase (CCoAOMT) | 2.8 |
| Bradi3g16530 | Caffeic acid O-methyltransferase (COMT4) | 2.8 |
| Bradi1g31320 | 4-coumarate-CoA ligase 1 (4CL1) | 2.4 |
| Bradi3g09240 | Copper binding protein | 2.3 |
| Lipid transfer | | |
| Bradi2g17550 | Lipid transfer protein | 8.5 |
| Bradi2g17530 | Lipid transfer protein | 7.8 |
| Bradi2g30490 | Lipid transfer protein | 3.8 |
| Bradi1g19470 | Lipid transfer protein | 6.1 |
| Bradi2g54970 | Lipid transfer protein | 4.9 |
| Bradi2g32950 | Lipid transfer protein | 4.7 |
| Bradi2g17540 | Lipid transfer protein | 4.4 |
| Bradi5g17930 | Lipid transfer protein | 4.2 |
| Transport | | |
| Bradi3g39800 | Dicarboxylate transporter | 7.8 |
| Bradi1g78100 | Arsenite transport | 6.5 |
| Bradi1g45190 | Amino acid transporter | 6.3 |
| Bradi3g05570 | Potassium ion transporter | 6.2 |
| Bradi1g03500 | Proton-dependent oligopeptide transporter | 5.3 |
| Bradi3g48950 | Ammonium transporter | 5.0 |
| Bradi4g21790 | Proton-dependent oligopeptide transporter | 5.0 |
| Bradi3g37850 | Potassium ion transporter | 4.7 |
| Bradi1g21800 | Sugar transporter | 4.6 |
| Bradi3g51280 | Major facilitator superfamily | 3.7 |
| Bradi3g28920 | UDP-glucuronic acid transporter | 3.6 |
| Bradi2g07830 | Aquaporin transporter | 3.6 |
| Bradi1g69770 | Aluminum activated citrate transporter | 3.4 |
| Bradi1g34140 | ATPase-like zinc transporter | 3.3 |
| Bradi5g17990 | ATP dependent copper transporter | 3.2 |
| Bradi1g25937 | EamA-like transporter | 3.1 |
| Bradi4g28000 | Sugar transporter | 2.7 |
| Bradi3g16130 | ABC transporter | 2.7 |
| Bradi1g73170 | Sucrose transporter | 2.7 |
| Bradi1g17830 | Potassium transporter | 2.6 |
| Bradi3g39077 | Oligopeptide transporter | 2.6 |
| Bradi4g34510 | PINFORMED-Like auxin efflux carrier | 2.5 |
| Bradi2g24910 | Amino acid transporter | 2.5 |
| Bradi3g32390 | Tetracycline transporter | 2.5 |
| Bradi3g34560 | ZIP Zinc transporter | 2.5 |
| Bradi5g24170 | Sulfate transporter | 2.4 |
| Bradi3g51250 | Mechanosensitive ion channel | 2.4 |
| Bradi1g59830 | Amino acid transporter | 2.3 |

TABLE 4.1-continued

Genes repressed by GNRF in GNRF-OE stems

| Gene name | Gene description | Fold change |
|---|---|---|
| Bradi1g34210 | Cation transmembrane transporter | 2.3 |
| Bradi4g08130 | ABC transporter | 2.1 |

GNRF Represses Meristem Identity Genes and Floral Integrators

Considering that GNRF-OE plants lacked the ability to transition from vegetative to reproductive growth, and many flowering associated genes were repressed as measured by microarray, flowering pathway genes were further investigated by QRT-PCR. I initially sought to validate the microarray results by analyzing the expression of FUL1, FUL2 and CENTRORADIALIS-LIKE1 HOMOLOGOUS TO TFL1 (RCN2) (FIG. 15). The primary stem was collected and flash frozen from developmentally equivalent plants at BBCH stage 5 (Hong et al., 2011) when the inflorescence had just begun to emerge from the flag leaf sheath. Eight to ten plants were individually analyzed for transcript abundance. In agreement with the microarray data, FUL1, FUL2 and RCN2 were significantly down-regulated in GNRF-OE stems. The same genes were modestly, but not significantly up-regulated in the gnrf-1 stems.

Figure 16A:
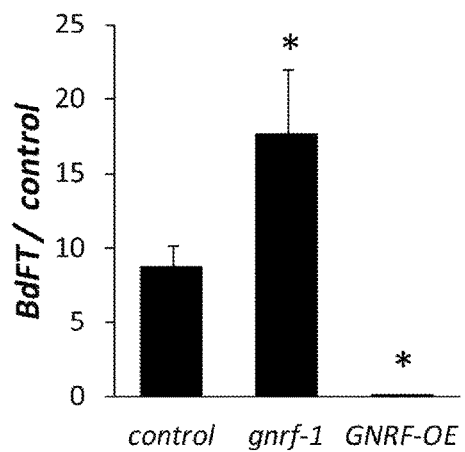
Figure 16B:
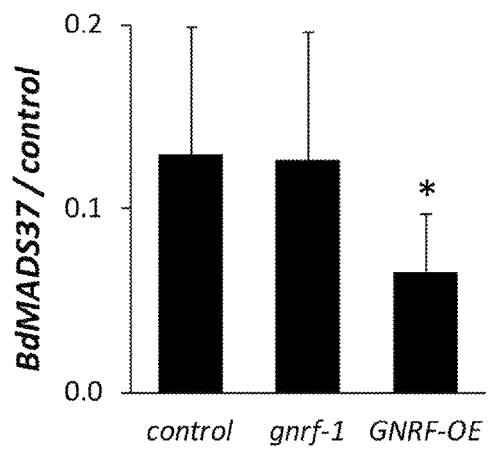
Figure 16C:
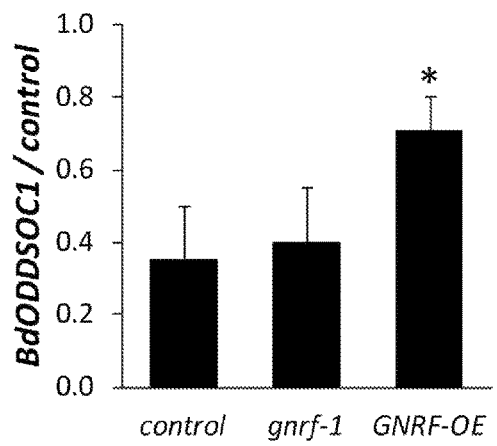
Figure 16D:
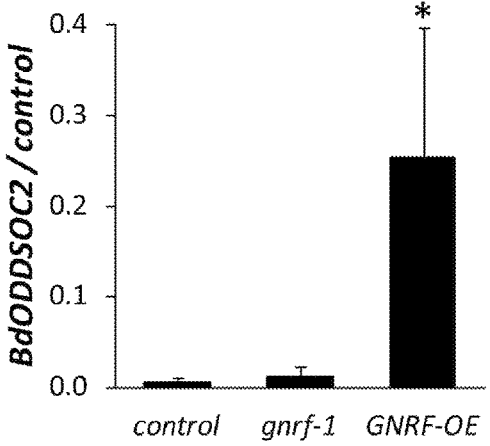

Next relative transcript abundance of the mobile flowering signal was investigated. FLOWERING LOCUST, or florigen, is an activator of flowering and one of the terminal genes in this pathway (Higgins et al., 2010). The protein functions as a mobile signal that moves from the leaf to the shoot apex to initiate flowering. Accordingly, leaf tissue was used to investigate the relative abundance of FT transcripts. As might be expected, BdFT was undetectable in GNRF-OE leaves and significantly up-regulated in gnrf-1 leaves (FIG. 16A). In order to better understand this dynamic, I investigated several putative upstream repressors of FT. FLOWERING LOCUS C (FLC) and SHORT VEGETATIVE PHASE (SVP) act as immediate repressors of FT in *A. thaliana* and served as initial candidates in *B. distachyon* (Ruelens et al., 2013). While SVP expression was not altered in GNRF-OE (data not shown), expression of other FLC-like genes was altered (FIG. 16B-D). BdMADS37, BdODDSOC1 and BdODDSOC2 are *B. distachyon* orthologs of *A. thaliana* FLC and are collectively referred to as the FLC-like genes. BdMADS37 was down-regulated in GNRF-OE leaves and BbODDSOC1 and BdODDSOC2 were significantly up-regulated in GNRF-OE leaves. The expression of BdMADS37, BDODDSOC, and BdODDSOC2 were at similar levels to controls in gnrf-1 leaves.

GNRF Regulates Genes Associated with Cellulose, Xylan and Lignin Biosynthesis in Stem Tissue Since NACs play a key regulatory role in secondary cell wall biosynthesis, the gene expression of several cell wall genes was measured in GNRF-OE and gnrf-1 plants to investigate the transcriptional function of GNRF. Quantitative real time PCR was utilized to examine transcript abundance of the transgenes and candidate cell wall genes using the same cDNA samples used for detecting flowering pathway genes. As expected, GNRF was significantly up-regulated in GNRF-OE stems (FIG. 17). Three genes involved in cellulose biosynthesis namely BdCESA4/7/8 and two genes associated with lignin biosynthesis namely, BdCAD1 and BdCOMT4 and a gene with a predicted role in xylan biosynthesis BdGT47-1 were analyzed for changes in transcript abundance (FIG. 18). All five cellulose and lignin genes were significantly down-regulated in GNRF-OE stems. The same genes were also found to be repressed in the microarray data set (Table 4.1). Conversely, the expression of BdCESA4/7, BdCAD1, and BdCOMT4 was significantly up-regulated in gnrf-1stems. While the putative xylan gene, BdGT47-1, was significantly up-regulated in the gnrf-1lines, no change was observed in GNRF-OE lines. Overall, these data suggest that GNRF is a repressor of cellulose and lignin gene expression.

GNRF Influences Cell Wall Composition

In order to correlate gene expression with levels of cellulose and lignin, histochemical assays were performed on stem tissue. First internodes of fully senesced stems were sectioned and stained with phloroglucinol-HCl to investigate possible changes in lignin content. While no visible changes in staining intensities were observed between control and gnrf-1 stem cross sections, GNRF-OE sclerenchyma fibers and vascular bundles exhibited a lighter shade of orange (FIG. 19A). Since phloroglucinol-HCl stains O-4-linked coniferyl and sinapyl aldehydes in lignified tissue in a concentration indicative manner, the lighter staining pattern observed in GNRF-OE is likely due to a decrease in total lignin. Fully senesced pulverized tissue was used to measure the acetyl bromide soluble lignin (ABSL) content to further investigate the function of GNRF on cell wall composition and lignification (FIG. 19B). As expected based on the phloroglucinol-HCL staining, the GNRF-OE stem was significantly reduced in ABSL content compared to the controls whereas no significant change was observed between the gnrf-1 and control samples. As many lignin and lignin related genes were repressed in the GNRF-OE stems it was expected to observe a reduction in lignin composition which is further demonstrated by the significant reduction in ABSL.

Discussion

Several NAC transcription factors have been shown to play crucial roles in secondary cell wall biosynthesis and overall plant growth and development. The *B. distachyon* NAC family is estimated to comprise 99 NAC proteins among which only one has been functionally characterized to date (International *Brachypodium* Initiative, 2010; Valdivia et al., 2013). GNRF was selected for functional characterization as it is highly expressed in stems mirroring an expression profile similar to that of characterized secondary cell wall regulators such as NST1, SND1 and SND2 (Mitsuda et al., 2005; Zhong et al., 2007). Moreover it is co-regulated with cell wall biosynthesis genes.

An over-expression construct was used to develop gain-of-function mutants with constitutive over-expression of GNRF. Simultaneously, a homozygous mutant allele harboring a nonsynonymous point mutation was isolated from a TILLING mutant collection to investigate the gnrf-1 loss-of-function phenotypes. Surprisingly, over-expression mutants demonstrated a persistent vegetative phenotype. GNRF-OE plants failed to flower and could not transition into the reproductive stage. Conversely the gnrf-1 mutants flowered significantly earlier than control plants. However apart from our observations, there are no known reports associating SND2 orthologs with flowering or floral transition. Over-expression of SND2 in *A. thaliana* had no adverse effects on flowering (Zhong et al., 2008). Additionally, no change in flowering time was observed with PtSND2 over-expression mutants (Wang et al., 2013). These observations warranted further investigation of the flowering pathway in *B. distachyon*. I first confirmed the over-expression of the GNRF transgene and as expected GNRF transcripts were significantly up-regulated in both leaf and stem tissue in the GNRF-OE plants. FT is the key signal in the vegetative to reproductive transition, during which FT accumulates in *A. thaliana* leaves prior to flowering (Gu et al., 2010; Wu et al., 2013; Lv et al., 2014). In order to investigate the influence of GNRF on FT we analyzed FT expression in mutant leaves. As expected FT was not detectable in GNRF-OE leaves whereas it was significantly up-regulated in gnrf-1 leaves, in agreement with the flowering time phenotypes observed for these mutants. Unavailability of the mobile signal FT in GNRF-OE leaves is a possible cause for the persistant vegetative phenotype. Recently, FT was also shown to bind phospholipids to accelerate flowering (Nakamura et al., 2014). Another possibility is the repression of numerous lipid transporter genes, which in turn influence the availability of these phospholipids thus delaying the flowering process.

However the direct cause of the persistent vegetative growth of GNRF-OE is most likely due to the >50 fold reduction of two MADS box transcription factors, FUL1 and FUL2. VRN1 is the closest ortholog to *A. thaliana* meristem identity gene AP1 in temperate cereals and is responsible for transitioning the meristem into a flower bud. Moreover FUL is another meristem identity gene homologous to AP1 (Ream et al., 2014). Even though BdMADS33/FUL1 and MADS10/FUL2 have not been functionally characterized, they are the closest orthologous proteins to AP1 and FUL, respectively, and therefore most likely regulate floral meristem identity in *B. distchyon*. It is interesting to note that similar to the GNRF-OE phenotype, mutations in *A. thaliana* FUL gene along with mutations in AP1/CAT genes result in non-flowering leafy phenotypes (Ferrandiz et al., 2000). This provides strong support for the function of FUL1 and FUL2 as floral identity genes in *B. distachyon*. AtAP1 is negatively regulated by the meristem identity gene TERMINAL FLOWER and the organ identity gene AGAMOUS. It is also regulated by the floral homeotic gene PISTILLATA and its interacting partner APETALA3 (Sundström et al., 2006). However, to date there is no indication of any involvement of a NAC transcription factor in the regulation of these redundant floral homeotic genes AP1/CAL/FUL. Furthermore, there are no known NAC transcription factors associated with dicot or monocot flowering pathways (Higgins et al., 2010). GNRF is the first NAC protein to be associated with the flowering pathway in *B. distachyon*. The architecture of flowering pathways in *B. distachyon* and *A. thaliana* are similar in some aspects, for instance vegetative to reproductive transition is signaled by leaf localized FT expression (Corbesier et al.; Wu et al., 2013; Lv et al., 2014). In both species, activation of orthologous floral meristem identity genes results in flowering. Interestingly, the vernalization responses between these two species are significantly different.

GNRF is the closest ortholog to SND2. Very little is known about the function of SND2 in any plant system. To date it has only been shown to activate cell wall biosynthesis in *A. thaliana* and poplar (Zhong et al., 2008; Grant et al., 2010; Wang et al., 2013). Based on the protein similarity and the expression profile, GNRF likely has a similar function to SND2. In support of that, we have shown that GNRF is a regulator of cellulose, lignin and hemicellulose genes. Over-expression of GNRF resulted in a significant reduction of these genes in the GNRF-OE stems. Therefore, unlike SND2, GNRF appears to act as a repressor of cell wall biosynthesis. However, analysis of GNRF sequence revealed no apparent repression domains. Based on the microarray results, a handful of lignin genes, peroxidases, lacasses and copper ion transporters were repressed by GNRF. Since these components are essential for polymerization of lignin monomers, cell wall lignification should be effected in the GNRF-OE mutants. Complementing the expression analysis, histo-chemical analysis revealed a qualitative reduction in stem lignin in the GNRF-OE stems. This observation was further validated by the significantly lower levels of acetyl bromide soluble lignin content measured in GNRF-OE stems.

Based on the expression profiling and cell wall composition analysis it is evident that GNRF is involved in cell wall regulation. Unlike other classical cell wall regulators, GNRF has profound pleiotropic effects. Based on transcription profiling, GNRF is associated with cell wall, floral transition and transporters of numerous substrates. However using microarray expression analysis, direct and indirect regulation via GNRF over-expression is hard to decipher. Many different genes may be directly regulated by GNRF, including FUL1 and FUL2. Further experiments will be required to determine whether these genes are under direct regulation by GNRF as well as if these genes share common GNRF binding sites.

BIBLIOGRAPHY

Arvidsson S, Kwasniewski M, Riano-Pachon D, Mueller-Roeber B (2008) QuantPrime—a flexible tool for reliable high-throughput primer design for quantitative PCR. BMC Bioinformatics 9: 465

Brown D M, Zeef L A H, Ellis J, Goodacre R, Turner S R (2005) identification of novel genes in *Arabidopsis* involved in secondary cell wall formation using expression profiling and reverse genetics. Plant Cell 17: 2281-2295

Carroll A, Somerville C (2009) Cellulosic biofuels. Annu Rev Plant Biol 60: 165-182

Cassan-Wang H, Goué N. Saidi M N, Legay S, Sivadon P, Goffner D, Grima-Pettenati J (2013) Identification of novel transcription factors regulating secondary cell wall formation in *Arabidopsis* Front Plant Sci 4

Cui M H, Yoo K S, Hyoung S. Nguyen H T K, Kim Y Y, Kim H J, Ok S H, Yoo S D, Shin J S (2013) An *Arabidopsis* R2R3-MYB transcription factor, AtMYB20, negatively regulates type 2C serine/threonine protein phosphatases to enhance salt tolerance. FEBS Letters 587: 1773-1778 d'Yvoire M B, Bouchabke-Coussa O, Voorend W, Antelme S, Cézard L, Legée F, Lebris P, Legay S, Whitehead C, McQueen-Mason S J, Gomez L D, Jouanin L, Lapierre C, Sibout R (2012) Disrupting the cinnamyl alcohol dehydrogenase 1 gene (BdCAD1) leads to altered lignification and improved saccharification in *Brachypodium distachyon*. Plant J 73: 496-508

Dalmais M, Antelme S, Ho-Yue-Kuang S, Wang Y, Darracq O, d'Yvoire M B, Cezard L, Legee F, Blondet E, Oria N, Troadec C, Brunaud V, Jouanin L, Hofte H, Bendahmane A, Lapierre C, Sibout R (2013) A TILLING platform for functional genomics in *Brachypodium distachyon*. PLoS One 8: e65503

Du H, Wang Y-B, Xie Y, Liang Z, Jiang S-J, Zhang S-S, Huang Y-B, Tang Y-X (2013) Genome-wide identification and evolutionary and expression analyses of MYB-related genes in land plants. DNA Res 20: 437-448

Dubos C, Stracke R, Grotewold E, Weisshaar B, Martin C, Lepiniec L (2010) MYB transcription factors in *Arabidopsis*. Trends Plant Sci 15: 573-581

Ehlting J, Mattheus N, Aeschliman D S, Li E, Hamberger B, Cullis I F, Zhuang J, Kaneda M, Mansfield S D, Samuels L, Ritland K, Ellis B E, Bohlmann J, Douglas C J (2005) Global transcript profiling of primary stems from *Arabidopsis thaliana* identifies candidate genes for missing links in lignin biosynthesis and transcriptional regulators of fiber differentiation. Plant J 42: 618-640

Esau K (1977) Anatomy of seed plants, Ed 2nd. John Wiley & Sons, New York

Finn R D, Clements J, Eddy S R (2011) HMMER web server: interactive sequence similarity searching. Nucleic Acids Res. 39: W29-W37

Folkers U, Berger J, Hulskamp M (1997) Cell morphogenesis of trichomes in *Arabidopsis*: differential control of primary and secondary branching by branch initiation regulators and cell growth. Development 124: 3779-3786

Fornalé S, Lopez E, Salazar-Henao J E, Fernández-Nohales P, Rigau J, Caparros-Ruiz D (2014) AtMYB7, a new player in the regulation of UV-sunscreens in *Arabidopsis thaliana*. Plant Cell Physiol 55: 507-516

Fornalé S, Shi X, Chai C, Encina A, Irar S, Capellades M, Fuguet E, Torres J-L, Rovira P, Puigdomènech P, Rigau J, Grotewold E, Gray J, Caparrós-Ruiz D (2010) ZmMYB31 directly represses maize lignin genes and redirects the phenylpropanoid metabolic flux. Plant J 64: 633-644

Foster C E, Martin T M, Pauly M (2010) Comprehensive compositional analysis of plant cell walls (lignocellulosic biomass) Part I: lignin. J Vis Exp: e1745

Haga N, Kato K, Murase M, Araki S, Kubo M, Demura T, Suzuki K. Müller I, Voß U, Jürgens G, Ito M (2007) R1R2R3-Myb proteins positively regulate cytokinesis through activation of KNOLLE transcription in *Arabidopsis thaliana*. Development 134: 1101-1110

Haga N, Kobayashi K, Suzuki T, Maeo K, Kubo M, Ohtani M, Mitsuda N, Demura T, Nakamura K, Jürgens G, Ito M (2011) Mutations in MYB3R1 and MYB3R4 cause pleiotropic developmental defects and preferential down-regulation of multiple G2/M-specific genes in *Arabidopsis*. Plant Physiol 157: 706-717

Handakumbura P, Matos D, Osmont K, Harrington M, Heo K, Kafle K, Kim S, Baskin T, Hazen S (2013) Perturbation of *Brachypodium distachyon* CELLULOSE SYNTHASE A4 or 7 results in abnormal cell walls. BMC Plant Biol 13: 131

Handakumbura P P, Hazen S P (2012) Transcriptional regulation of grass secondary cell wall biosynthesis: playing catch-up with *Arabidopsis thaliana*. Front Plant Sci 3: 74

Hatton D, Sablowski R, Yung M-H, Smith C, Schuch W, Bevan M (1995) Two classes of cis sequences contribute to tissue-specific expression of a PAL2 promoter in transgenic tobacco. Plant J 7: 859-876

Hong S-Y, Seo P, Yang M-S, Xiang F, Park C-M (2008) Exploring valid reference genes for gene expression studies in *Brachypodium distachyon* by real-time PCR. BMC Plant Biol 8: 112

Hong S Y, Park J H, Cho S H, Yang M S, Park C M (2011) Phenological growth stages of *Brachypodium distachyon*: codification and description. Weed Res 51: 612-620

Hussey S G, Mizrachi E, Creux N M, Myburg A A (2013) Navigating the transcriptional roadmap regulating plant secondary cell wall deposition. Front Plant Sci 4: 325

International *Brachypodium* Initiative (2010) Genome sequencing and analysis of the model grass *Brachypodium distachyon*. Nature 463: 763-768

Jessup R (2009) Development and status of dedicated energy crops in the United States. In Vitro Cell Dev-Pl 45: 282-290

Jin H, Cominelli E, Bailey P, Parr A, Mehrtens F, Jones J, Tonelli C, Weisshaar B, Martin C (2000) Transcriptional repression by AtMYB4 controls production of UV-protecting sunscreens in *Arabidopsis*. EMBO J 19: 6150-6161

Katiyar A, Smita S, Lenka S, Rajwanshi R, Chinnusamy V, Bansal K (2012) Genome-wide classification and expression analysis of MYB transcription factor families in rice and *Arabidopsis*. BMC Genomics 13: 544

Katoh K, Misawa K, Kuma Ki, Miyata T (2002) MAFFT: a novel method for rapid multiple sequence alignment based on fast Fourier transform. Nucleic Acids Research 30: 3059-3066

Kellogg E (2001) Evolutionary history of the grasses. Plant Physiol 125: 1198-1205

Kim W-C, Kim J-Y, Ko J-H, Kim J, Han K-H (2013) Transcription factor MYB46 is an obligate component of the transcriptional regulatory complex for functional expression of secondary wall-associated cellulose synthases in *Arabidopsis thaliana*. J Plant Physiol 170: 1374-1378

Kim W-C, Ko J-H, Han K-H (2012) Identification of a cis-acting regulatory motif recognized by MYB46, a master transcriptional regulator of secondary wall biosynthesis. Plant Mol Biol 78: 489-501

Ko J-H, Han K-H, Park S. Yang j (2004) Plant dody weight-induced secondary growth in *Arabidopsis* and its transcription phenotype revealed by whole-transcriptome profiling. Plant Physiol 135: 1069-1083

Ko J-H, Kim W-C, Han K-H (2009) Ectopic expression of MYB46 identifies transcriptional regulatory genes involved in secondary wall biosynthesis in *Arabidopsis*. Plant J 60: 649-665

Ko J H, Jeon H A Y, Kim W C, Kim J Y, Han K H (2014) The MYB46/MYB83-mediated transcriptional regulatory programme is a gatekeeper of secondary wall biosynthesis. Ann Bot Kubo M, Udagawa M, Nishikubo N, Horiguchi G, Yamaguchi M, Ito J, Mimura T, Fukuda H, Demura T (2005) Transcription switches for protoxylem and metaxylem vessel formation. Genes Dev 19: 1855-1860

Lee S, Warnick T, Pattathil S, Alvelo-Maurosa J, Serapiglia M, McCormick H, Brown V, Young N, Schnell D, Smart L, Hahn M, Pedersen J, Leschine S, Hazen S (2012) Biological conversion assay using *Clostridium phytofermentans* to estimate plant feedstock quality. Biotechnol Biofuels 5: 5

Lee S J, Wamick T A, Leschine S B, Hazen S P (2012) A high-throughput biological conversion assay for determining lignocellulosic quality. Methods Mol Biol. 918: 341-349

Legay S, Lacombe E, Goicoechea M, Briere C, Seguin A, Mackay J, Grima-Pettenati J (2007) Molecular characterization of EgMYB1, a putative transcriptional repressor of the lignin biosynthetic pathway. Plant science: an international journal of experimental plant biology 173: 542-549

Liang Y-K, Dubos C, Dodd I C, Holroyd G H, Hetherington A M, Campbell M M (2005) AtMYB61, an R2R3-MYB transcription factor controlling stomatal aperture in *Arabidopsis thaliana*. Curr Biol 15: 1201-1206

Liu C, Wang X, Xu Y, Deng X, Xu Q (2014) Genome-wide analysis of the R2R3-MYB transcription factor gene family in sweet orange (*Citrus sinensis*). Mol Biol Rep: 1-17

Lois R, Dietrich A, Schulz W (1989) A phenylalanine ammonia-lyase gene from parsley: structure, regulation and identification of elicitor and light responsive cis-acting elements. EMBO J 8: 1641-1648

Lyons E, Pedersen B, Kane J, Alam M, Ming R, Tang H, Wang X, Bowers J, Paterson A, Lisch D, Freeling M (2008) Finding and Comparing Syntenic Regions among *Arabidopsis* and the Outgroups Papaya, Poplar, and Grape: CoGe with Rosids. Plant Physiology 148: 1772-1781

Matos D A, Whitney I P, Harrington M J, Hazen S P (2013) Cell walls and the developmental anatomy of the *Brachypodium distackvon* stem internode. PLoS ONE 8: e80640

McCarthy R L, Zhong R, Ye Z-H (2009) MYB83 is a direct target of SND1 and acts redundantly with MYB46 in the regulation of secondary cell wall biosynthesis in *Arabidopsis*. Plant Cell Physiol 50: 1950-1964

Mitsuda N, Matsui K, Ikeda M, Nakata M, Oshima Y, Nagatoshi Y, Ohme-Takagi M (2011) CRES-T, an effective gene silencing system utilizing chimeric repressors. In L Yuan, S E Perry, eds, Plant Transcription Factors, Vol 754. Humana Press, pp 87-105

Mu R-L, Cao Y-R, Liu Y-F, Lei G, Zou H-F, Liao Y, Wang H-W, Mang W-K, Ma B, Du J-Z, Yuan M, Zhang L S, Chen S-Y (2009) An R2R3-type transcription factor gene AtMYB59 regulates root growth and cell cycle progression in *Arabidopsis*. Cell Res 19: 1291-1304

Müller D, Schmitz G, Theres K (2006) Blind homologous R2R3 Myb genes control the pattern of lateral meristem initiation in *Arabidopsis*. Plant Cell 18: 586-597

Mutwil M, Klie S, Tohge T, Giorgi F M, Wilkins O, Campbell M M, Fernie A R, Usadel Br, Nikoloski Z, Persson S (2011) PlaNet: combined sequence and expression comparisons across plant networks derived from seven species. Plant Cell 23: 895-910

Öhman D, Demedts B, Kumar M, Gerber L, Gorzsas A, Goeminne G, Hedenström M, Ellis B, Boerjan W, Sundberg B (2013) MYB103 is required for FERULATE-5-HYDROXYLASE expression and syringyl lignin biosynthesis in *Arabidopsis* stems. Plant J 73: 63-76

Ori N, Eshed Y, Chuck G, Bowman J L, Hake S (2000) Mechanisms that control knox gene expression in the *Arabidopsis* shoot. Development 127: 5523-5532

Oshima Y, Shikata M, Koyama T, Ohtsubo N, Mitsuda N, Ohme-Takagi M (2013) MIXTA-like transcription factors and WAX INDUCER1/SHINE1 coordinately regulate cuticle development in *Arabidopsis* and *Torenia fournieri*. Plant Cell 25: 1609-1624

Persson S, Wei H, Milne J, Page G P, Somerville C R (2005) Identification of genes required for cellulose synthesis by regression analysis of public microarray data sets. Proc Natl Acad Sci USA 102: 8633-8638

Preston J, Wheeler J, Heazlewood J, Li S F, Parish R W (2004) AtMYB32 is required for normal pollen development in *Arabidopsis thaliana*. Plant J 40: 979-995

Pruneda-Paz J L, Breton G, Para A, Kay S A (2009) A functional genomics approach reveals CHE as a component of the *Arabidopsis* circadian clock. Science 323: 1481-1485

Raes J, Rohde A, Christensen J, Peer Y, Boerjan W (2003) Genome-wide characterization of the lignification toolbox in *Arabidopsis*. Plant Physiol 133: 1051-1071

Ronquist F, Teslenko M, van der Mark P, Ayres D L, Darling A, Höhna S, Larget B, Liu L, Suchard M A, Huelsenbeck J P (2012) MrBayes 3.2: Efficient Bayesian Phylogenetic Inference and Model Choice Across a Large Model Space. Systematic Biology 61: 539-542

Schuetz M, Smith R, Ellis B (2013) Xylem tissue specification, patterning, and differentiation mechanisms. J Exp Bot 64: 11-31

Shen H, He X, Poovaiah C R, Wuddineh W A, Ma J, Mann D G J, Wang H, Jackson L, Tang Y, Neal Stewart C, Chen F, Dixon R A (2012) Functional characterization of the switchgrass (*Panicum virgatum*) R2R3-MYB transcription factor PvMYB4 for improvement of lignocellulosic feedstocks. New Phytol 193: 121-136

Tamura K, Peterson D, Peterson N, Stecher G, Nei M, Kumar S (2011) MEGA5: molecular evolutionary genetics analysis using maximum likelihood, evolutionary distance, and maximum parsimony methods. Mol. Biol. Evol. 28: 2731-2739

Thompson J D, Linard B, Lecompte O, Poch O (2011) A Comprehensive Benchmark Study of Multiple Sequence Alignment Methods: Current Challenges and Future Perspectives. PLoS ONE 6: e18093

Trabucco G M, Matos D A, Lee S J, Saathoff A, Priest H, Mockler T C, Sarath G, Hazen S P (2013) Functional characterization of cinnamyl alcohol dehydrogenase and caffeic acid O-methyltransferase in *Brachypodium distachyon*. BMC Biotechnol 13: 61

Valdivia E R, Herrera M T, Gianzo C, Fidalgo J, Revilla G, Zarra I, Sampedro J (2013) Regulation of secondary wall synthesis and cell death by NAC transcription factors in the monocot *Brachypodium distachyon*. J Exp Bot 64: 1333-1343

Vogel J (2008) Unique aspects of the grass cell wall. Curr Opin Plant Biol 11: 301-307

Vogel J, Garvin D, Leong O, Hayden D (2006) *Agrobacterium*-mediated transformation and inbred line development in the model grass *Brachypodium distachyon*. Plant Cell Tiss Org 84: 100179-100191

Wilkins O, Nahal H, Foong J, Provart N J, Campbell M M (2009) Expansion and diversification of the *Populus* R2R3-MYB family of transcription factors. Plant Physiol 149: 981-993

Winter D, Vinegar B, Nahal H, Ammar R, Wilson G V, Provart N J (2007) An electronic fluorescent pictograph browser for exploring and analyzing large-scale biological data sets. PLoS ONE 2: e718

Worsdell W C (1902) The evolution of the vascular tissue of plants. Bot Gaz 34: 216-223

Zhao K, Bartley L (2014) Comparative genomic analysis of the R2R3 MYB secondary cell wall regulators of *Arabidopsis*, poplar, rice, maize, and switchgrass. BMC Plant Biol 14: 135

Zhao K, Bartley, Laura (2014) Comparative Genomic Analysis of the R2R3 MYB Secondary Cell Wall Regulators of *Arabidopsis*, Poplar, Rice, Maize, and Switchgrass. BMC Plant Biol. Accepted Zhong R, Lee C, McCarthy R L, Reeves C K, Jones E G, Ye Z-H (2011) Transcriptional activation of secondary wall biosynthesis by rice and maize NAC and MYB transcription factors. Plant Cell Physiol 52: 1856-1871

Zhong R, Lee C, Ye Z-11 (2010) Evolutionary conservation of the transcriptional network regulating secondary cell wall biosynthesis. Trends in Plant Science 15: 625-632

Zhong R, Lee C, Zhou J, McCarthy R L, Ye Z-H (2008) A battery of transcription factors involved in the regulation of secondary cell wall biosynthesis in *Arabidopsis*. Plant Cell 20: 2763-2782

Zhong R, Richardson E A, Ye Z H (2007) The MYB46 transcription factor is a direct target of SND1 and regulates secondary wall biosynthesis in *Arabidopsis*. Plant Cell 19: 2776-2792

Zhong R, Ye Z-H (2012) MYB46 and MYB83 bind to the SMRE sites and directly activate a suite of transcription factors and secondary wall biosynthetic genes. Plant Cell Physiol 53: 368-380

Zhou J, Lee C, Zhong R, Ye Z H (2009) MYB58 and MYB63 are transcriptional activators of the lignin biosynthetic pathway during secondary cell wall formation in *Arabidopsis*. Plant Cell 21: 248-266

The invention is described with reference to various specific and preferred embodiments and techniques. However, it should be understood that many variations and modifications may be made while remaining within its scope. All referenced publications, patents and patent documents are intended to be incorporated by reference, as though individually incorporated by reference.

What is claimed is:

1. A transgenic plant, plant cell, plant part or seed, wherein the transgenic plant, plant cell, plant part or seed comprises a recombinant polynucleotide comprising a heterologous promoter which increases expression of a Secondary Wall Associated MYB1 (SWAM1) protein as compared to a non-transgenic control plant of the same plant species, wherein the heterologous promotor is operably linked to a nucleic acid sequence encoding said SWAM1 protein, wherein the nucleic acid sequence encoding said SWAM1 protein is set forth in SED ID NO:4 or has at least 95% amino acid sequence identity to the amino acid sequence of SEQ ID NO: 4, and wherein increase in said SWAM1 protein in said transgenic plant increases lignin content and above ground plant biomass as compared to a non-transgenic control plant of the same plant species lacking said recombinant polynucleotide.

2. The transgenic plant, plant cell, plant part or seed of claim 1, wherein the transgenic plant, plant cell, plant part or seed is a miscanthus, switchgrass, sorghum, poplar, wheat, rye, corn, barley, oat, rapeseed, potato, rice, soybean, or *Brachypodium distachyon* plant, plant cell, plant part or seed.

3. A method of increasing lignin content and above ground plant biomass, the method comprising transforming a plant with a recombinant polynucleotide which comprises a heterologous promoter that increases the expression of a Secondary Wall Associated MYB1 (SWAM1) protein, wherein said heterologous promoter is operably linked to a nucleic acid sequence encoding said SWAM1 protein, wherein said SWAM1 protein is set forth in SEQ ID NO: 4 or has at least 95% amino acid sequence identity to the amino acid sequence of SEQ ID NO: 4, and wherein expression of said SWAM1 protein increases lignin content and above ground plant biomass of the transgenic plant as compared to a non-transgenic control plant of the same species lacking said recombinant polynucleotide.

4. The method of claim 3, wherein the transgenic plant is a miscanthus, switchgrass, sorghum, poplar, wheat, rye, corn, barley, oat, rapeseed, potato, rice, soybean, or *Brachypodium distachyon* plant.

* * * * *